(12) United States Patent
Luxon et al.

(10) Patent No.: US 10,265,442 B2
(45) Date of Patent: Apr. 23, 2019

(54) DEVICES AND METHODS FOR MANAGING CHEST DRAINAGE

(71) Applicant: Esculon, LLC, San Francisco, CA (US)

(72) Inventors: Evan S. Luxon, Omaha, NE (US); Daniel R. Burnett, San Francisco, CA (US); Randy Preston, San Francisco, CA (US); Ryan Coughlin, Omaha, NE (US); Mark Ziegler, Palo Alto, CA (US); Derek Wallin, Seattle, WA (US)

(73) Assignee: Esculon, LLC, Omaha, NE (US)

( * ) Notice: Subject to any disclaimer, the term of this patent is extended or adjusted under 35 U.S.C. 154(b) by 0 days.

(21) Appl. No.: 15/840,487

(22) Filed: Dec. 13, 2017

(65) Prior Publication Data

US 2018/0104391 A1 Apr. 19, 2018

Related U.S. Application Data

(63) Continuation of application No. PCT/US2017/020791, filed on Mar. 3, 2017.

(60) Provisional application No. 62/303,361, filed on Mar. 3, 2016, provisional application No. 62/328,560, filed on Apr. 27, 2016, provisional application No. 62/365,770, filed on Jul. 22, 2016, provisional application No. 62/448,546, filed on Jan. 20, 2017.

(51) Int. Cl.
*A61M 1/00* (2006.01)
*A61M 31/00* (2006.01)
*A61M 37/00* (2006.01)
*B67C 3/16* (2006.01)
*B65B 1/04* (2006.01)

(52) U.S. Cl.
CPC ........... *A61M 1/0035* (2014.02); *A61M 1/008* (2013.01); *A61M 1/0023* (2013.01); *A61M 1/0033* (2014.02); *A61M 1/0078* (2013.01); *A61M 2205/14* (2013.01); *A61M 2205/15* (2013.01); *A61M 2205/18* (2013.01); *A61M 2205/3313* (2013.01); *A61M 2205/3317* (2013.01); *A61M 2205/3324* (2013.01); *A61M 2205/3334* (2013.01); *A61M 2205/3337* (2013.01); *A61M 2205/3344* (2013.01); *A61M 2205/52* (2013.01)

(58) Field of Classification Search
CPC ........ A61M 1/00; A61M 31/00; A61M 37/00; B65B 31/04; B65B 1/04; B67C 3/16
See application file for complete search history.

(56) References Cited

U.S. PATENT DOCUMENTS 5,127,905 A  7/1992  Lemieux
5,738,656 A  4/1998  Wagner
(Continued)

FOREIGN PATENT DOCUMENTS

WO  WO 2016/054051  *  9/2014
WO  WO 2016/054051     4/2016

*Primary Examiner* — Tatyana Zalukaeva
*Assistant Examiner* — Ilya Treyger
(74) *Attorney, Agent, or Firm* — Levine Bagade Han LLP

(57) ABSTRACT

Disclosed is a chest drainage system which reduces or eliminates pooling of blood/liquid and/or clogging/clotting in the drainage tube and/or chest tube, and provides objective and accurate measures of drained fluid volume and chest air leak. The chest drainage system continuously monitors chest tube and drainage tube status and clears pooled liquid in the drainage tube, and/or a clogged chest tube when necessary to restore negative pressure to the chest.

22 Claims, 61 Drawing Sheets

(56) References Cited

U.S. PATENT DOCUMENTS

| | | |
|---|---|---|
| 2005/0192548 A1 | 9/2005 | Dolliver et al. |
| 2006/0122558 A1 | 6/2006 | Sherman et al. |
| 2012/0059340 A1 | 3/2012 | Larsson |
| 2014/0200558 A1 | 7/2014 | McDaniel |
| 2015/0343120 A1 | 12/2015 | Yokoi et al. |

* cited by examiner

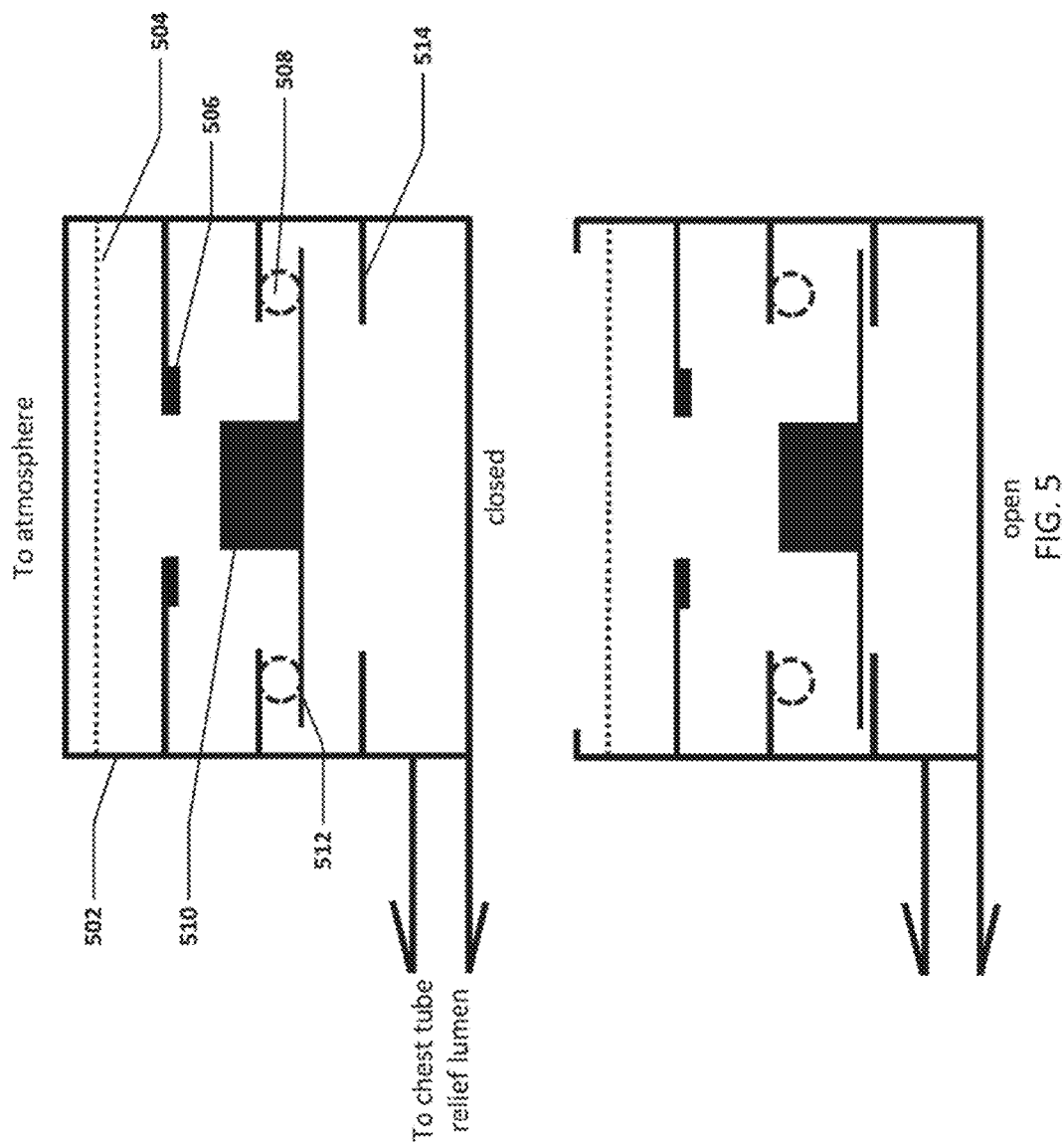

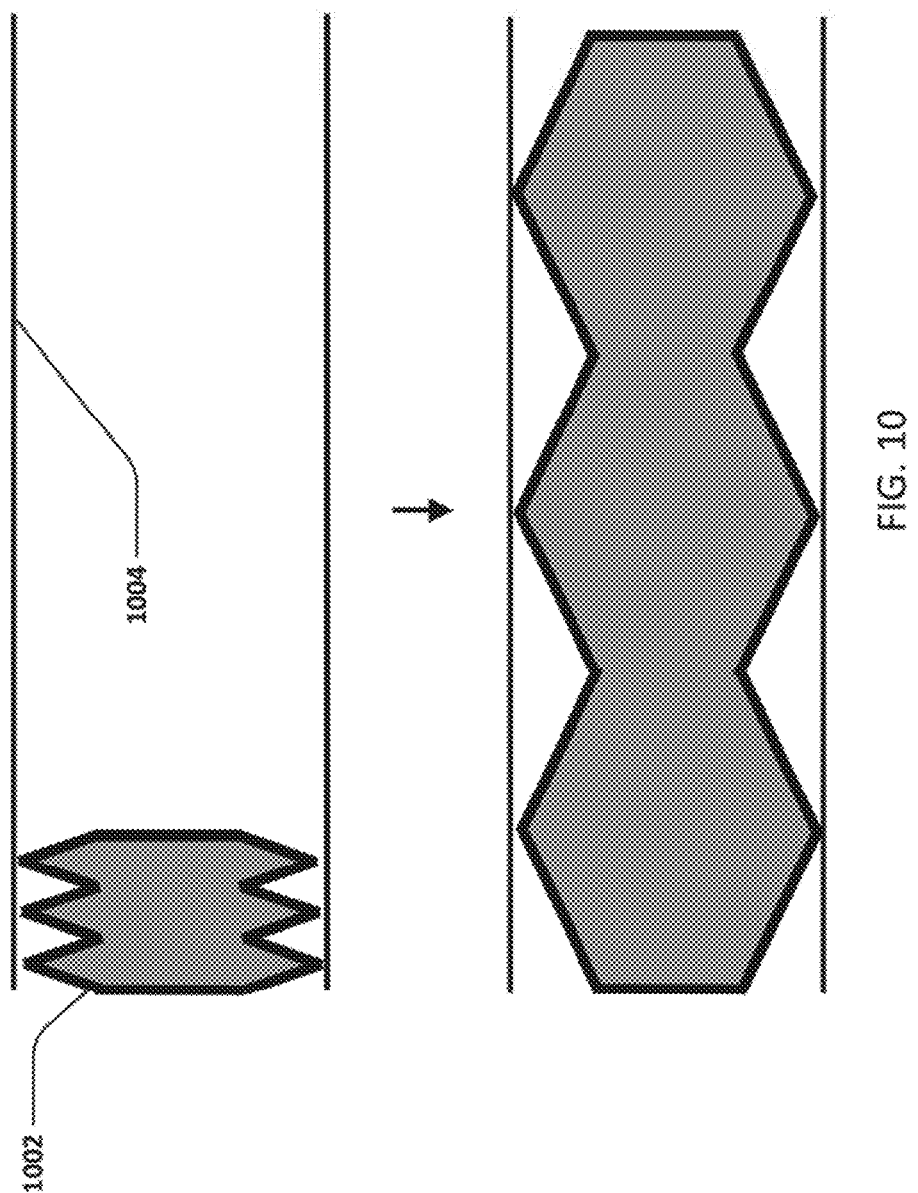

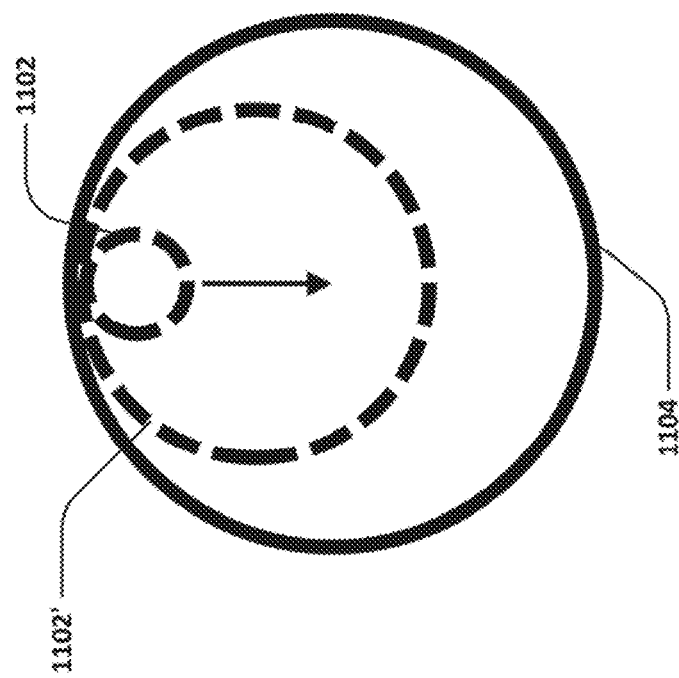
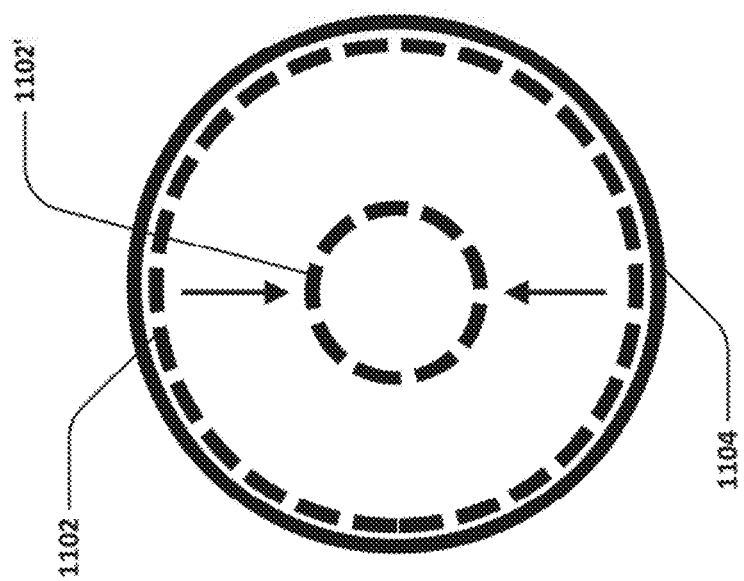

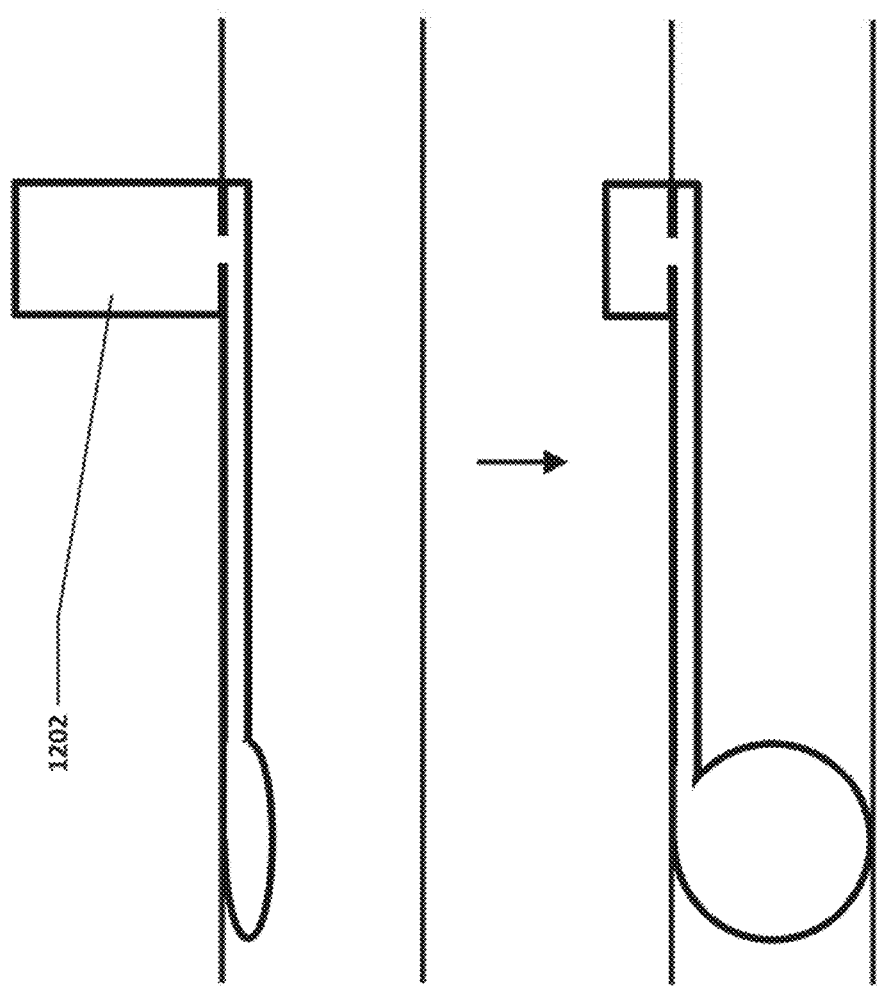

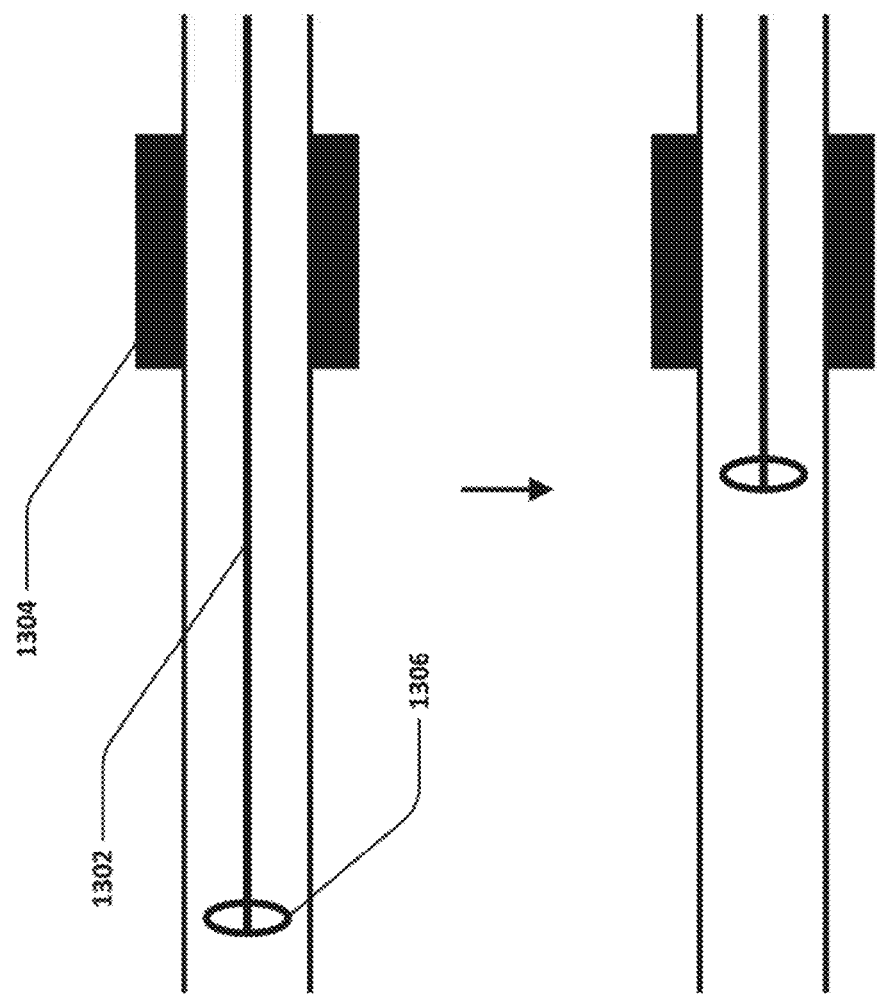

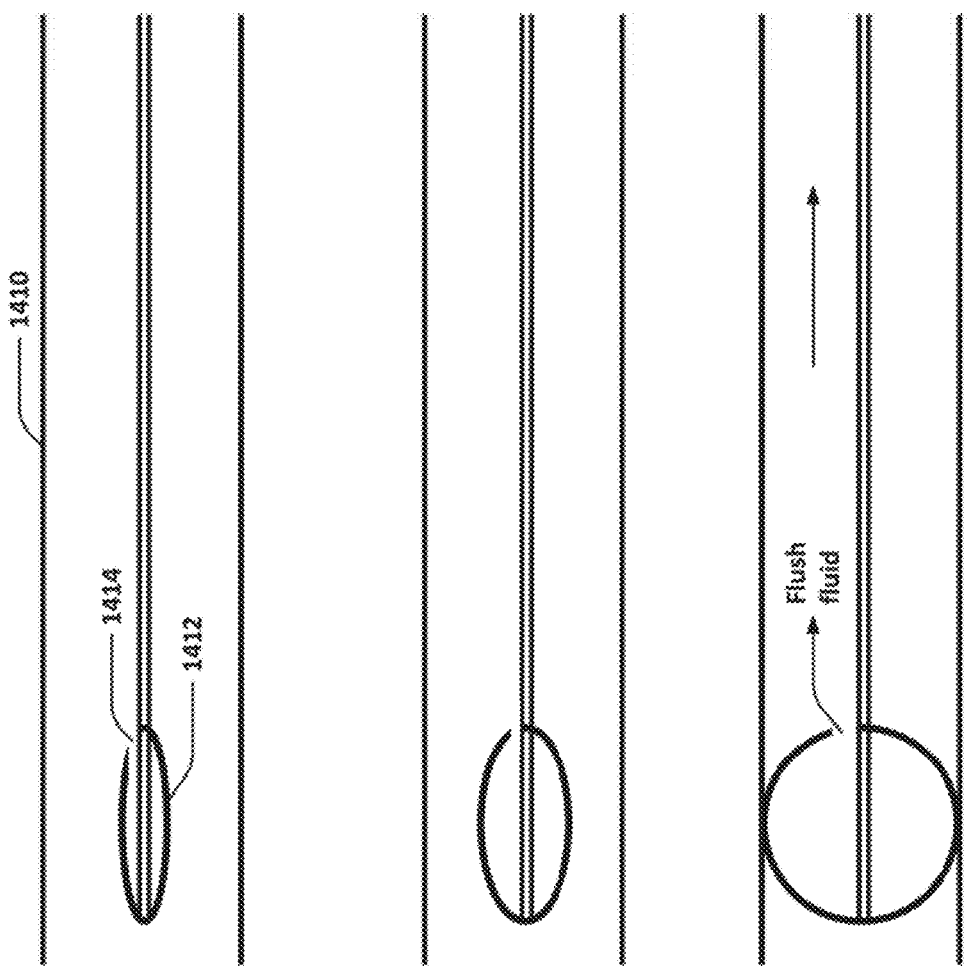

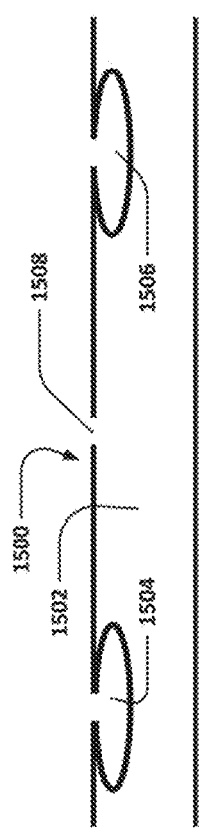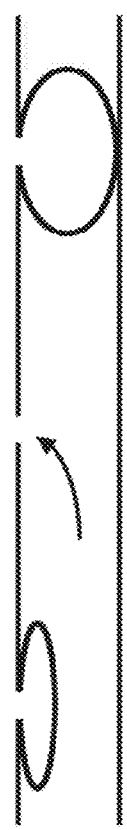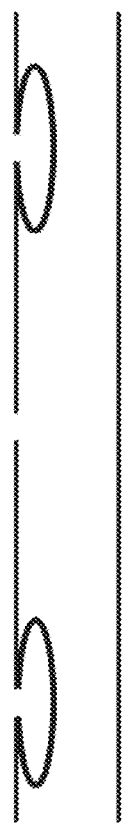

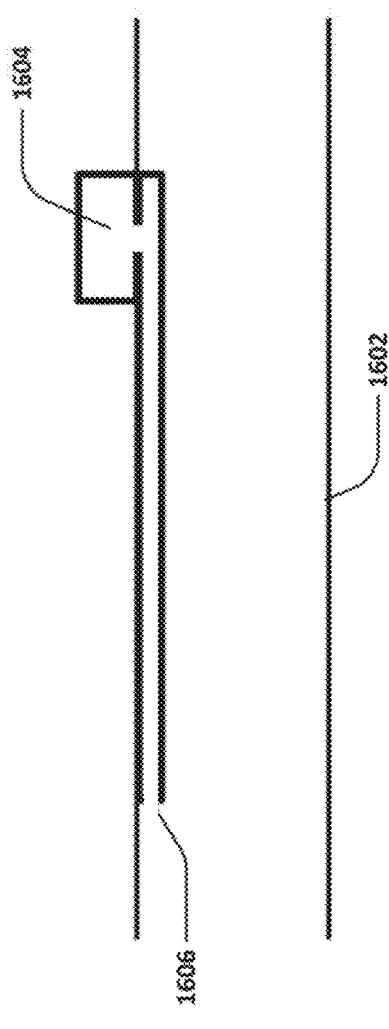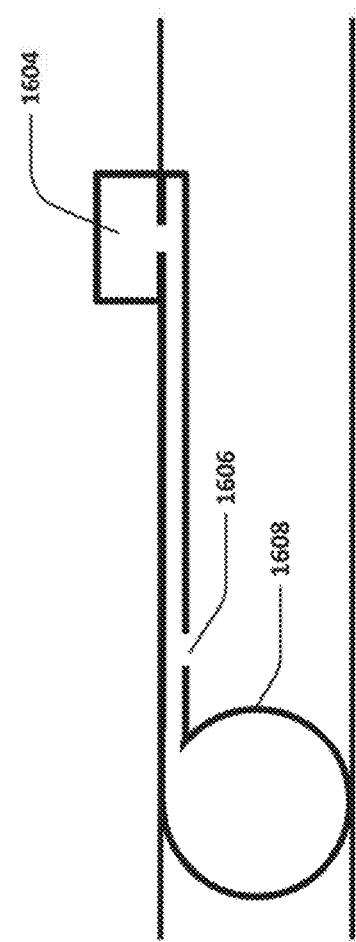

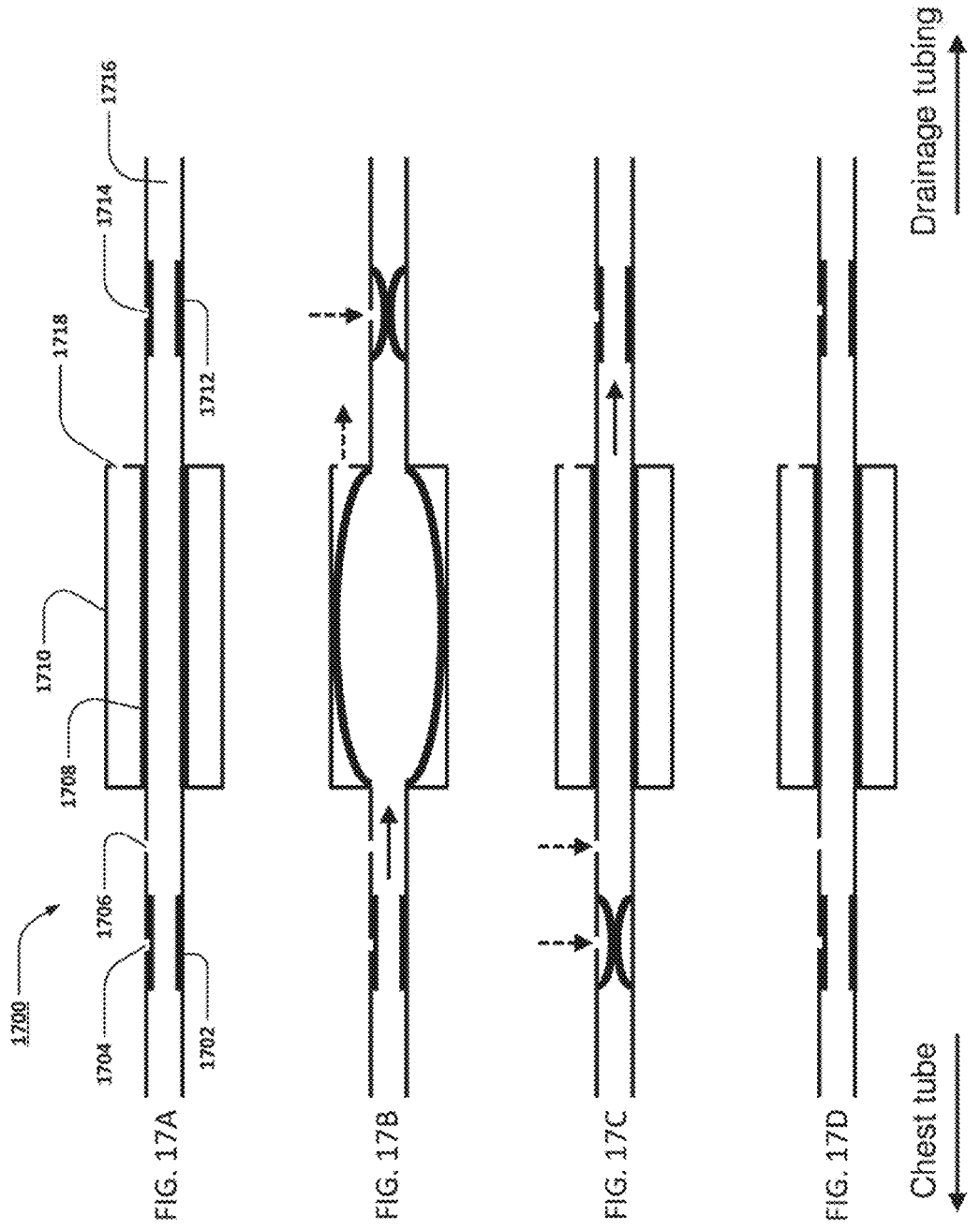

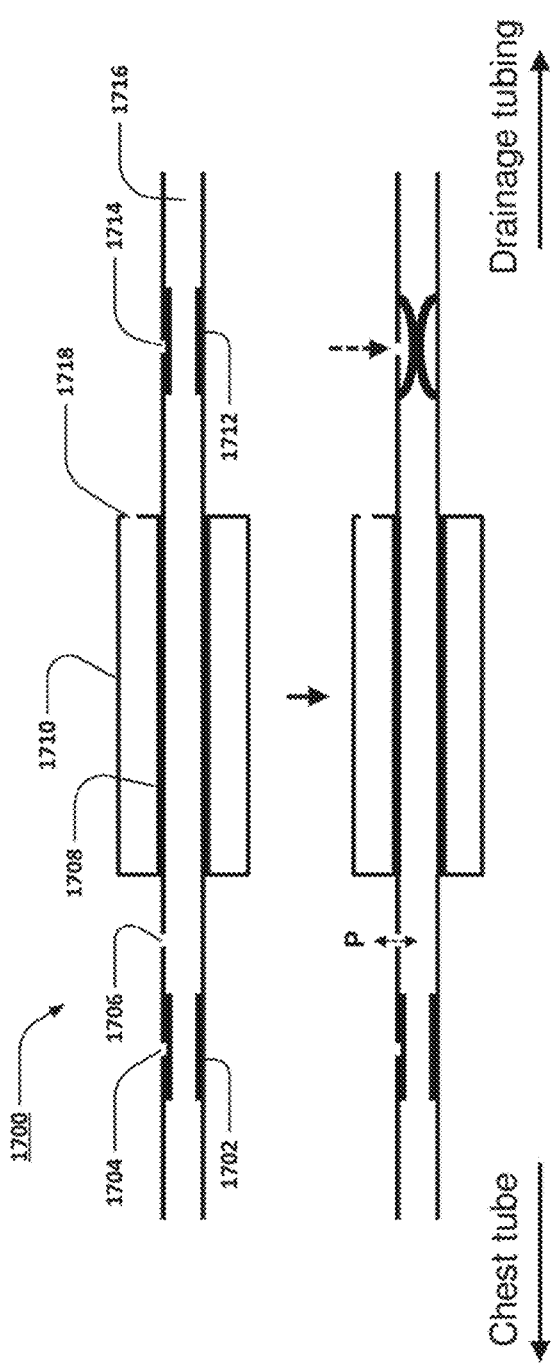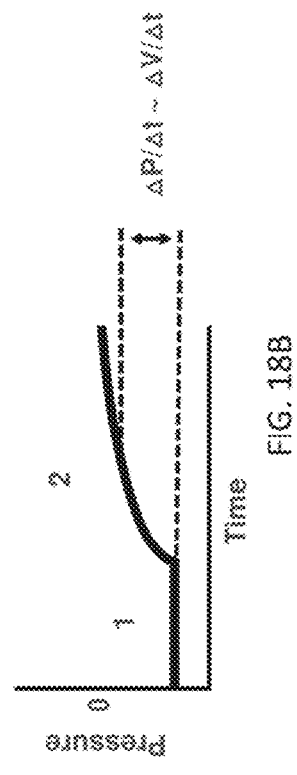
FIG. 18A
FIG. 18B

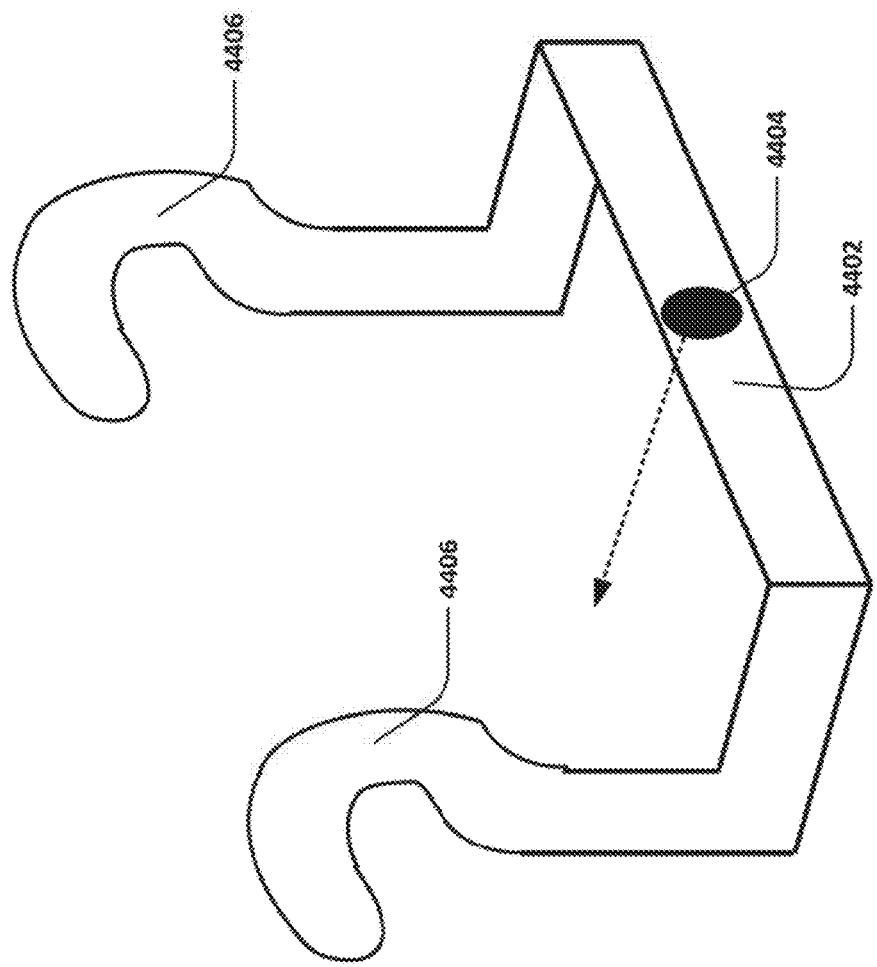

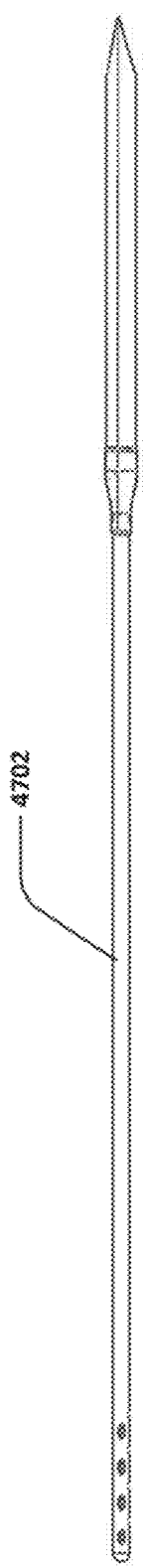
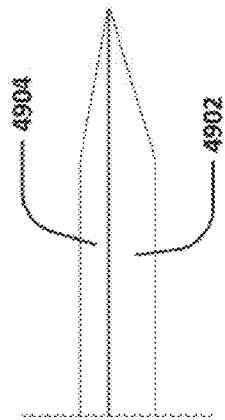
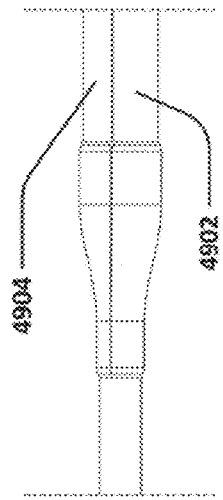
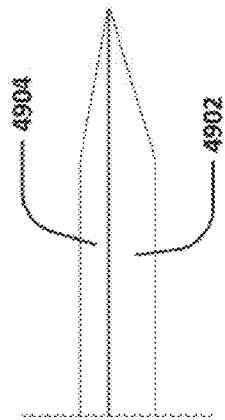
FIG. 47
FIG. 48
FIG. 49
FIG. 50

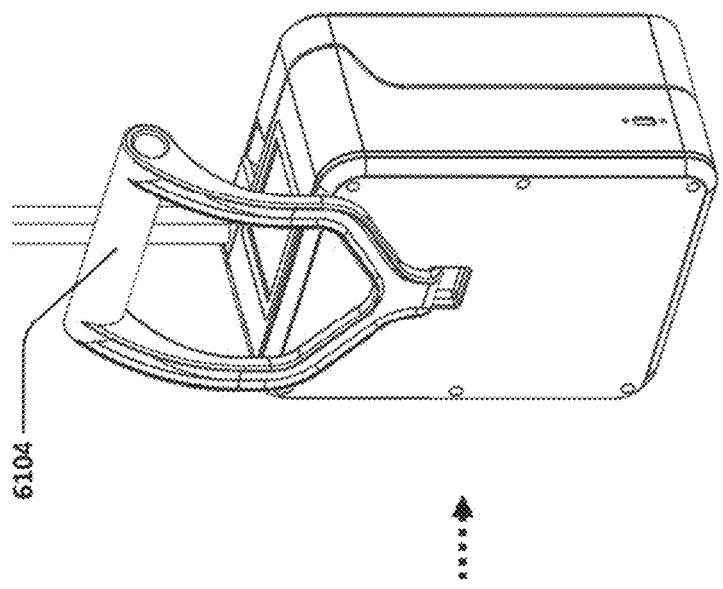
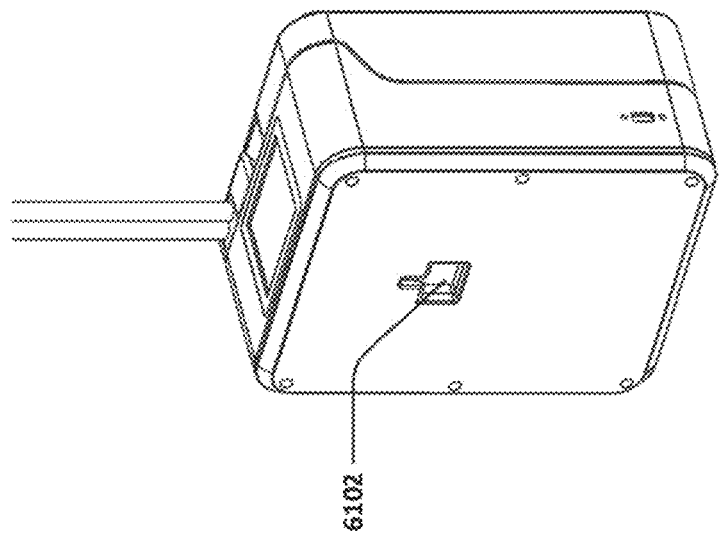
FIG. 61

DEVICES AND METHODS FOR MANAGING CHEST DRAINAGE

CROSS-REFERENCE TO RELATED APPLICATIONS

This application is a continuation of PCT/US2017/020791 filed Mar. 3, 2017, which claims the benefit of priority to U.S. Provisional Application No. 62/303,361 filed Mar. 3, 2016 and U.S. Provisional Application No. 62/328,560 filed Apr. 27, 2016 and U.S. Provisional Application No. 62/365,770 filed Jul. 22, 2016 and U.S. Provisional Application No. 62/448,546 filed Jan. 20, 2017, each of which is incorporated herein by reference in its entirety.

FIELD OF THE INVENTION

The present invention relates to wound and surgical drainage.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

Chest tubes are required any time air and/or liquid accumulates in the chest cavity, disrupting normal pulmonary or cardiac function. Suction is applied continuously to remove excess air and/or fluid from the chest until the internal wounds have healed, at which point the chest tubes can be removed. One of the most common uses of chest tubes is to drain the area around the heart after cardiac surgery.

Despite their benefits, current chest tube systems suffer from two major flaws. First, as liquid drains from the chest toward the suction container, it can pool in the drainage tubing and prevent the applied negative pressure from being transmitted to the chest. When this occurs, the pressure in the chest can be reduced to zero or even become positive. Second, clogs can form that obstruct the chest tube, which prevent the negative pressure from being transmitted to the chest and inhibit drainage. In fact, 36% of cardiac surgery patients experience chest tube clogging. When proper drainage is inhibited due to these factors, patients are at increased risk for accumulation of fluid around the heart, known as pericardial tamponade, which results in shock and can be fatal. Additionally, the lungs may be compressed, which can lead to respiratory compromise and can be fatal as well.

Pooling of liquid in the drainage line can theoretically be remedied by keeping the tubing straight from the patient to the collection container. However, this is nearly impossible in practice, as some slack is required to prevent accidental dislodging of the tube from the body. To combat clogging, clinicians use two methods known as milking and stripping. Milking refers to line manipulations such as lifting, squeezing, or kneading. Stripping refers to a pulling along the length of the tube with the thumb and forefinger to increase the amount of suction at the end of the tube. However, these methods have not been shown to be effective at improving chest tube suction or drainage. In fact, stripping has actually been discouraged because it is possible to create extremely high negative pressures (up to −370 cmH2O) that may damage the tissue.

In addition to these functional flaws, current systems also rely on measures of collected fluid volume and rate of chest air leak, which are subjective and lead to imprecision and inaccuracies in the measurements. As a result, clinicians make cautious clinical decisions based on these measurements, keeping patients in the hospital longer than necessary.

SUMMARY OF THE INVENTION

A chest drainage system is needed which reduces or eliminates pooling of blood/liquid and/or clogging/clotting in the drainage tube and/or chest tube, and provides objective and accurate measures of collected fluid volume and chest/thoracic air leak.

In one variation, the drainage system may generally comprise a tube configured for insertion into a body of a subject, wherein the tube defines a tube relief lumen and tube drainage lumen in fluid communication with one another; and a tube relief lumen valve in fluid communication with the tube relief lumen such that a pressure differential is formed between an ambient pressure and the tube relief lumen, wherein the tube relief lumen valve is configured to close at a first pressure differential and to open at a second pressure differential which is different from the first pressure differential.

In one exemplary method of maintaining the drainage system, the method may generally comprise providing a tube having a tube relief lumen and tube drainage lumen in fluid communication with one another and configured for insertion into a body of a subject, and a tube relief lumen valve in fluid communication with the tube relief lumen; and configuring the tube relief lumen valve from a closed configuration into an open configuration, where the closed configuration is formed when a first pressure differential between an ambient pressure and the tube relief lumen is created and where the open configuration is formed when a second pressure differential between the ambient pressure and the tube relief lumen is created, wherein the first pressure differential is different from the second pressure differential.

In another variation of the drainage system, the system may generally comprise a tube configured for insertion into a body of a subject, wherein the tube defines a tube relief lumen and tube drainage lumen in fluid communication with one another; a tube relief lumen valve in fluid communication with the tube relief lumen; a suction pump in fluid communication with the tube drainage lumen; and a controller in communication with the tube, wherein the controller is programmed to actuate the suction pump at a first level of suction which maintains the tube relief lumen valve in a closed configuration and at a second level of suction which reconfigures the tube relief lumen valve to an open configuration.

BRIEF DESCRIPTION OF THE DRAWINGS

FIG. 5 shows a magnetic embodiment of the chest tube valve.

FIG. 10 shows an accordion shaped balloon.

FIGS. 11A and 11B show chest tubes with incorporated balloons.

FIG. 12 shows an embodiment with a balloon valve including energy delivery.

FIG. 13 shows an embodiment which include a magnetic wire.

FIGS. 14A-14C show an embodiment of a chest tube.

FIGS. 15A-15D show an embodiment of a valve device.

FIGS. 16A-16B show an embodiment of a chest tube with a flush port.

FIGS. 17A-17D show an embodiment of a valve device.

FIGS. 18A and 18B show a method of measuring a chest/thoracic air leak using the chest drainage system.

FIG. 44 shows an embodiment of a mounting device.

FIGS. 47-50 show an embodiment of a dual-lumen chest tube.

FIG. 61 shows a modular attachment receptacle.

DETAILED DESCRIPTION OF THE INVENTION

Figure 1:
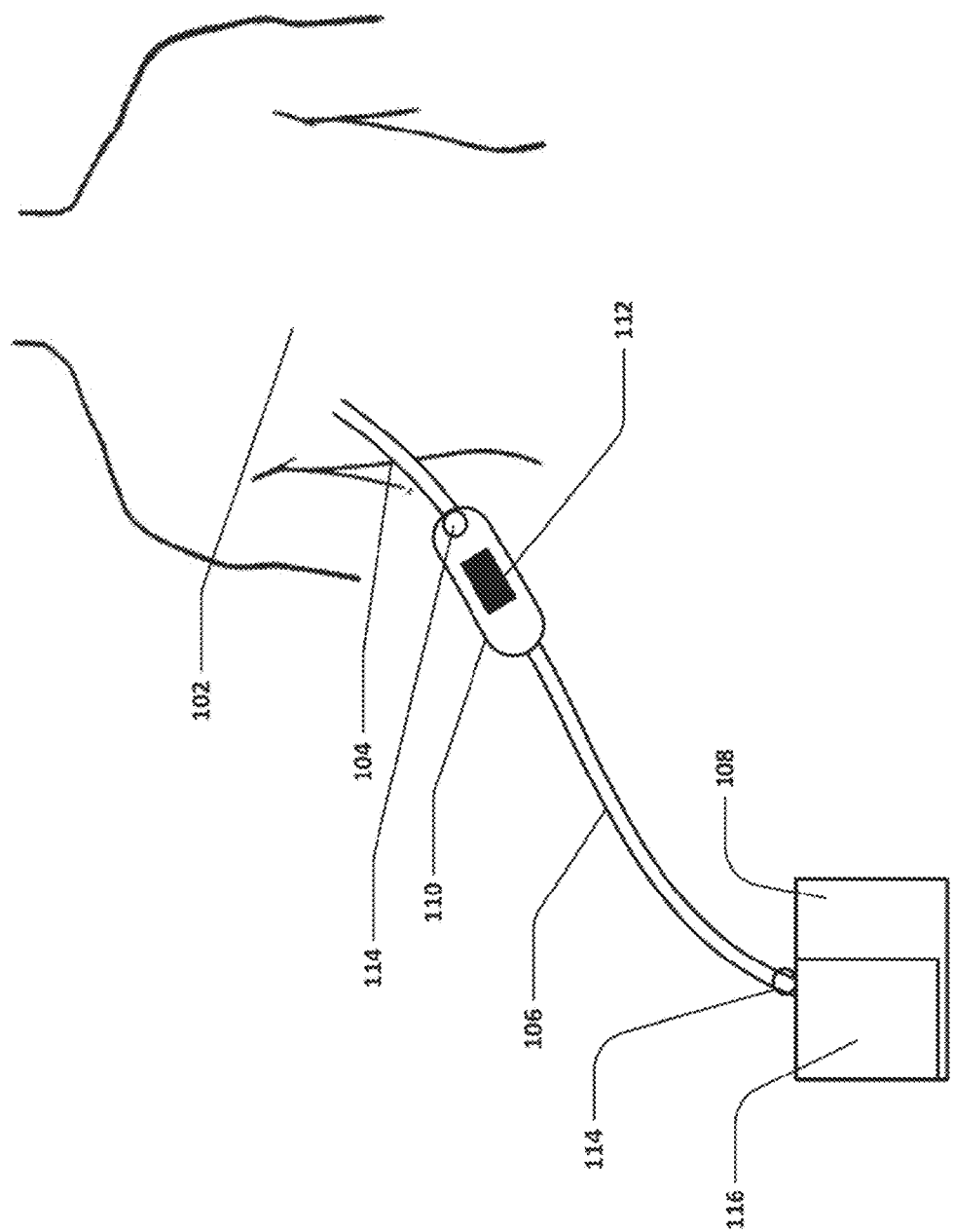
FIG. 1 shows an embodiment of the chest drainage system that does not include a relief lumen.

Disclosed is a chest drainage system which reduces or eliminates pooling of blood/liquid and/or clogging/clotting in the drainage tube and/or chest tube, and provides objective and accurate measures of drained fluid volume and chest air leak.

The chest drainage system continuously monitors chest tube and drainage tube status and clears pooled liquid in the drainage tube, and/or a clogged chest tube when necessary to restore negative pressure to the chest. The system may include active and/or passive valve functions, as well as a controller (also referred to herein as a monitor) for monitoring the pressures in the system. The controller may control a pump for assisting in clearance of pooled liquid and/or clots in the drainage tube and/or chest tube. The controller may also control any active valves and/or suction device in response to measured pressure signals. The chest drainage system performs four primary functions:

1. The chest drainage system detects pooled liquid in the drainage tube by monitoring the pressure at or near the chest tube-drainage tube interface (the tube-tube interface area). Pooled liquid in the drainage tube is indicated by a decrease in vacuum (increasing pressure). The chest drainage system may measure pressure with a sensor incorporated into the controller. The sensor may be in fluid communication with the tube-tube interface area via a fluid filled lumen (the relief lumen). The relief lumen may be open to atmosphere on the other end, and be filled with air. A valve (drainage tube valve or drainage tube relief lumen valve) may be used to open and close the relief lumen, and may include a vent which prevents the transmission of bacteria and viruses from the atmosphere into the relief lumen. The drainage tube valve may be opened and closed by the controller based on the measured pressure at the tube-tube interface area.

Alternatively, the pressure sensor may be placed at the tube-tube interface area, connected directly to atmosphere. In this embodiment, the pressure sensor is in communication with the controller and no relief lumen is present. Alternatively, the drainage tube valve may be passive, either with or without a relief lumen.

2. When pooled liquid is detected, the chest drainage system clears the drainage tube by opening the drainage tube relief lumen valve which is in fluid communication with the tube-tube interface area. Opening the drainage tube relief lumen valve allows air to sweep away the liquid in the drainage tube into the drainage container/reservoir. A pump which may be integrated with the controller, applies negative pressure to the drainage tube (via a collection reservoir/cassette/chamber). Optionally the pump may also apply positive pressure to the relief lumen (rather than its being open to atmospheric pressure) to help clear the blockage. Proper negative pressure at the chest is then restored. Optionally, the system may apply negative pressure (or an increased negative pressure) to the drainage tube without opening the relief lumen valve. This serves as a temporary measure to restore proper suction and may or may not clear a blockage. This measure may be performed when the controller senses a blockage in the drainage tube, or may be performed at limited temporal intervals.

3. Clots or clogs may form in the chest tube. To clear them, the suction magnitude applied at the tube-tube interface may be increased by the controller. A passive valve, in fluid communication with a chest tube relief lumen, may be configured to open when the pressure in the tube-tube interface drops below a set level. This valve (chest tube relief valve) may be open to atmospheric pressure and include a filter or vent to prevent bacteria etc. from entering the system. Once the chest tube relief valve is open, the chest tube will be cleared. The chest tube relief valve may be configured to close at a pressure differential which is less than that of the opening pressure, to ensure the valve stays open long enough for the chest tube to be cleared and to minimize the flow resistance of the valve. Alternatively, the chest tube relief valve, may be an active valve, which opens and closes based on pressures measured in the tube-tube interface area and/or in the chest tube relief lumen. An active chest tube relief valve may open and close at the same pressure differential or open and close at different pressure differentials.

In some embodiments, one or more of the valves are passive and set to open at a set pressure and stay open until the same, or another, set pressure is reached. In some embodiments, one or more of the valves are active. In either case, one or more valves may be set to open at one pressure, and close at another pressure.

FIG. 1 shows an embodiment of the chest drainage system that does not include a relief lumen. Patient chest 102 is drained using the chest drainage system. Chest tube 104 is in direct fluid communication with the chest cavity. Drainage tube 106 is in fluid communication with collection chamber 116 which may be connected to suction device/controller 108. Valve device 110 which includes vent/valve 112 is between chest tube 104 and drainage tube 106. Alternatively, vent/valve 112 may be incorporated into the chest tube and/or drainage tube. Valve device 110 is in fluid communication with both chest tube 104 and drainage tube 106. Valve device 110 may be controlled by a controller or may be controlled manually (this controller may be the same as, or different than, controller 108). The valve device may be used to periodically close off fluid flow from the chest tube and/or open vent/valve 112 to allow air to enter the drainage tube and clear any obstructions or restrictions in the drainage tube.

Pressure sensor(s) 114 may reside at various locations in the system. Here, a pressure sensor is shown incorporated within the valve device near chest tube 104, and also near suction device 108. Pressure sensors may also be located in other places in the system, for example, near the chest. Pressure sensed at one or more location may be used to determine whether there is a change in pressure anywhere in the system, which may be used to identify drainage tube blockages and/or chest tube blockages. If an impediment is detected, an audible alarm may sound, and/or the controller may automatically control the valve device to clear the drainage tube and/or chest tube. More detail on this is provided below.

Suction device 108 creates a negative pressure, or suction, force on the drainage tube (possibly via collection reservoir 116) which is in fluid communication with the valve device and chest tube. In this way, suction may be maintained on the chest cavity to promote chest fluid drainage and aid with patient breathing. The mechanism for creating the negative pressure may be a pump or any other suitable mechanism.

The controller may be incorporated into the suction device and/or the valve device and/or be separate. Any communication between the controller and the suction device and/or valve device may be wired or wireless.

Figure 2:
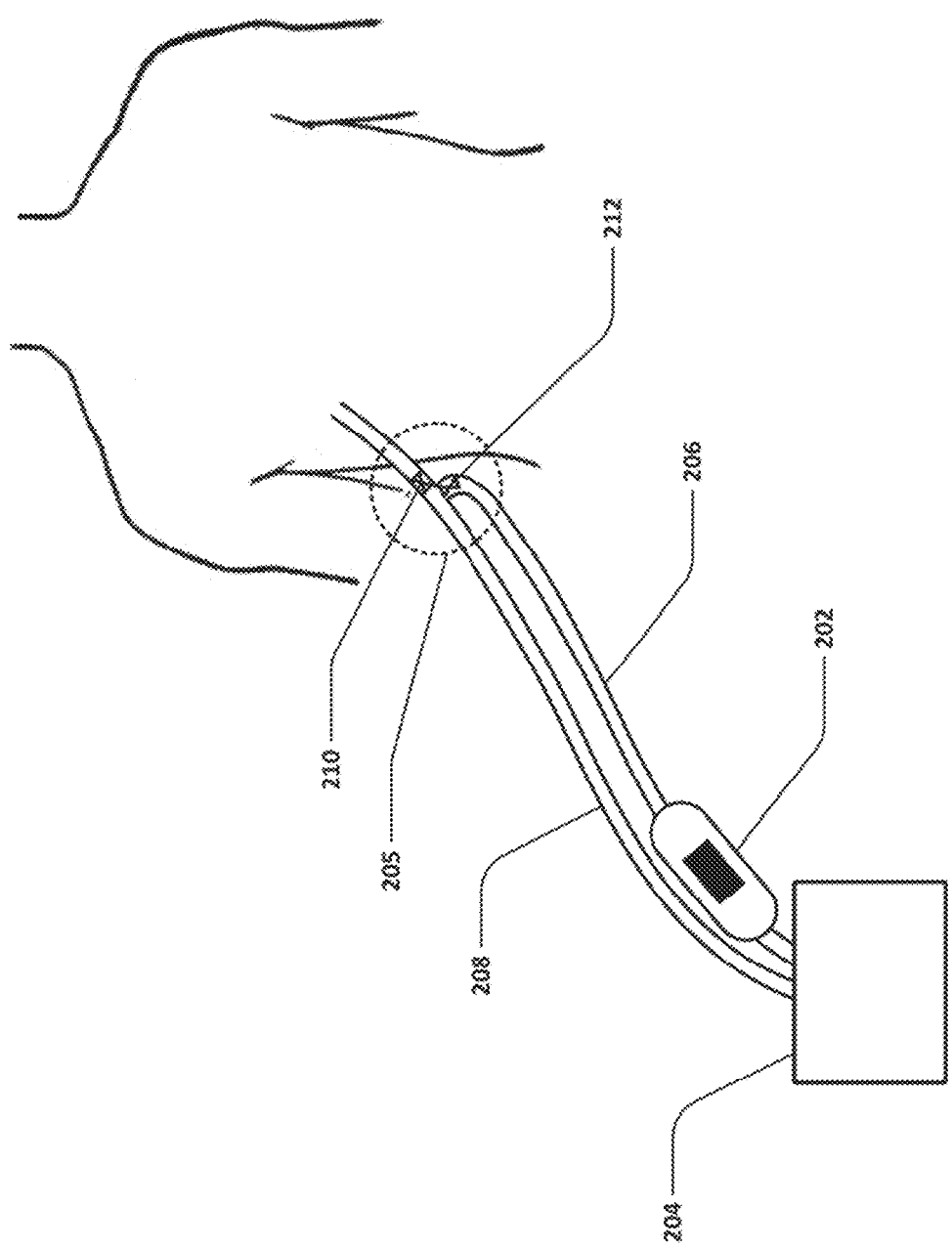
FIG. 2 shows another embodiment of the chest drainage system with active valves in the tube-tube interface area.

FIG. 2 shows another embodiment of the chest drainage system with active valves in the tube-tube interface area. In this embodiment valve device 202 is located near, or incorporated into, suction device/controller 204. The valve device is connected to drainage tube relief lumen 206. Pressure sensor(s) (not shown) may be located anywhere in the system, including near the tube-tube interface 205. If drainage tube 208 becomes blocked, as sensed by the pressure sensor(s), controller 204 opens valve 212 to allow clearing of the drainage line. This may also occur at regular temporal intervals as a preventative measure. Valve 210 may also be closed to seal off the chest tube. If a pump is used, it can assist with drainage by applying positive pressure to relief lumen 206 and/or negative pressure to drainage tube 208. In this embodiment, valves 210, 212, valve device 202 and suction device 204 are controlled by a controller which may be incorporated into the suction device and or valve device, or may be separate. Communications with the controller may be wired or wireless.

Figure 3:
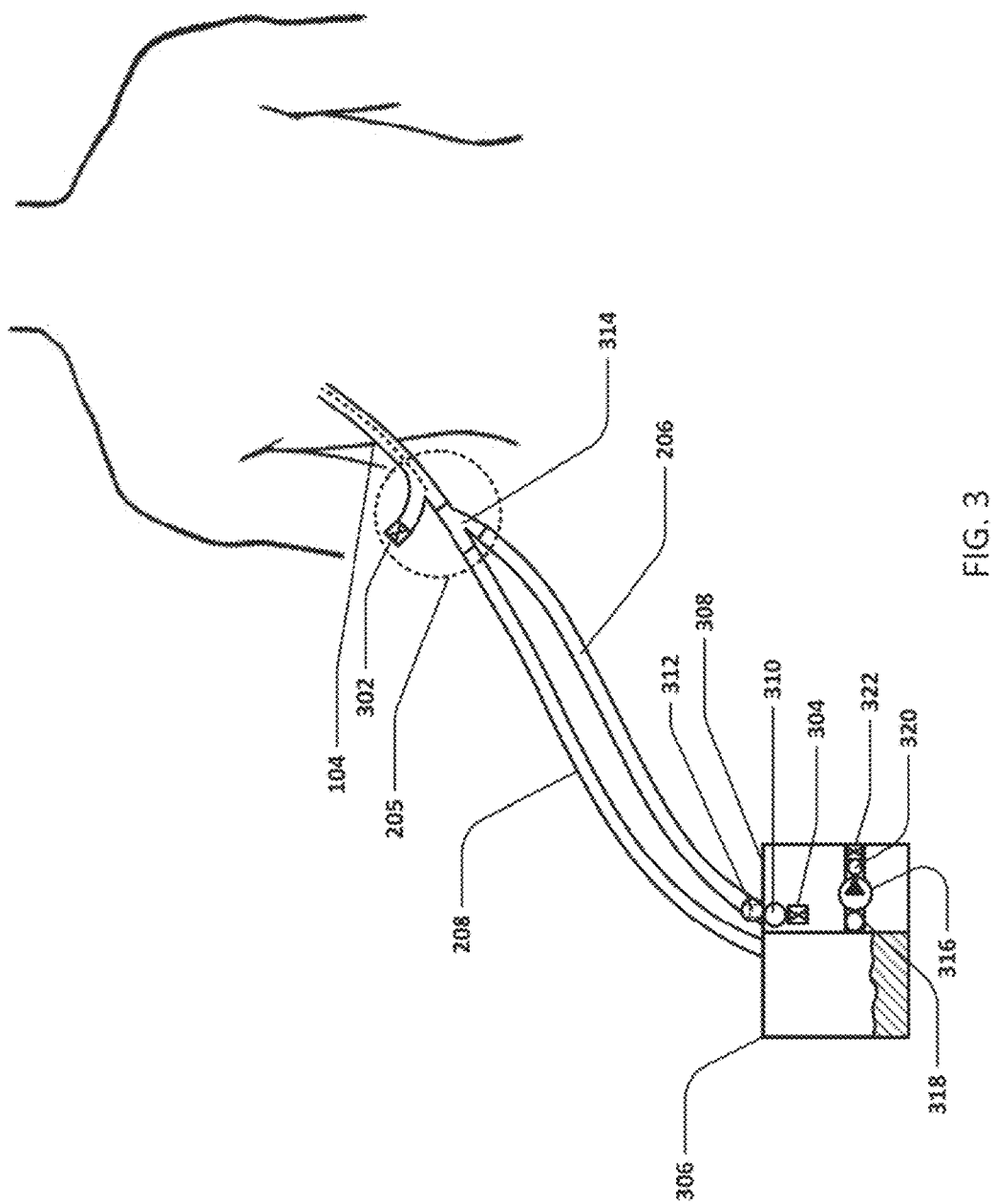
FIG. 3 shows an embodiment of the chest drainage system with an active drainage tube relief valve and a passive chest tube relief valve.
Figure 4:
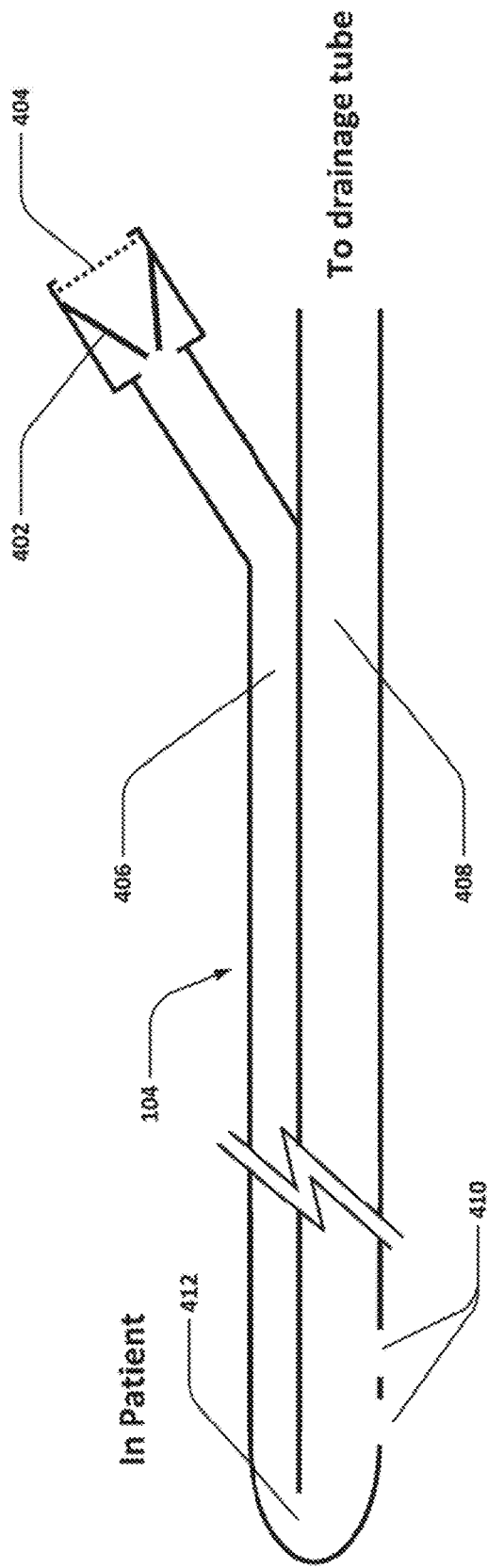
FIG. 4 shows an embodiment of the chest tube shown in FIG. 3

FIG. 3 shows an embodiment of the chest drainage system with an active drainage tube relief valve and a passive chest tube relief valve. Chest tube 104 is connected to drainage tube 208. Drainage tube relief lumen 206 is in fluid communication with both chest tube 104 and drainage tube 208. The connection among the 3 lumens—chest tube, drainage tube and drainage tube relief, occurs at tube-tube junction 205, which is at or near the chest tube/drainage tube junction. In some embodiments, the relief lumen may connect to the drainage tube or chest tube at a different location. The chest tube, drainage tube and drainage tube relief lumen may be connected with connection barb 314. Chest tube relief valve 302 may be incorporated into the chest tube, or a separate adapter designed to connect to the chest tube, for example, into connection barb 314. In this embodiment, the chest tube has at least two lumens, as shown in FIG. 4. Pressure sensor 310, drainage tube relief lumen valve 304, and filter/vent 312 are in fluid communication with drainage tube relief lumen 206. Controller 308 includes pump 316, pressure sensor 310, drainage tube relief valve 304, filter/vent 312, and fluid reservoir (or suction canister) 306, which is in fluid communication with drainage tube 208.

Controller 308 may also include pressure sensor 318 on the canister side of the pump, in-line flow sensor 320 on either side of the pump, and/or one-way valve 322 on either side of the pump.

Pressure sensor 310 senses the pressure in tube-tube interface area 205 (via drainage tube relief lumen 206).

When the drainage tube is blocked or restricted, the pressure in the tube-tube interface area increases. When this pressure increases to a set pressure (generally, a negative pressure), controller 308 opens drainage tube valve relief 304 (which is normally closed) to allow filtered atmospheric pressure air to enter drainage tube relief lumen 206. This influx of air, in combination with the negative pressure in the drainage tube caused by pump 316, acts to clear the drainage tube of blockages/restrictions. Once the pressure in the tube-tube interface area returns to normal, and/or after a set time, the controller closes drainage tube relief valve 304. Alternatively, the drainage tube valve may be a passive valve set to open and close at set pressures.

The monitor/controller may monitor pressure in the drainage tube relief lumen and may pull additional suction in the fluid reservoir/suction canister as needed to maintain the suction pressure in the proper range at the tube-tube interface area. For example, when the desired pressure is set to −20 cmH2O, the monitor may activate the suction pump to keep the pressure at the tube-tube interface area between −15 cmH2O and −25 cmH2O or between −18 cmH2O and −22 cmH2O. In another embodiment, the monitor may activate the pump and drainage tube relief valve 304 at regular temporal intervals as a preventative measure to clear any pooled liquid from the drainage line. This is done by the controller activating suction pump 316 while simultaneously opening drainage tube relief valve 304 to allow air to sweep accumulated liquid into the suction canister via the drainage tube.

The chest tube may become blocked or restricted. To clear restrictions, the suction magnitude applied by the controller to the drainage tube and experienced by the tube-tube interface may be increased. When the pressure in the tube-tube interface reaches a set low level, chest tube relief valve 302 opens and allows filtered atmospheric air to enter the relief lumen of the chest tube (see FIG. 4 for detail). This influx of air, in combination with the negative pressure in the drainage tube and tube-tube interface area caused by pump 316, acts to clear the chest tube of blockages/restrictions. A passive valve is shown here, although an active valve, controlled by the controller, may be used. Alternatively, a valve which is operated manually, may be used. Any of the operations disclosed herein which may be controlled by the controller, may alternatively be controlled passively, or manually. For example, valve functions, suction functions, etc.

The chest tube relief valve may have a different opening pressure and closing pressure. For example, the chest tube relief valve may open at a higher pressure differential (i.e. a more negative pressure in the tube-tube interface area), and close at a lower pressure differential. This allows the valve to stay closed until a clear chest tube blockage is present and to minimize the flow resistance of the valve. Once the valve is open, this allows the valve to stay open to completely clear the chest tube blockage, even if the tube-tube interface area pressure increases so that the pressure differential across the chest tube valve drops below the valve opening pressure. In other words, the pressure within the tube-tube interface area may be more negative when a chest tube blockage is created, but less negative, as the chest tube blockage is being cleared.

FIG. 3 shows one chest tube in use with the chest drainage system, but in some embodiments, more than one chest tube may be used with the system. Each chest tube may have its own drainage lumen and relief lumen and valve.

FIG. 4 shows an embodiment of the chest tube shown in FIG. 3. Chest tube 104 includes drainage lumen 408 and chest tube relief lumen 406 incorporated into the chest tube. Chest tube relief valve 402 and filter/vent 404 are also shown in fluid communication with chest tube relief lumen 406, which is in fluid communication with chest tube drainage lumen 408 via opening 412. Drainage openings 410 allow fluid from the chest cavity to enter the chest tube and drain through chest tube drainage lumen 408.

During successful chest drainage, chest tube relief valve 402 is in the closed position. In this position, fluid draining from the chest generally does not enter chest tube relief lumen 406 because of the fluid column in the chest tube relief lumen. A smaller diameter chest tube relief lumen may help prevent fluid from entering the chest tube relief lumen. The pressure in chest tube relief lumen 406 is slightly negative during chest tube drainage due to the negative pressure exerted by the pump on the drainage line, the chest tube drainage lumen, and to some extent, the chest tube relief lumen. The chest tube may become blocked or restricted, because of blood clots etc. To clear them, the monitor may apply additional suction to decrease the pressure in the chest tube drainage lumen, and ultimately, the chest tube relief lumen, to a more negative pressure. As this negative pressure drops below a set valve opening pressure, chest tube relief valve 402 opens, allowing atmospheric (i.e., more positive pressure) to enter the system. This, in combination with the negative pressure exerted on the drainage lumen, clears the chest tube drainage lumen. Once the pressure in the chest tube relief lumen increases back to a set valve closing pressure, chest tube relief valve 402 closes and normal drainage continues. The chest tube relief valve opening pressure may be different than the chest tube relief valve closing pressure to allow drainage of the chest tube. For example, the chest tube relief valve opening pressure may be at a higher pressure than the chest tube relief valve closing pressure.

For example, the chest tube relief valve may open when the pressure differential across the valve is about −10 cmH2O, about −20 cmH2O, about −30 cmH2O, about −40 cmH2O, about −50 cmH2O or as even high as about −100 cmH2O. Or for example, the chest tube relief valve may open when the pressure differential across the valve is within a range of about −10 cmH2O to about −20 cmH2O, or within a range of about −20 cmH2O to about −30 cmH2O, or within a range of about −30 cmH2O to about −30 cmH2O, or within a range of about −40 cmH2O to about −40 cmH2O, or within a range of about −50 cmH2O to about −100 cmH2O.

The chest tube relief valve may close at the same range, or at a lower differential than the opening pressure. For example, the chest tube relief valve may close at a pressure differential of about to 0 cmH2O, about −5 cmH2O, about −10 cmH2O, about −15 cmH2O, or about −20 cmH2O. Or for example, the chest tube relief valve may close at a pressure differential range of about to 0 cmH2O to about −5 cmH2O, or a range of about −5 cmH2O to about −10 cmH2O, or a range of about −10 cmH2O to about −15 cmH2O, or a range of about −15 cmH2O to about −20 cmH2O.

The chest tube relief valve may take a variety of known forms, including but not limited to a check valve, umbrella valve, ball valve, Belleville valve, X-fragm valve, cross-slit valve, or dome valve. The valve system preferably has a filter in place to prevent the entrance of bacteria or viruses from the atmosphere into the patient.

In another embodiment of the chest tube, chest tube relief valve is active, not passive, and is controlled by the controller.

In some embodiments of the chest tube, chest tube relief valve is incorporated into the chest tube. In some embodiments, the chest tube relief valve is incorporated into a connecter which is connected to the chest tube. In some embodiments of the chest tube, both the chest tube relief lumen and the chest tube relief valve are incorporated into a connecter which may be connected to a chest tube.

In some embodiments, chest tube relief valve 402 takes the form of a magnetic check valve that has a substantial difference in the pressure differential required to open the valve, and the pressure differential required to keep the valve open (or close the valve), thereby amplifying the toggling effect of the valve. This is preferable to increase the effectiveness of the clog clearance cycle, because it allows for a greater pressure differential when the air is sweeping the drainage lumen via the relief lumen than if the valve opened and closed at the same pressure. The valve is normally closed in order to maximize drainage of liquid as it enters the chest tube and to reduce the need for continuous pumping. FIG. 5 shows a magnetic embodiment of the chest tube valve. The magnetic chest tube valve includes housing 502, filter 504, ferrous plate 506, gasket 508, magnet 510, seal plate 512, and positioning lip 514. When the pressure differential across the valve increases above a desired threshold, for example −50 cmH2O, the force caused by the pressure differential is enough to overcome the magnetic force between the magnet and the ferrous plate, thereby moving the two away from each other. Once the magnet and the ferrous plate move away from each other, the magnetic force rapidly diminishes, as the magnetic force is proportional to $(1/r^3)$. As a result, the amount of pressure necessary to keep the valve open is less than the pressure that was required to open it. This second pressure value, for example −10 cmH2O, is determined by the maximum distance the magnet and seal plate can travel away from the ferrous plate, which is in the exemplary embodiment shown in FIG. 5 determined by positioning lip 514 in the housing that sets this distance.

Figure 6A:
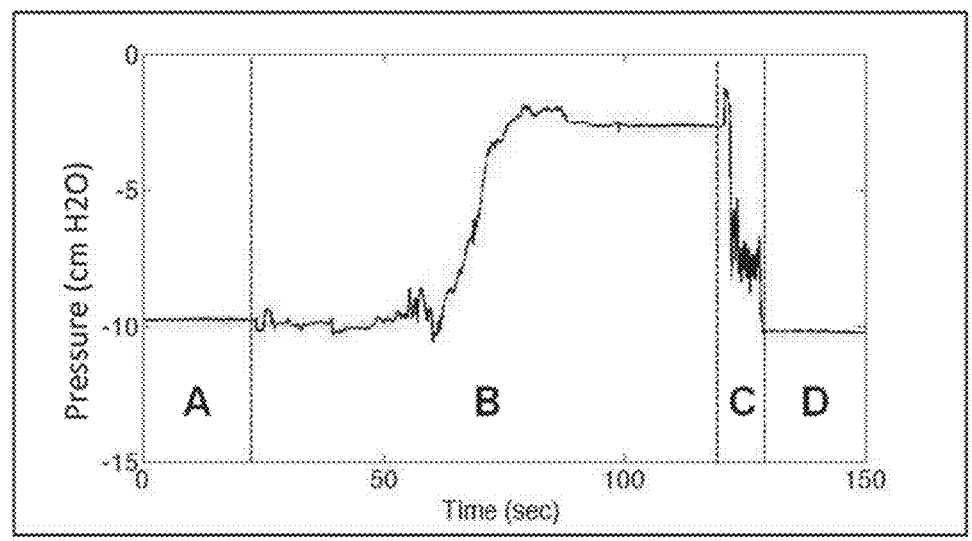
FIG. 6A shows the chest drainage system's ability to detect and clear pooled liquid in the drainage tube.

FIG. 6A shows the chest drainage system's ability to detect and clear pooled liquid in the drainage tube. In section 'A', a −10 cmH2O vacuum is properly transmitted to the chest. In section 'B', liquid begins to pool in the bottom of the tube, resulting in a decreased negative pressure (or an increased pressure). If unresolved clinically, drainage would be impeded. However, in section 'C' the drainage tube relief valve is opened and the liquid is flushed into the drainage container, resulting is restoration of proper suction in Section 'D', as well as proper negative pressure as measured. The valve is closed after normal drainage/pressures have been restored. In this example, the pressure is measured at the tube-tube interface area, however pressure may be measured in other and/or additional locations in the system. For example, pressure may be measured at or near the chest or chest tube and also at or near the suction device, and the differential pressure measurement may be used to detect flow impediments or pooling or clotting of blood/fluid.

The controller can identify impediments to fluid drainage via a measured absolute pressure, change in pressure, pressure differential between or among 2 or more locations, or at one location. When an impediment to fluid drainage is identified, an alarm may sound and/or the controller may initiate clearing procedures, including opening and/or closing valve(s) in the chest drainage system, as described elsewhere herein. The negative pressure in the drainage tube may be increased, or changed in other ways, such as pulsed, reversed etc.

For example, if pressure measured at the tube-tube interface area is reading around −10 cmH20 to around −20 cmH20 and the reading changes to zero to −5 cmH20, the controller may open the drainage tube valve to filtered atmospheric air. The controller may leave the valve in this position for a set period of time, say 5-10 seconds or 10-30 seconds and then may return the valve to its regular position. Alternatively, the controller may close the valve when a set pressure is measured at the tube-tube interface area or elsewhere. The controller may then check the pressure readings and if they have returned to normal, do nothing more. If they have not returned to normal, indicating a blockage or slowing condition is still present, the controller may repeat the clearing procedure. This may be done repeatedly until the tubing is cleared. Alternatively or additionally, the procedure may change if repeat clearings are necessary. For example, the magnitude of negative pressure used by the suction device to clear the tubing may be increased, and/or the negative pressure may be pulsed. The clearing procedure may be performed in response to the pressure readings and/or it may be done automatically on a periodic basis.

Figure 6B:
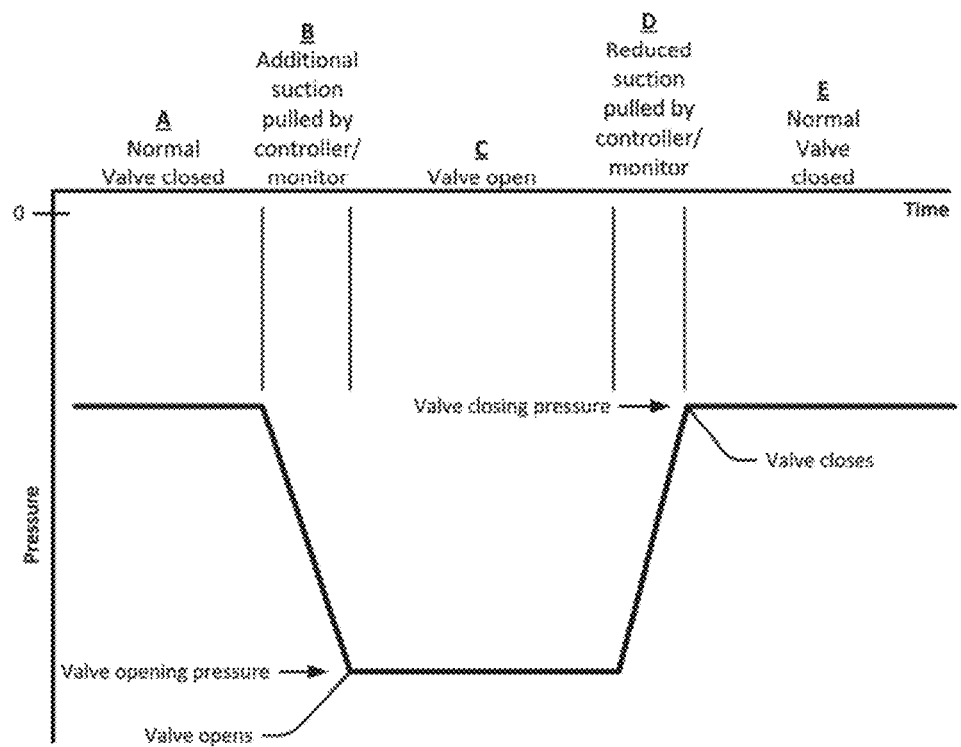
FIGS. 6B-6F show the chest drainage system's ability to detect and clear pooled liquid in the chest tube.

FIGS. 6B-6F shows the chest drainage system's ability to detect and clear pooled liquid in the chest tube. FIG. 6B shows the pressure in the chest drainage system over time. This pressure may be measured by the controller, preferably via the drainage tube relief lumen, but can alternatively be measured elsewhere.

Section A of FIG. 6B shows normal drainage at a negative pressure, created by the suction pump of the chest drainage system. Section B shows additional suction being pulled by the controller/monitor. This additional suction may be pulled periodically, or may be pulled based on pressure readings in the system. For example, additional suction may be pulled when the presence of tidal oscillations is no longer detected in the drainage system by the controller. The additional suction transfers negative pressure to the drainage tube drainage lumen, the chest tube drainage lumen, and ultimately the chest tube relief lumen and chest tube relief lumen valve. When the pressure differential across the chest tube relief lumen valve reaches the valve opening pressure, the chest tube relief lumen valve opens. The valve may open automatically if the valve is passive, or by the controller, if the valve is active. Section C shows the pressure when the valve is open. The valve may remain open for a set period of time. Alternatively, the valve may remain open until the controller senses that the clog has been cleared. The negative pressure, or suction, within the system may remain steady during this phase, as shown in FIG. 6B, or the negative pressure may become more negative, as shown in FIG. 6C, or the pressure may become less negative, as shown in FIG. 6D.

Section D shows the magnitude of the negative pressure decreasing as a result of a reduction in suction being pulled by the controller/monitor. When the pressure in the system reaches the valve's set closing pressure, the valve closes (or is closed) and fluid drainage continues in a normal manner. The valve closing pressure may be at a lower magnitude negative pressure than that of the opening pressure, as shown here. The valve closing pressure may be at or near normal drainage negative pressure.

Figure 6C:
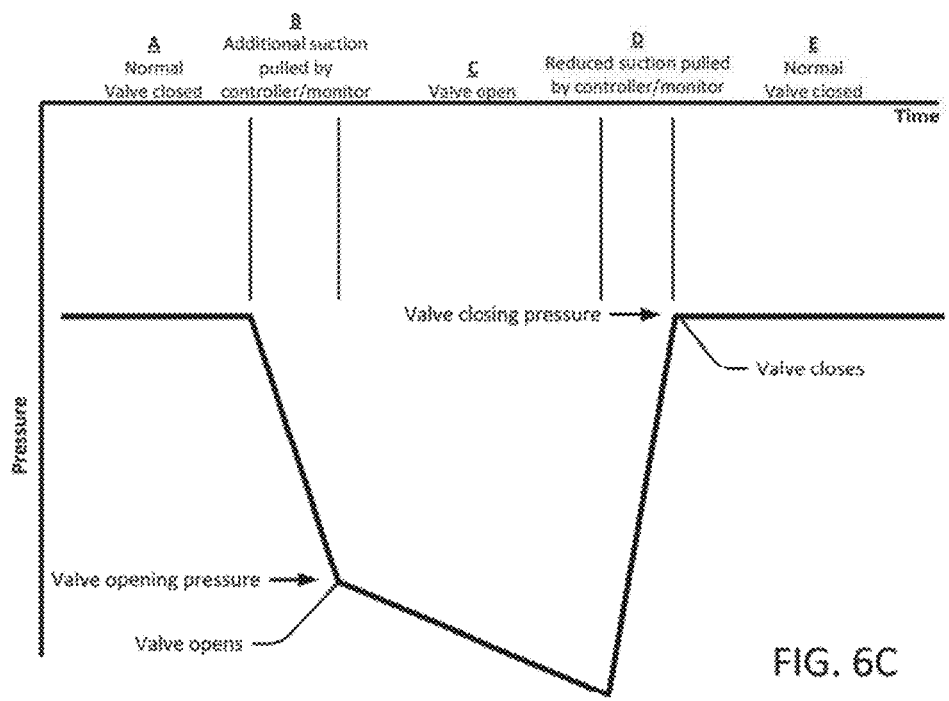
Figure 6D:
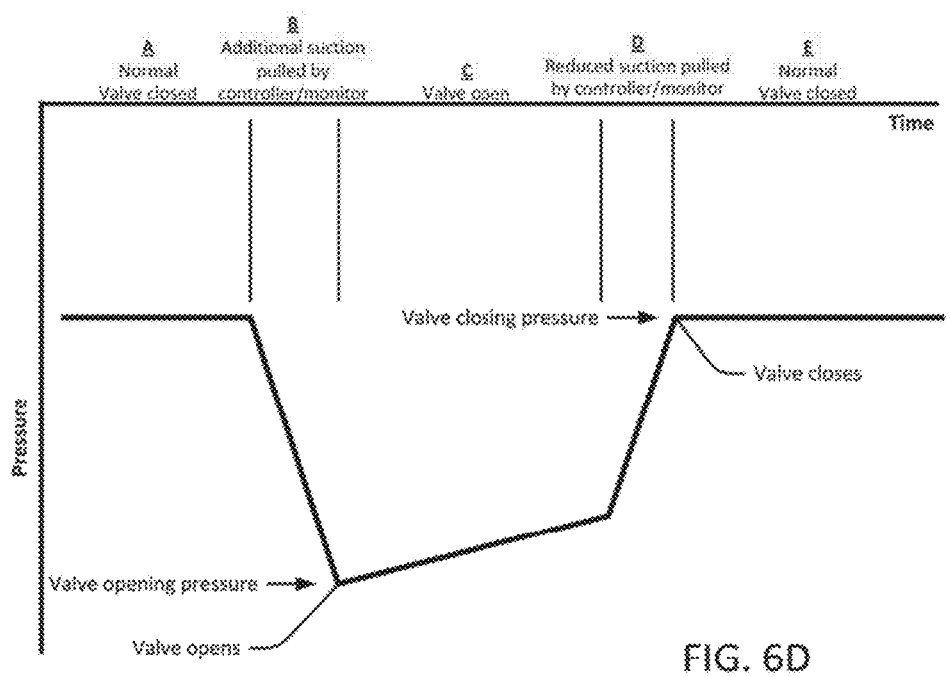

FIGS. 6B-6D show different slopes of negative pressures in different situations. In FIG. 6B the rate at which air is entering the system via the chest tube relief lumen valve is the same as the rate at which the suction pump is draining the system during the open valve section C. In FIG. 6C, the rate of drainage is higher than the rate of air entering the system. In FIG. 6D, the rate of drainage is lower than the rate of air entering the system. The slope of the pressure curve in section C may be controlled by the controller and the amount of suction that it is pulling.

Figure 6E:
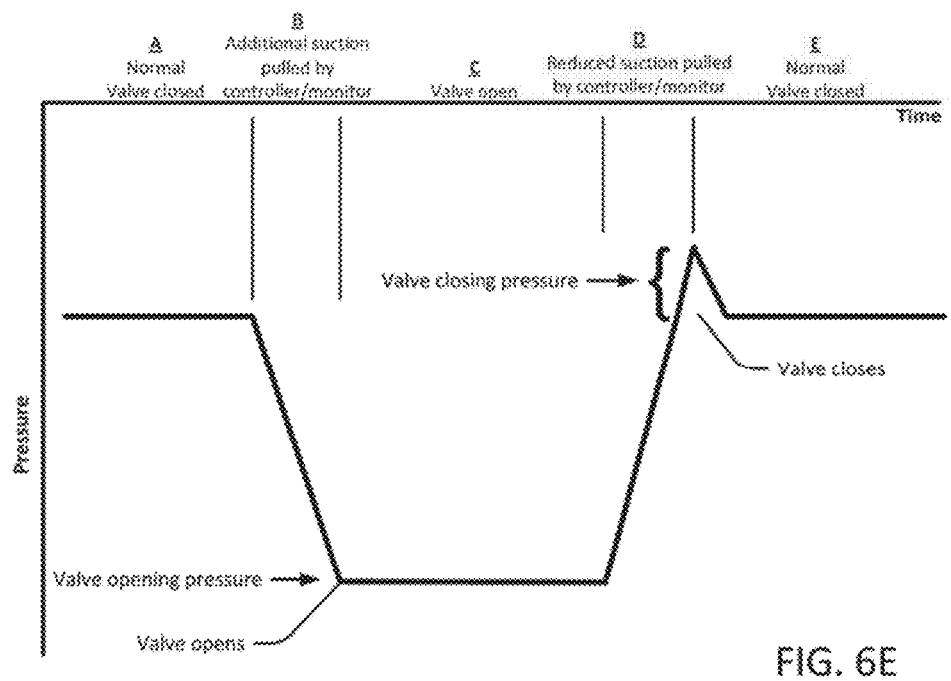

FIG. 6E shows an embodiment where the controller "overshoots" the normal draining suction pressure to close the chest tube relief lumen valve. The valve closing pressure in this embodiment may be around the normal draining pressure, or it may be at a less negative pressure (lower differential pressure).

Figure 6F:
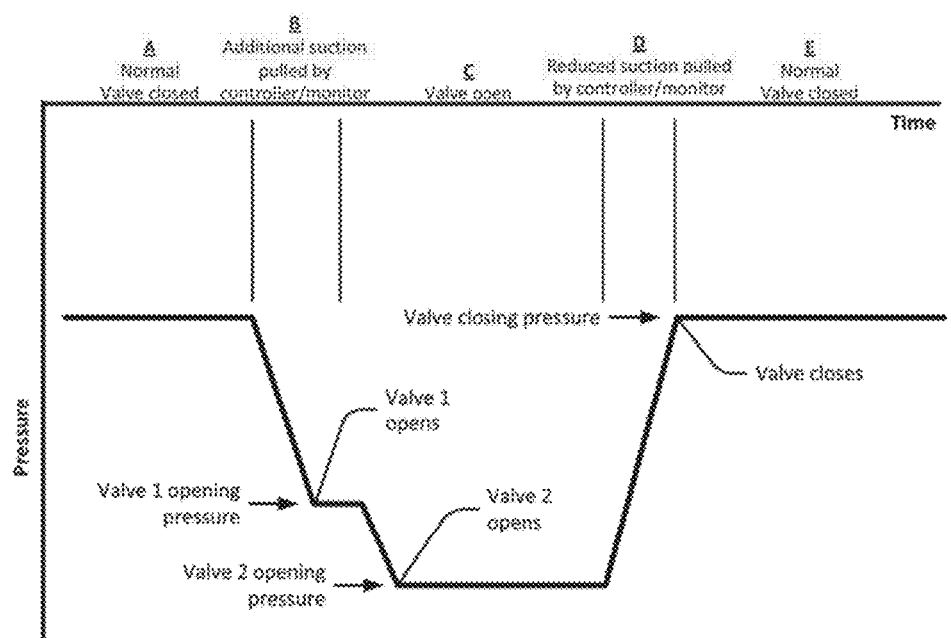

FIG. 6F shows an embodiment where there is more than one chest tube. In this embodiment, the first chest tube relief valve opens when the pressure in the system reaches valve 1 opening pressure. It may be necessary to increase the magnitude of the negative pressure in the system further to open the second chest tube relief lumen valve. This is shown as valve 2 opening pressure on the graph. There may be 1, 2, or more valve opening pressures depending on how many chest tubes are used on a single patient. The closing pressures of the multiple chest tube relief valves may be the same, or they may be different. The ability to detect the opening of the valves may be useful to determine whether one or more of the chest tubes is clogged, in which case an alarm or notification may be provided.

In some embodiments, the chest drainage system may include a pH sensor. Post-surgery infection and empyema are of particular concern to clinicians. The pH of fluid drained from the body can be useful in diagnosing these, and other, conditions. To aid in the diagnosis, the chest drainage system may include a pH monitor in the controller, with a sensor in the reservoir, in the tubing, the pump, the valve device, or anywhere in the system. The results may be displayed on the display device. The system may also include a sampling port to sample the fluid drained from the chest. The system may also include an infusion port to infuse an additive into the drainage fluid. These ports may be in the reservoir, tubing, controller, valve device, or elsewhere in the system, for example at the chest tube/drainage tube interface.

In an embodiment of the device shown in FIG. 3 (or other embodiments disclosed herein), the system is capable of measuring the flow rate of air evacuated from the canister/reservoir, in addition to pressure in the canister and pressure in the drainage tube relief lumen. Evacuation flow rate may be used to determine the presence and rate of an air leak from the chest cavity. The evacuation flow rate necessary to maintain the system at the prescribed suction level is equivalent to the flow rate of air entering the system (air leak), as the flows of air into and out of the system must be equal in the presence of steady pressure. Evacuation flow rate may be determined by the flow rate of the air being evacuated from the canister via the integrated suction pump and the volume of liquid in the canister. These parameters may be tracked over time by the controller to determine chest air leak presence and other parameters, such as air leak rate and changes to the air leak rate over time. Flow rate measurements are preferably made with any number of off-the-shelf sensitive air flow sensors that are known in the art. Flow rate may alternatively or additionally be measured by measuring the revolutions of the pump motor necessary to keep the suction at a prescribed level via a tachometer. Collected fluid volume measurements are preferably made with a non-contact capacitive sensor, but may alternatively be made with optical sensors, pressure sensors, acoustic (such as ultrasonic) sensors, or any other liquid level sensing methods known in the art. In some embodiments, a capacitive sensor is mounted on the inside of the suction monitor and may use out-of-phase techniques to reduce interference from within the proximity, such as a human hand near or in contact with the container. Such a technique uses a level electrode, reference electrode, environment electrode, ground electrode, and two shield electrodes. In another embodiment, a compliant layer of material is present on either the suction monitor or the suction canister in the area of the capacitive electrode in order to minimize or eliminate any air gaps between the suction monitor and the suction canister.

Drainage fluid volume may be measured and tracked in the presence or absence of air leak determination.

Example of Data Processing System

Figure 7:
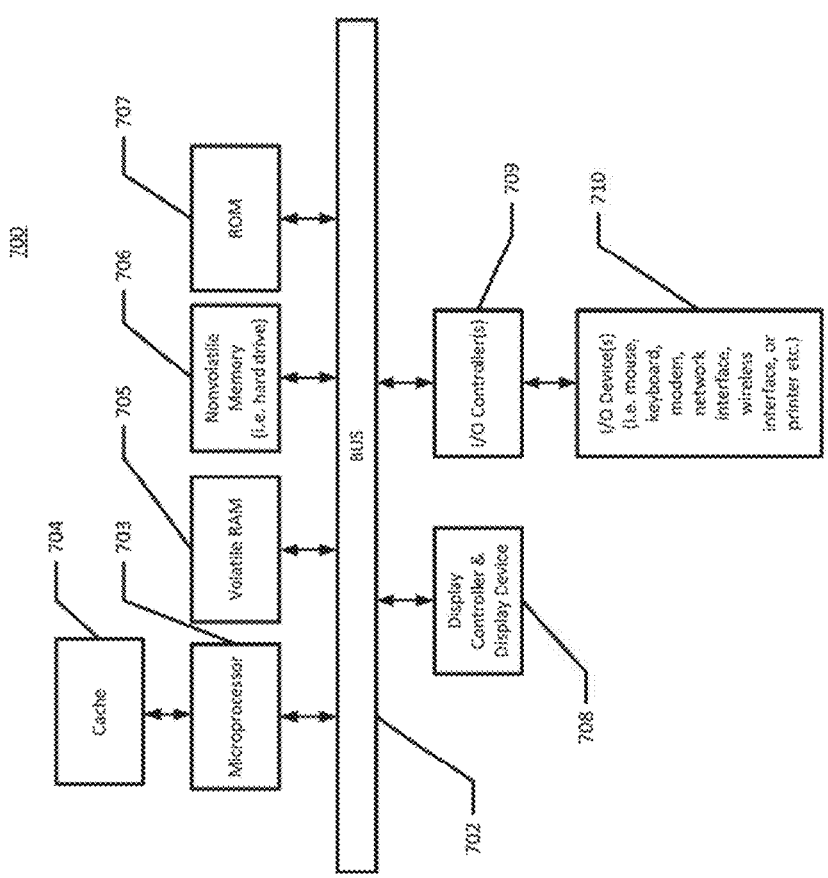
FIG. 7 is a block diagram of a data processing system.

FIG. 7 is a block diagram of a data processing system, which may be used with any embodiment of the invention. For example, the system 700 may be used as part of a controller/monitor. Note that while FIG. 7 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 7, the computer system 700, which is a form of a data processing system, includes a bus or interconnect 702 which is coupled to one or more microprocessors 703 and a ROM 707, a volatile RAM 705, and a non-volatile memory 706. The microprocessor 703 is coupled to cache memory 704. The bus 702 interconnects these various components together and also interconnects these components 703, 707, 705, and 706 to a display controller and display device 708, as well as to input/output (I/O) devices 710, which may be mice, keyboards, modems, network interfaces, printers, and other devices which are well-known in the art.

Typically, the input/output devices 710 are coupled to the system through input/output controllers 709. The volatile RAM 705 is typically implemented as dynamic RAM (DRAM) which requires power continuously in order to refresh or maintain the data in the memory. The non-volatile memory 706 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 7 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 702 may include one or more buses connected to each other through various bridges, controllers, and/or adapters, as is well-known in the art. In one embodiment, the I/O controller 709 includes a USB (Universal Serial Bus) adapter for controlling USB peripherals. Alternatively, I/O controller 709 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Various Embodiments

In one embodiment of the chest drainage system, a balloon or balloons may be used to clear the chest tube of clogs. In the normal drainage configuration, the balloons are deflated to minimize the space they occupy within the chest tube lumen and maximize drainage. For some examples, see PCT application PCT/US15/52960 which is incorporated herein by reference in its entirety. Clogs may be detected by sensing pressure and/or pressure changes within the system. Clogs may be cleared when they are sensed, or on a timed interval bases. To clear clogs, the balloon(s) are inflated to urge clogs through the chest tube and toward the suction canister. The balloons may be compliant or non-compliant, or a hybrid of the two. Compliant balloons may be used to conform to the shape of the inner chest tube lumen, which may be used to provide a sealing of the chest tube if the drainage tubing is subsequently flushed with fluid (gas or liquid) toward the suction canister. This seal prevents the flushing fluid from entering the chest cavity. Alternatively, non-compliant balloons may be used to generate significant forces in order to compress and clear clogs. This is especially useful with robust, or firmer, clogs.

Figure 8:
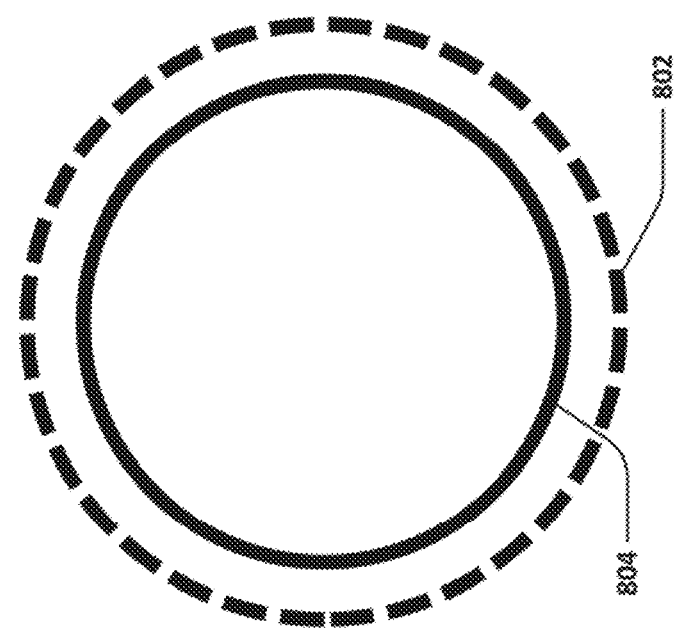
FIG. 8 shows a balloon with a compliant layer and a non-compliant layer.
Figure 9:
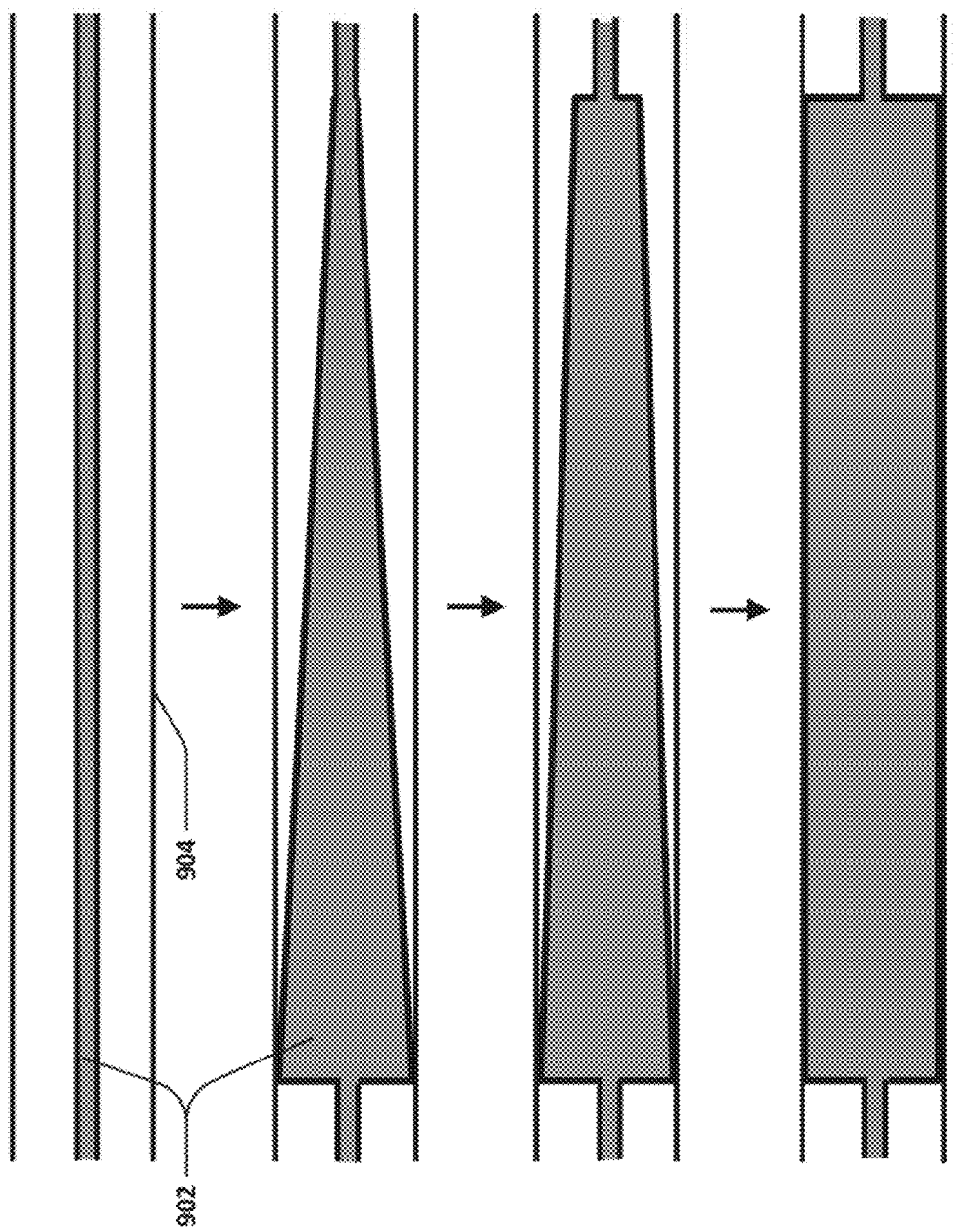
FIG. 9 shows a tapered balloon.

A combination of these balloons may be used to achieve both objectives. For example, a non-compliant balloon may be coupled with a compliant layer as illustrated in FIG. 8. FIG. 8 shows a balloon with compliant layer 802 and non-compliant layer 804. In another embodiment, the balloons may inflate directionally via valves between the balloons, or may each have separate inflation lumens to inflate them each sequentially. Alternatively, the balloons may be tapered in shape and semi-compliant such that they directionally inflate against the inner chest tube lumen wall as they are inflated. This is shown in FIG. 9 which shows balloon 902 as it is inflated against the inside of the drainage lumen of chest tube 904.

The balloon may also inflate directionally in an accordion-like fashion, with the shape of the balloon and/or pleats to control the direction of inflation, as illustrated in FIG. 10, which shows balloon 1002 and the inner wall of the drainage lumen of the chest tube 1004.

In another embodiment, the balloon may be built into the chest tube itself, such as a coextruded inner wall that compresses inward as it inflates or expands to fill the chest tube drainage lumen, as illustrated in FIGS. 11A and 11B. The figures show deflated balloon 1102, inflated balloon 1102', and chest tube drainage lumen 1104. FIG. 11A shows a concentric configuration where FIG. 11B shows an offset configuration.

In another embodiment, a balloon may be used to deliver energy to the chest tube and to any clogs within the drainage lumen of the chest tube to break up or dissolve the clogs. This may include thermal energy, light energy, acoustic energy, or microwave energy. In some embodiments, the balloon may have a reinforcing structure, such as a Nitinol coil, to: increase the compression force against clogs, act as a chopping/breaking mechanism, and/or act as a spring to control inflation direction/shape as discussed above. Balloon inflation fluid may be a gas or a liquid. The inflation fluid may be sterile. If sterile, for example by delivering the fluid across a sterile membrane (for example one with pore size of 0.2 um) or storing the fluid in a sterile reservoir for inflation and deflation cycles, illustrated as 1202 in FIG. 12.

Another embodiment of the drainage system makes use of a magnetic guidewire to clear the chest tube of clogs. The guidewire is activated by enabling an external electromagnet such that the guidewire intermittently moves in and out of the chest tube, in similar fashion to a solenoid. This embodiment is illustrated in FIG. 13, which shows magnetic guidewire 1302 and electromagnet 1304, as well as clog moving feature 1306 at the end of the guidewire.

Other embodiments of the chest drainage system prevent adherence of clogs to the chest tube wall. In one embodiment, vibration energy, such as ultrasonic energy, is used. In another embodiment, the chest tube is made from, or coated with, a material to prevent adherence, such as, PTFE. In another embodiment, adherence prevention is accomplished by reducing the viscosity of the clots using coatings or drugs such as heparin or a thrombolytic.

In another embodiment, a flushing mechanism is incorporated into a balloon at the patient end of the chest tube, such that once the balloon is fully inflated, a flush port is exposed to allow fluid to flush pooled liquid through the drainage tubing and into the suction canister, as illustrated in FIGS. 14A-14C. Balloon 1412 with flush port 1414 is shown in chest tube 1410. In one case, the flush port comprises microholes in the wall of the balloon. FIG. 14A shows the balloon deflated. FIG. 14B shows the balloon partially inflated. FIG. 14C shows the balloon fully inflated and shows the flush fluid direction within chest tube 1410.

In another embodiment, multiple valves, such as balloon valves, are used to seal, or essentially seal, the chest tube so that suction can be applied to the drainage tubing and/or the chest tube to clear clots/blockages. The balloon(s) may also provide positive pressure to the chest tube and/or drainage tubing to flush pooled liquid into the collection reservoir while sealing the chest cavity from the positive pressure, as illustrated in FIGS. 15A-D. FIG. 15A shows valve device 1500 with inner lumen 1502. The valve device may be part of the chest tube, or the drainage tube, or may be a separate device, preferably between the chest tube and the drainage tube. Balloon valves 1504 and 1506 are shown, in addition to opening/port 1508. Lumen 1502 of the valve device is shown open in FIG. 15A. The valve device may operate with the following steps:

Step 1: Lumen 1502 is closed to the drainage tube by inflating (or closing) balloon valve 1506. The lumen remains open to the chest tube. A vacuum is exerted on the chest tube lumen by applying a negative pressure to lumen 1502 via opening 1508. The negative pressure applied to the chest tube lumen is used to clear any blockage within the chest tube. This step is shown in FIG. 15B.

Step 2: Balloon valve 1506 is deflated (or opened) and balloon valve 1504 is inflated (or closed). Positive pressure is applied to lumen 1502 via opening 1508. This serves to force the blockage down through the drainage tube, without exerting any positive pressure within the chest cavity. This step is shown in FIG. 15C.

Step 3: Balloon valve 1504 is deflated (or opened) allowing chest drainage to proceed normally. A valve and/or filter may be used in fluid communication with opening 1508. This step is shown in FIG. 15D.

These steps may be repeated multiple times to clear the chest tube. The repetitions may be based on a pre-set schedule, or they may be set based on whether the existence of a chest tube blockage is sensed.

In some embodiments, the patient end of the chest tube is vented to atmosphere, for example, via a chest tube relief lumen, to allow sterile air to purge clogs from the chest tube during step 1.

Another embodiment of the drainage system makes use of a flush port for manual intermittent flushing of the chest tube and drainage line, as shown in FIG. 16A. Chest tube 1602 includes flush port 1604 and flush opening 1606. In one embodiment, the flush port is swabbable to ensure sterility prior to flushing. In one embodiment, the drainage tubing is clamped and the flushing fluid is infused into the chest tube and into the pleural cavity, but subsequently drained once the drainage tubing is unclamped and the chest tube patency is restored. In one embodiment, the flush port connects to a lumen, such as a chest tube relief lumen, that terminates at the patient (proximal) end of the chest tube such that the flushing fluid is infused through the chest tube toward the drainage tubing and suction canister with the drainage tubing unclamped by. sealing the chest tube prior to flushing. This may be accomplished by balloon 1608, or other valve, located within the chest tube lumen, as shown in FIG. 16B. The flushing fluid may be air, water, saline, heparin, a thrombolytic agent such as tissue plasminogen activator, or any other suitable fluid.

Another embodiment of the chest drainage system monitors physiologic parameters of interest. In one embodiment, pressure is monitored. For example, internal chest pressure may be sensed and monitored to ensure the applied negative and/or positive pressure is being properly transmitted to the chest cavity. Or, for example, pleural and/or pericardial pressures may be monitored to track healing. Or, for example, differential pressure between the distal and proximal ends of the chest tube may be monitored to ensure chest tube patency. Or, for example, the pressure at the distal (non-patient) end of the chest tube, for example at the proximal and/or distal end of the drainage tubing or collection canister, may be monitored for tidal oscillations, which are indicative of tube patency.

In some embodiments, the volume and/or flow rate of the drained chest fluid (either gas, liquid, or both) may be measured and monitored over time. In another embodiment, the volume and/or flow rate of an air leak (from the patient's lung) is measured to monitor wound healing. In another embodiment, pH of the drained fluid is measured to monitor for infections. Additional parameters, such as conductance, spectroscopic signatures, protein content, and specific gravity of the drained fluid may also be measured to monitor patient recovery. Any of these measurements may be one time measurements or measurements made over time. For measurements made and collected over time, the controller may analyze these data for trends. These data may be integrated with the hospital's electronic medical record system (either communicated to, or data may be obtained from) and/or displayed on a screen on the device or on a connected monitor, which may be connected either by wire or wirelessly. In some embodiments, alarms or notifications may be activated by the controller when the parameters surpass certain thresholds, which may be preset or set by the user. These may be visual and/or audible alarms or notifications. These data may also provide input to the line-purging and clog-clearing functions of the device, such that, for example, line purging is activated when the suction at the chest drops below a certain level, or clog clearing is activated when tidal oscillations are diminished.

Another embodiment of the drainage system makes use of safety features to prevent dangerous pressures from occurring when inflating the balloons or flushing the chest tube and/or drainage tubing as described herein. In one embodiment, the pumps used to inflate or flush are connected to safety valves with crack pressures that are in the range considered to be physiologically safe, for example preventing suction below about −20 cmH2O, −40 cmH2O, or −70 cmH2O. The pumps may be connected to pressure sensors with control systems to turn off the pumps if pressures are outside of the safe range.

Another embodiment of the valve device includes a suction reservoir to provide additional suction to clear potential clogs from the chest tube, as shown in FIGS. 17A-17D. Shown in these figures is valve device 1700, which may be placed between the chest tube and the drainage tube, or may be integrated into the drainage tube, or the chest tube. Valve device 1700 includes inner lumen 1716 with lumen port 1706, chest-side valve 1702 with chest-side valve port 1704, drainage-side valve 1712 with drainage-side valve port 1714, chamber 1710 with chamber port 1718 and within the chamber is expandable valve 1708.

In this embodiment, expandable valve 1708 is expanded by pulling suction (or applying negative pressure) within chamber 1710 via chamber port 1718. In this way, expandable valve 1708 can generate additional suction within the chest tube. This suction is directed by additional valves 1702 and 1712, illustrated as inflatable/deflatable balloon valves to temporarily seal lumen 1716. The sequence of events is:

Step 1: Lumen 1716 is sealed via valve 1712 to seal off chest tube from the drainage tube. This is done by applying pressure to valve 1712 via port 1714, inflating valve 1712 to close off lumen 1716 on the drainage tube side of valve device 1700. This is shown in FIG. 17B.

Step 2: Additional suction is applied to the chest tube by expanding valve 1708. This is done by applying suction to chamber 1710 via port 1718. This is also shown in FIG. 17B. This applies additional suction to the chest tube, as indicated by the solid arrow in lumen 1716 in FIG. 17B.

Step 3: The chest tube side of the valve device is then sealed via valve 1702 by applying pressure to the valve via port 1704. This is shown in FIG. 17C.

Step 4: The drainage tube side of the valve device is then opened by releasing the pressure applied (or applying a vacuum) to valve 1712. Expandable valve 1708 is also returned to its neutral state by releasing the vacuum applied (or applying pressure) to chamber 1710 via port 1718. Port 1706 (also described herein as drainage tube relief lumen port) allows filtered atmospheric air to enter lumen 1716. The release, or pressurization, of expandable valve 1708 may be enough to flush the drainage lumen of any blockage, so that fluid again may drain normally into the collection reservoir. If necessary, additional pressure may be applied to lumen 1716 via port 1706 to flush the drainage tube. Alternatively or in addition, the negative pressure applied to the drainage tube may be increased (made more negative). This step is also shown in FIG. 17C.

Step 5: Valve 1702 is opened by releasing the pressure applied (or applying vacuum) via port 1704. Lumen 1716 is now fully open and drainage may resume as normal. This is shown in FIG. 17D.

These steps may be repeated as necessary to clear the drainage tube. They may repeat at a set time interval. They may repeat continuously until the drainage line is cleared. They may repeat only as necessary, when the drainage tube is blocked.

Port 1706 may be always open or may be controlled, for example by a solenoid, by the controller to open/close as needed. The lumen to port 1706 is also described herein as the drainage tube relief lumen.

All the ports shown in FIGS. 17A-17D may connect to lines which are controlled by the controller. The ports and/or lines may include filters/membranes to prevent contaminates from entering the system.

In some embodiments, chamber 1710 and valve 1708 are not used and the components of the steps associated with the chamber and chamber valve are not taken.

FIGS. 18A and 18B show a method of measuring air leak using the chest drainage system. If the chest tube and drainage tube are clear of blockages, pressure within the chest can be measured and monitored by the controller to calculate the rate of air leak. As shown in FIG. 18A, the chest may be sealed off from the drainage canister, for example, using drainage-side valve 1712, and pressure may be measured using a lumen in fluid communication with the drainage lumen, such as via port 1706, or any other lumen in fluid communication with the chest tube lumen, for example a chest tube or drainage tube relief lumen. When the chest tube is sealed off form the vacuum source, the negative pressure in the chest tube lumen can be measured by the controller, and will attenuate if the patient has an air leak. The attenuation can be measured by the controller over time and converted to a rate of air leak (mL/min). A graph of the pressure within the chest tube over time in the presence of an air leak is shown in FIG. 18B.

Figure 19:
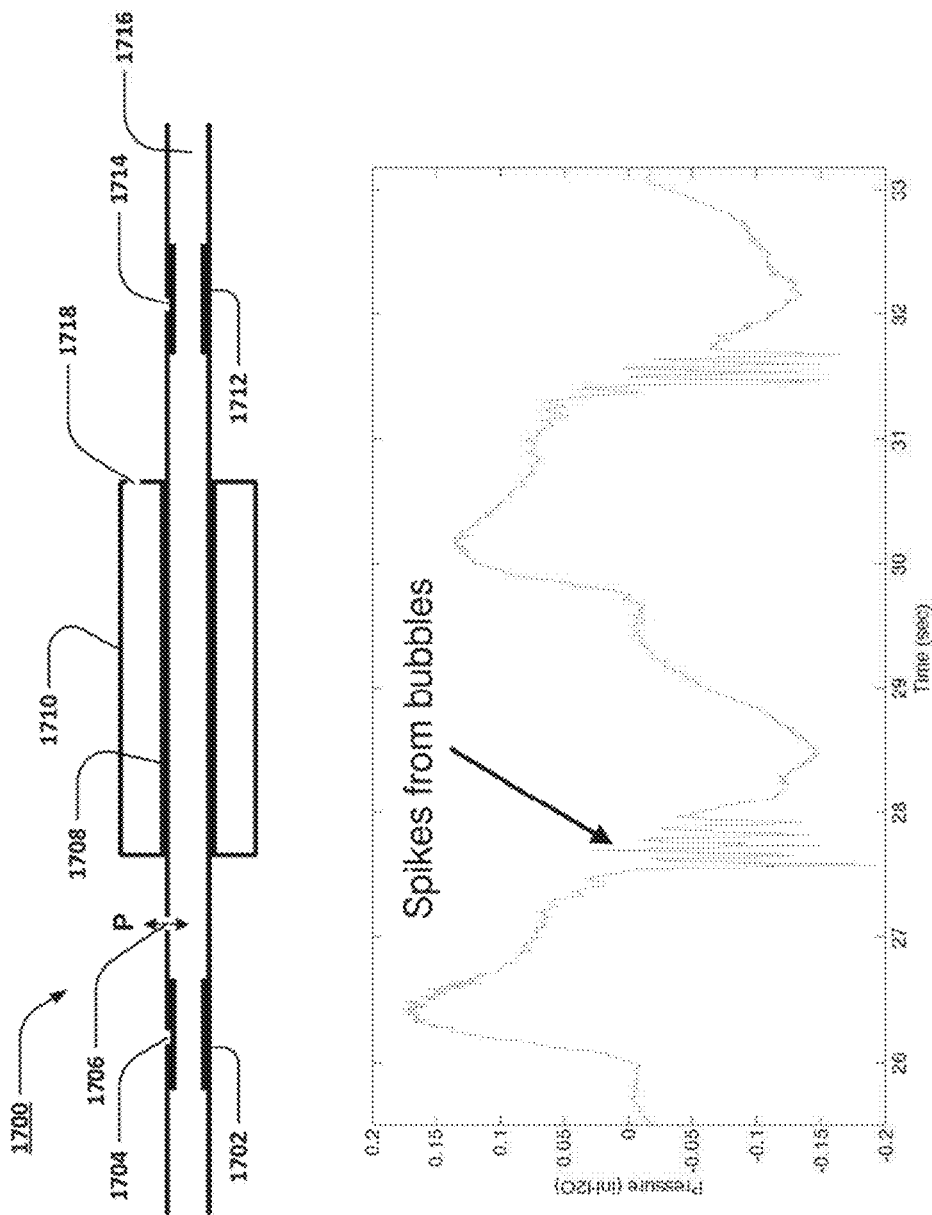
FIG. 19 show a method of measuring a chest/thoracic air leak using the chest drainage system.

An air leak may alternatively be measured by keeping both valves (1702 and 1712) open as shown in FIG. 19, and monitoring the pressure for spikes that result from bubbles in the water seal chamber in the suction canister. Pressure may be measured via opening 1706 or any other area in fluid communication with lumen 1716. In a preferred embodiment, this method makes use of a sensitive pressure sensor that is connected in line with a high-pass filter in order to make the spikes from bubbling easier to detect. The various methods of air leak detection described herein may be used independently or in combination.

In another embodiment of the device, clog detection is performed by comparing the pressure measured within the chest (via the chest tube relief lumen) and the pressure just distal to the chest tube (via the drainage tube relief lumen), i.e. in the tube-tube interface area. These pressures may be compared to one another, and when they differ by certain amount, for example 5 cmH2O, this is indicative of a clog in the chest tube. Alternatively, the pressure within the chest alone may be monitored, and when it increases by a certain amount, for example to above about 0 cmH2O, this may also indicate that a clog in the chest tube exists. When a clog is detected, for example by either of these methods, the controller may automatically activate any of the clog-clearing mechanisms described herein. Additionally, similar automation may be applied to the drainage line purging mechanism, by monitoring the pressure distal to the chest tube (via the drainage tube relief lumen), and activating a purge of the drainage line when the pressure increases above a certain threshold, for example −35, −30, −25, −20, −15, −10, −5 or 0 cmH2O.

When a clog is detected, the device may also warn the clinician of impending cardiac tamponade.

Figure 20:
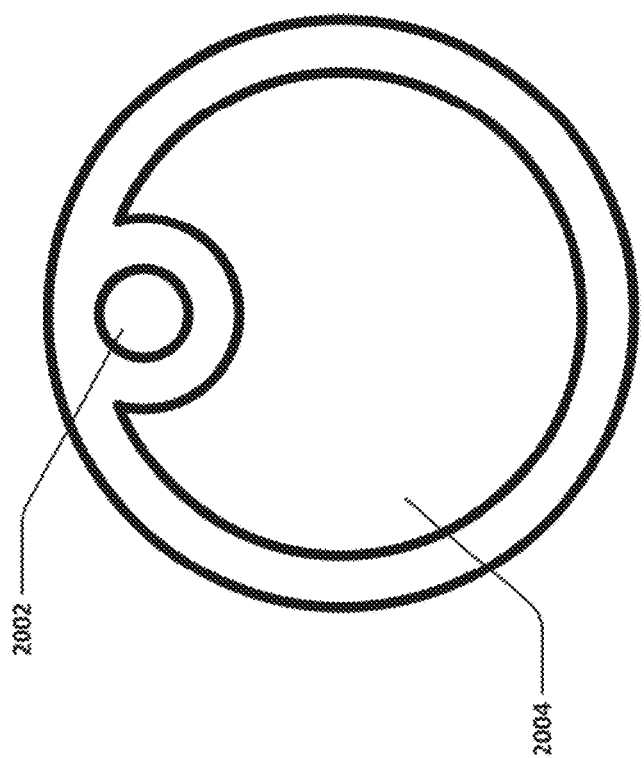
FIG. 20 illustrates an embodiment of the chest tube.

FIG. 20 illustrates an embodiment of the chest tube cross-section in more detail, showing chest tube relief lumen 2002 and chest tube drainage lumen 2004. In some embodiments, relief lumen 2002 may be significantly smaller in cross sectional area than drainage lumen 2004. The same may be true for the drainage tube relief lumen and drainage lumen. For example, the cross sectional area of the drainage lumen of either the chest tube or the drainage tube may be about 5 to about 10 times larger than the cross section of the associated relief lumen. Or for example, the cross sectional area of the drainage lumen of either the chest tube or the drainage tube may be about 10 to about 20 times larger than the cross section of the associated relief lumen. Or for example, the cross sectional area of the drainage lumen of either the chest tube or the drainage tube may be about 20 to 30 times larger than the cross section of the associated relief lumen. Or for example, the cross sectional area of the drainage lumen of either the chest tube or the drainage tube may be about 30 to 40 times larger than the cross section of the associated relief lumen.

Figure 21:
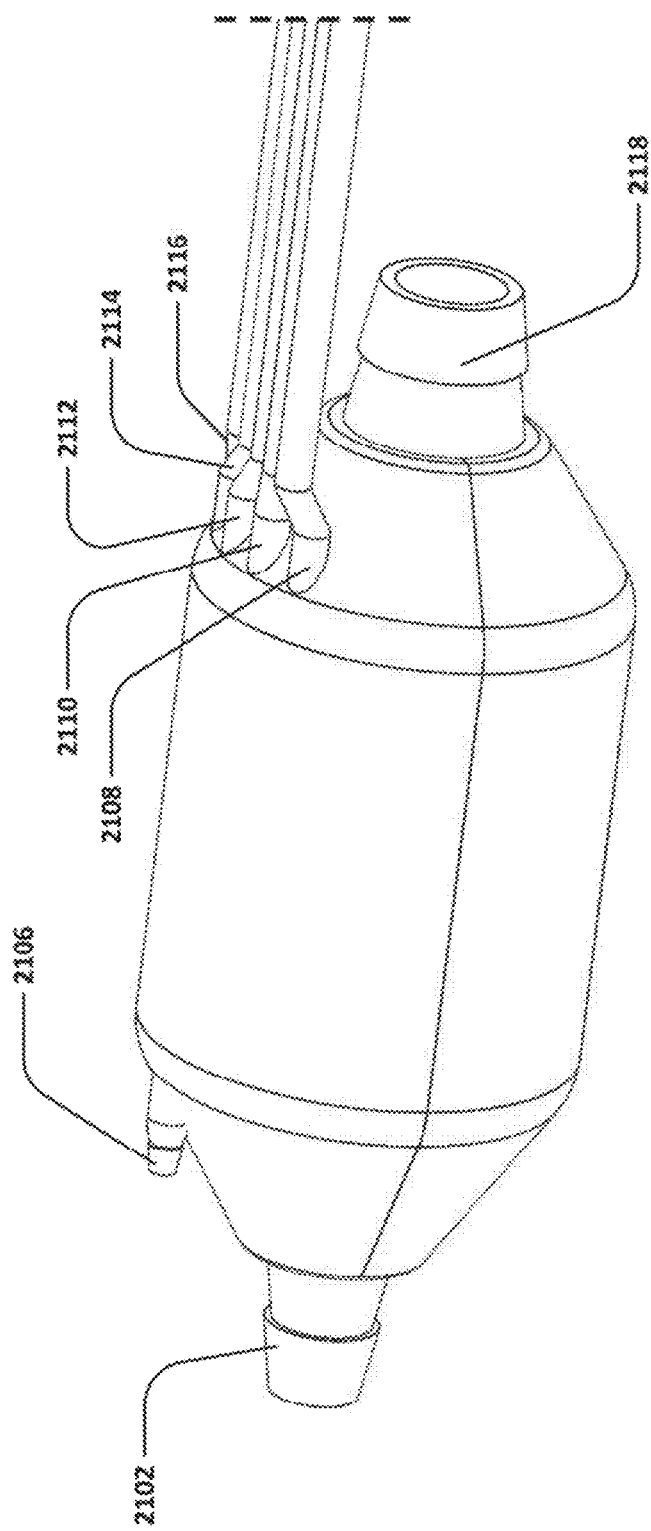
FIG. 21 shows an embodiment of the valve device.

FIG. 21 shows an embodiment of the valve device. Within the cylindrical housing are the balloon valves (including expandable valve) as illustrated in FIGS. 17A-D. FIG. 21 shows the valve device connecting points to the chest tube and drainage tube, as well as the relief lumens. Barb 2102 connects to the drainage lumen of the chest tube, barb 2106 connects to the chest tube relief lumen, the 5 pneumatic connecters 2108, 2110, 2112, 2114, and 2116 connect to chest tube relief lumen barb 2106, chest-side valve port 1704, lumen port 1706 (also described as the drainage tube relief port herein), chamber port 1718, and drainage-side valve port 1714 of FIG. 17A respectively. The pneumatic connecters may be in any order. Barb 2118 connects to the drainage tube drainage lumen. The other end of the pneumatic connecters connect to the monitor/controller and the pneumatics are controlled by the controller.

Figure 22:
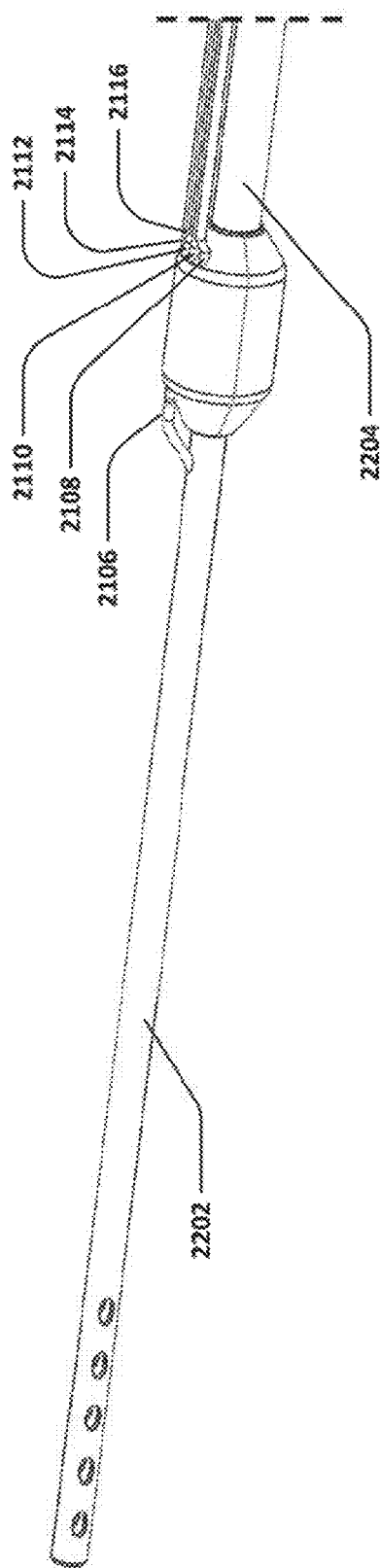
FIG. 22 shows an embodiment of the valve device with the chest tube and drainage tube.

FIG. 22 further illustrates these relationships by showing chest tube 2202, relief lumen barb 2106, drainage tubing 2204 and pneumatic connecters 2106-2116.

Figure 23:
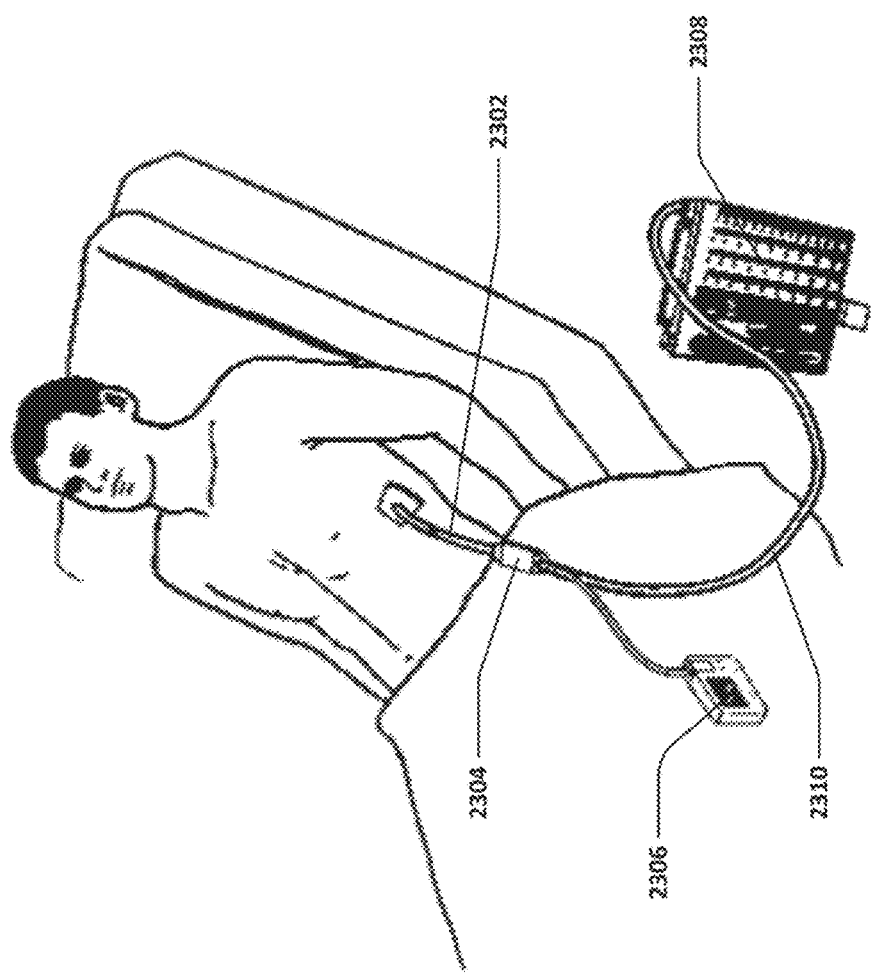
FIG. 23 shows an embodiment of the chest drainage system in use.

FIG. 23 shows an embodiment of the chest drainage system in use, including chest tube 2302, drainage tube 2310, valve device 2304 and monitor/controller 2306. In this embodiment, the system is connected to standard suction device/canister 2308. In this embodiment, the valve device is connected in line between the chest tube and drainage tube, with leads to the suction canister, and the monitor may be placed wherever is most convenient, including but not limited to the patient's bedside, IV pole, or mounted to the suction canister directly.

Figure 24:
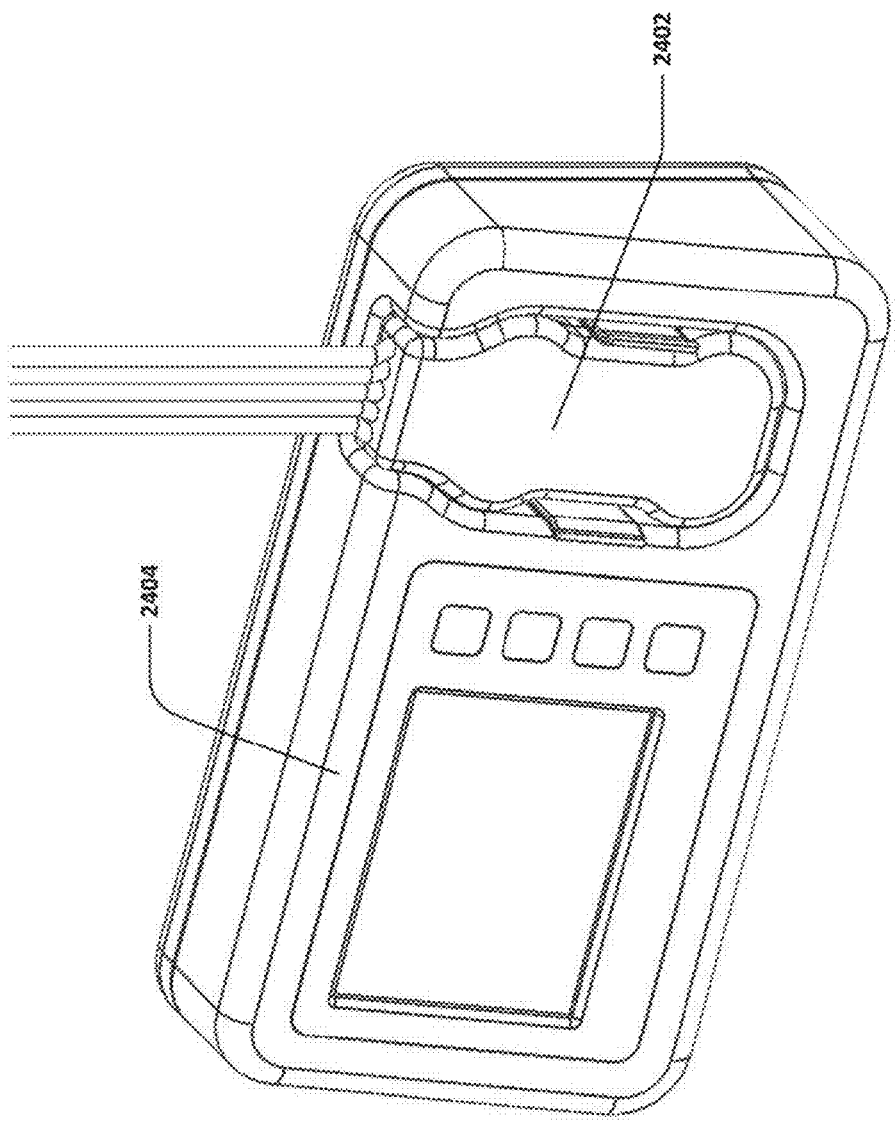
FIG. 24 shows the connection between the pneumatic connecters coming from the valve device and the monitor.
Figure 25:
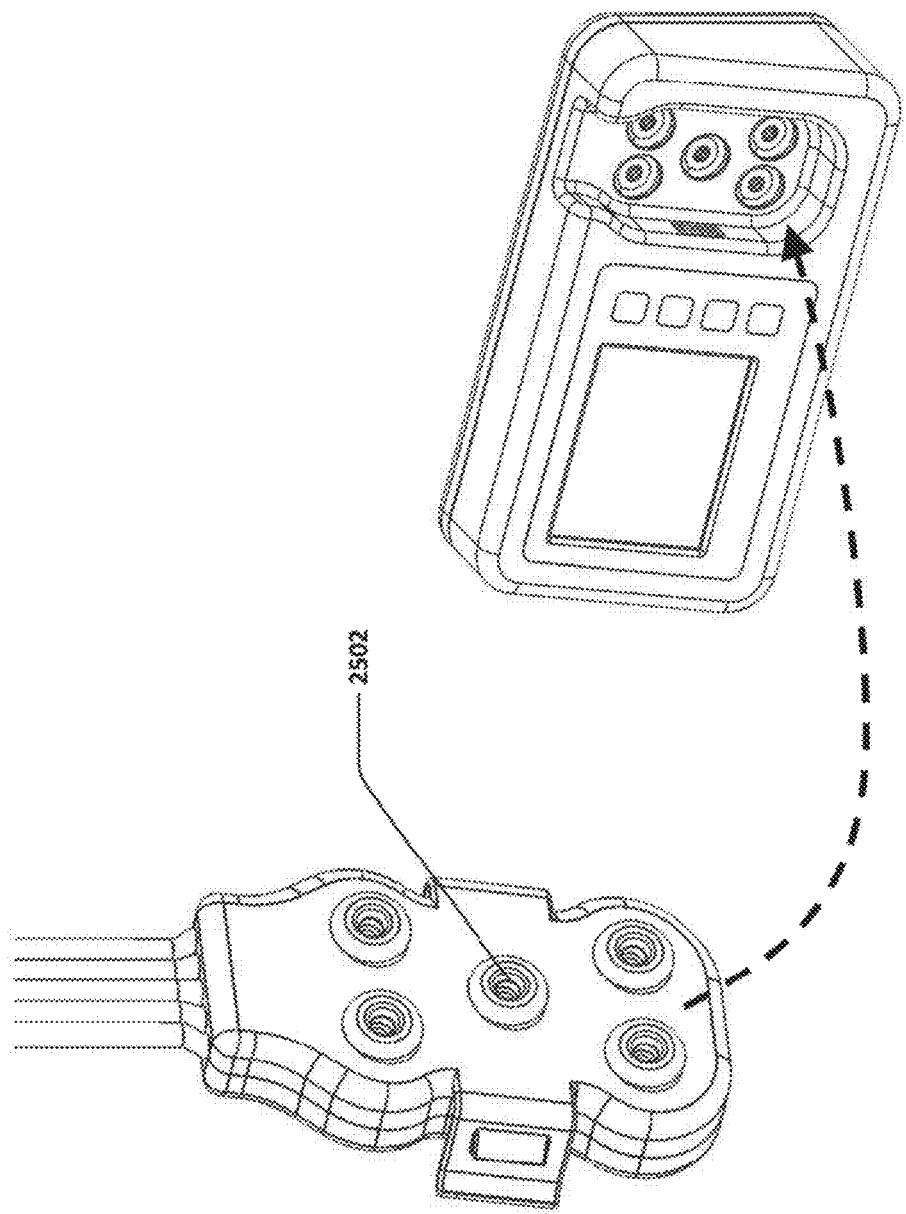
FIG. 25 shows the connection between the pneumatic connecter and the monitor.

The connection between the pneumatic connecters coming from the valve device and the monitor is illustrated in FIG. 24, which shows the monitor-side pneumatic connecter 2402, which connects to pneumatic connecters 2106-2116 in FIG. 21. Pneumatic connecter 2402 connects the relief lumens and balloon valves of the valve device to the pumps and solenoids housed within monitor 2404. The connecter preferably snaps into place, and seals against the monitor with gaskets 2502 as shown in FIG. 25. Preferably, the connections include membranes that act as sterile and/or liquid barriers to separate the lumens on the patient side of the system from those on the monitor side, thereby preventing contamination or liquid intrusion.

Figure 26:
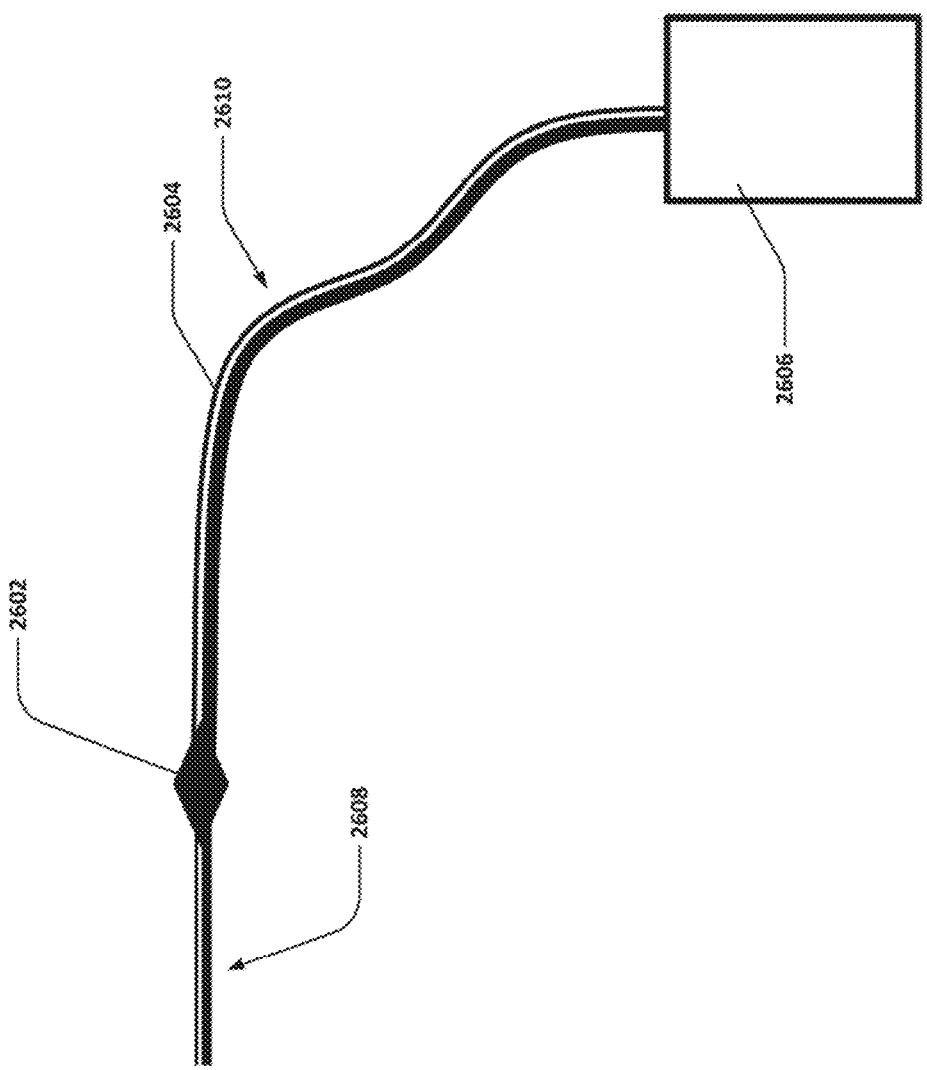
FIG. 26 shows an embodiment of the chest drainage system.

In yet another embodiment, the chest tube clog clearance and drainage line purging activities may be accomplished using a system shown in FIG. 26, in which a full length relief lumen 2604 runs the length of the system, from suction canister/reservoir 2606, through drainage tube 2610, through valve device 2602, through chest tube 2608 to the proximal tip (patient side) of the chest tube. In this embodiment, clogs are cleared from the chest tube and pooled liquid is cleared from the drainage line in the same step, by applying suction at the suction canister and opening the full length relief lumen to allow air to clear the entire system. Clearance of the line may be performed at set intervals, or when the pressure in the chest (measured via the relief lumen) increases above a certain threshold, for example −35, −30, −25, −20, −15, −10, −5 or 0 cmH2O, or a combination of these approaches. Also in this embodiment, balloon valves may or may not be present in valve device 2602. If not present, air leak measurement can be accomplished by measuring the pressure in the entire system and watching for attenuation as described herein. Alternatively, air leak can be measured by monitoring for bubbles as illustrated in FIG. 19. Alternatively, or in addition, air leak may be measured by measuring the air directly as it flows through the system with either an in-line flow sensor or by measuring/determining the volume of air moved by the suction pump to maintain adequate suction in the system. For example, a tachometer may be used to measure the number of revolutions of the motor driving the suction pump.

In some embodiments, the controller is connected to a network, either wired or wireless, in order to transmit data for example to and/or from the patient's electronic medical record (EMR). The controller may also provide notifications of patient status on the controller/monitor itself and/or by transmitting notifications and/or safety alarms to the EMR or the clinician's phone, tablet, watch, etc. Additionally, the system may interface with other systems via wireless or wired technology, and there may be wireless communication between the components, for example between the monitor shown in FIG. 24, the pneumatic connecter shown in FIG. 24, and/or the valve device shown in FIG. 21.

Figure 27:
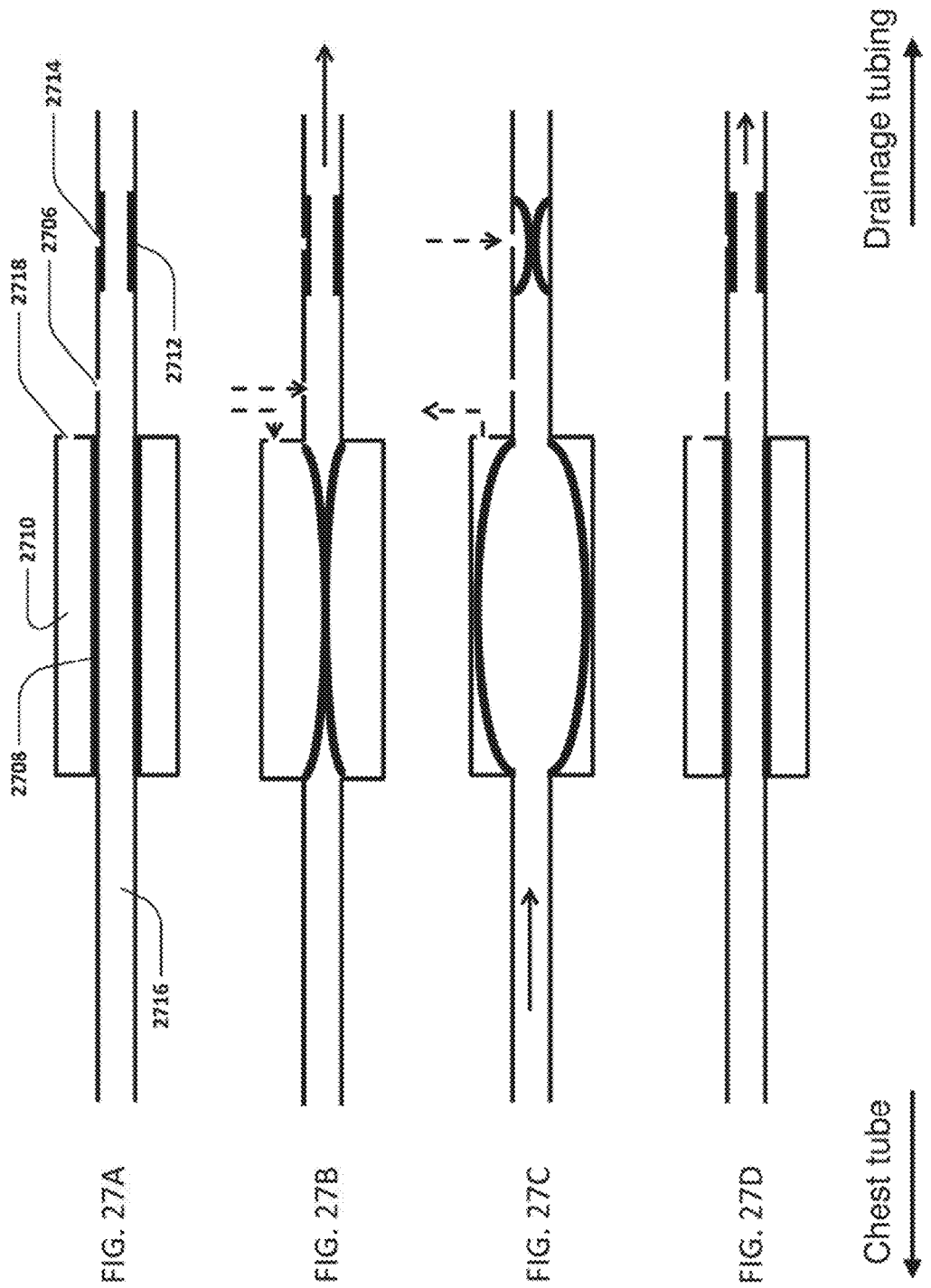
FIGS. 27A-27D show an embodiment of the valve device.

In another embodiment, the number of balloon valves may be reduced and/or the relief lumen port may be integrated with the valve device at a different location, as shown in FIGS. 27A-27D. The steps associated with this embodiment are:

Step 1. Inner lumen 2716 is sealed to seal the chest tube from the drainage tube. This is done by applying positive pressure to chamber 2710 via chamber port 2718. This closes expandable valve 2708 sealing off lumen 2716, as shown in FIG. 27B.

Step 2: The drainage tube is flushed by opening flush lumen port 2706 to atmospheric pressure or applying positive pressure to lumen port 2706. This is also shown in FIG. 27B.

Step 3: drainage-side balloon valve 2712 is then closed by applying pressure to the balloon via drainage-side valve port 2714. This is shown in FIG. 27C.

Step 4: The chest tube is exposed to additional negative pressure by applying negative pressure to expandable valve 2708 via chamber port 2718 of chamber 2710. Lumen port 2706 will be closed during this step. This is shown in FIG. 7C. The chest tube (not shown) in this step preferably has a relief lumen that is controllably opened to allow sterile air to enter the chest tube drainage lumen from the patient end as additional negative pressure is applied, which increases the effectiveness of clearance. Lumen 2716 is now fully open and drainage may resume as normal. This is shown in FIG. 27D.

In another embodiment, balloon valve 2712 may be removed such that the steps are:

Step 1: Inner lumen 2716 is sealed to seal the chest tube from the drainage tube. This is done by applying positive pressure to chamber 2710 via chamber port 2718. This closes expandable valve 2708 sealing off lumen 2716, as shown in FIG. 27B.

Step 2: The drainage tube is flushed by opening flush lumen port 2706 to atmospheric pressure or applying positive pressure to lumen port 2706. This is also shown in FIG. 27B.

Step 3: Clear the chest tube by returning the expandable valve 2708 to its neutral position and opening the chest tube relief lumen (not shown) (via a valve, either passive or active, not shown) to allow air to sweep the drainage lumen of the chest tube.

This approach eliminates the need for balloon 2712 and valve port 2714, which are only used when additional negative suction is pulled. Both of these steps may be performed by the controller at regular intervals. Alternatively, the chest tube relief lumen and/or the drainage tube relief lumen may be kept open at all times, or optionally closed when manually capped by the user as desired or by the controller.

In other embodiments, the action of sealing the balloon valves and generating suction, as disclosed in any of the embodiments herein, may be performed manually by the user, for example, similar to the system shown in FIG. 12. In some embodiments, the manual valve connecter allows for attachment of one or more syringes, which can be used to seal the balloon valves and generate additional suction and/or positive pressure for purging the drainage line. In some embodiments, the manual valve device employs a valve that can be configured to be 1) closed, 2) in communication with a chest-side or drainage-side balloon valve, or 3) in communication with the larger expandable valve. In this manner, the user may first connect to a balloon valve and apply positive pressure to create a seal, then connect to the larger expandable valve to generate additional suction. The relief lumen described herein (either the chest tube relief lumen of the drainage tube relief lumen) can also be activated automatically or manually, or alternatively can be activated passively by means of a check valve that cracks once the pressure rises above a certain threshold, as described in detail herein.

In an alternate embodiment, the means of generating positive pressure and suction is within the valve device itself, such as a fluid reservoir, so that a separate syringe is not required for activation.

In FIGS. 28A-28C, a method of measuring chest air leak is presented in more detail. In this embodiment, the chest tube and drainage tube are kept clear through the methods described herein. An air leak may be monitored and quantified at both relatively high and low air leak flow rates. The applied standard suction causes the pressure in the chest to be negative.

Figure 29:
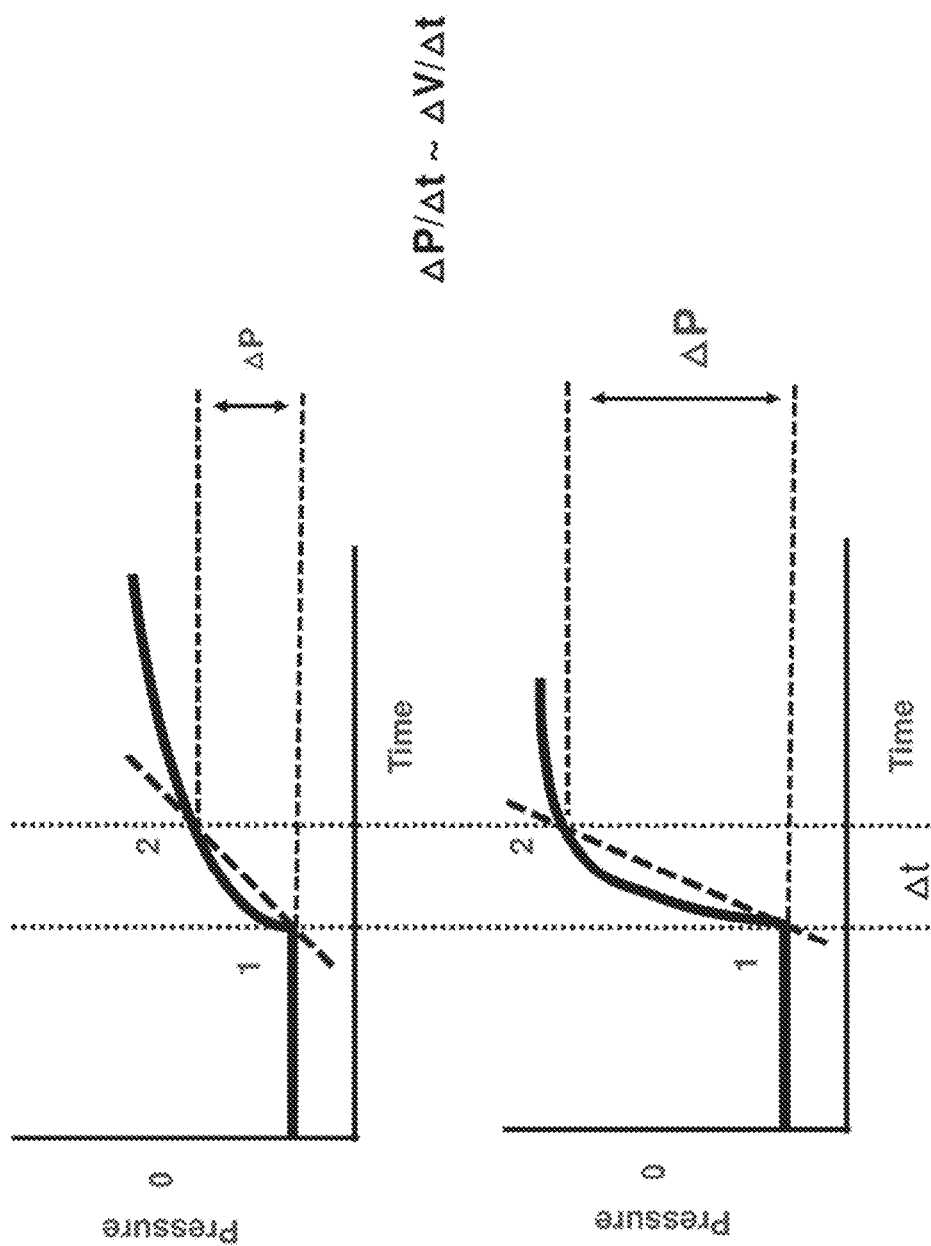
FIG. 29 depicts pressure over time for two different low flow air leak rate measurements.
Figure 30:
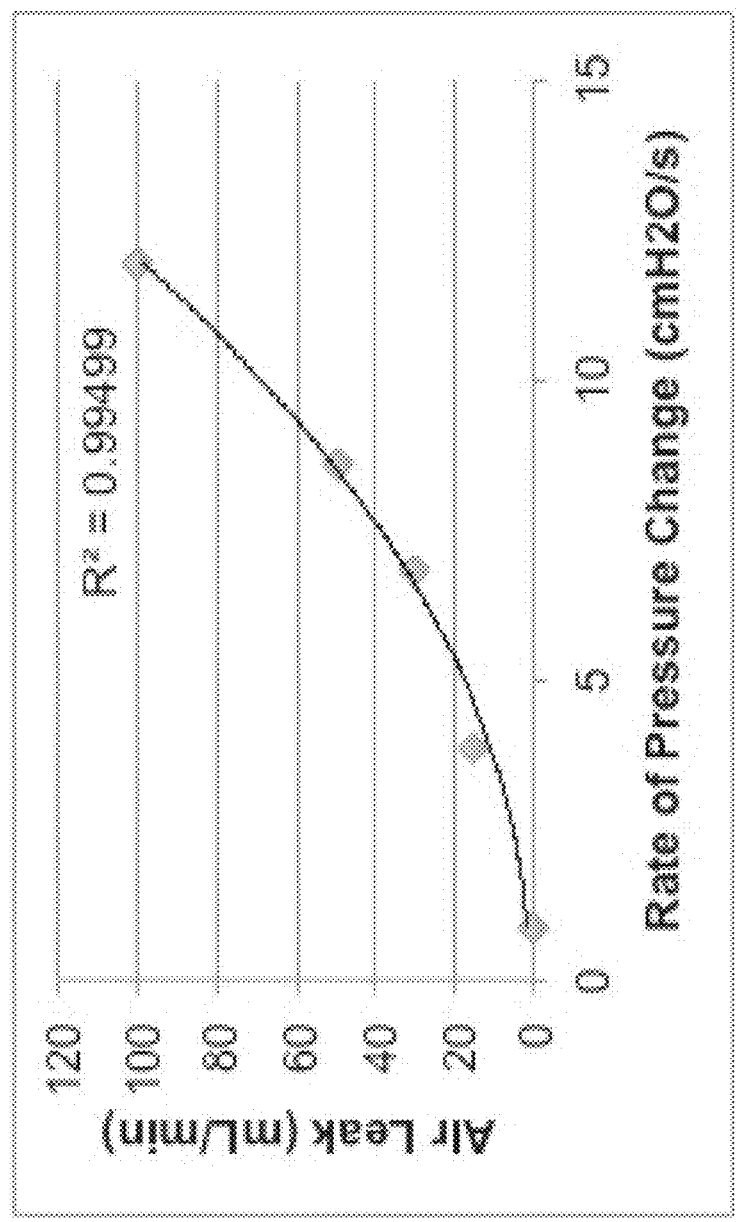
FIG. 30 shows a conversion of rate of pressure change to air leak.

In the presence of relatively low flow rates, positive pressure is applied to chamber 2810 via chamber port 2818 to close expandable valve 2808 to seal lumen 2816 as shown in FIG. 28B The pressure in the chest is then monitored via lumen port 2814; if there is an air leak, the measured negative pressure will become less negative as the incoming air enters the pleural space. FIG. 29 depicts an example pressure over time for two different low flow air leak rate measurements. The upper graph represents pressure attenuation over time in the presence of a small air leak, while the lower graph represents pressure attenuation over time in the presence of a larger air leak (still relatively low flow). The magnitude of the change in pressure is indicated by the slope of the line intersecting points 1 and 2. The rate at which the pressure increases ($\Delta P/\Delta t$) may be converted to volumetric air leak rate ($\Delta V/\Delta t$). Points 1 and 2 may be determined based solely on time, for example taking measurements 0.5 and 1 sec after creating the seal as shown in FIG. 28B. Alternatively, they may be based on pressure values, either absolute (e.g. once the pressure goes above −10 and −5 cmH2O) or relative (e.g. once the pressure increases by 2 and 4 cmH2O relative to baseline). Sample benchtop data illustrating this technique is presented in FIG. 30, which utilizes a second degree polynomial fit to convert rate of pressure change to air leak.

Figure 31:
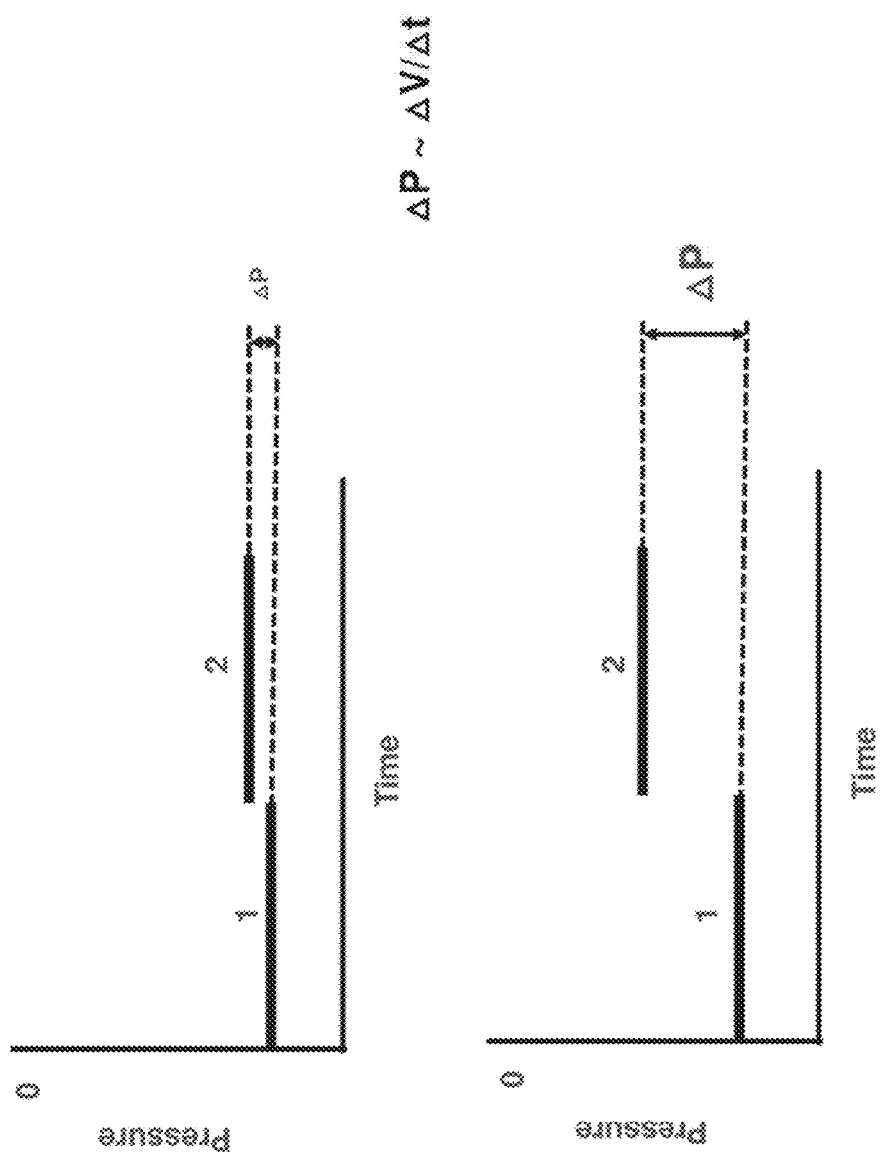
FIG. 31 depicts pressure over time for two different high flow air leak rate measurements.
Figure 32:
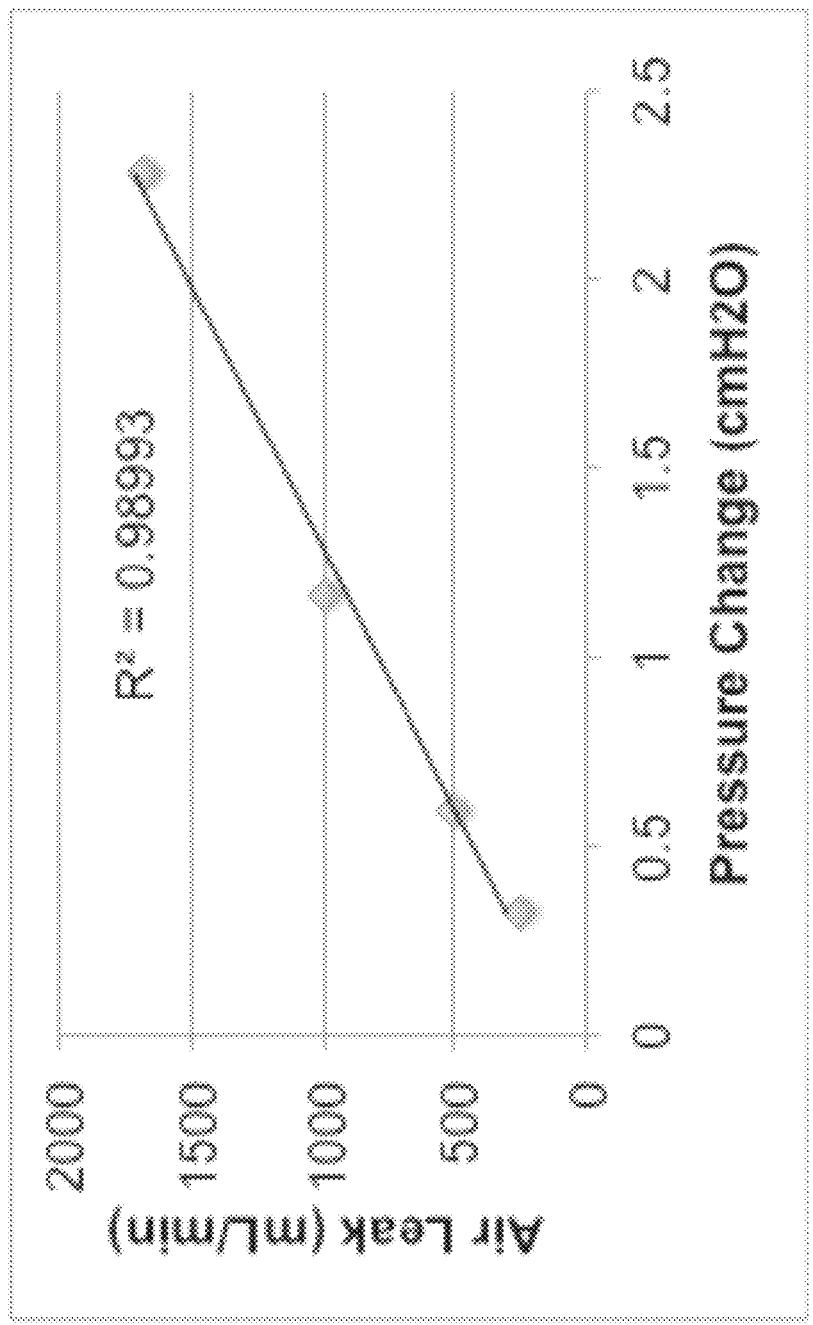
FIG. 32 shows a conversion of rate of pressure change to air leak.

In the presence of relatively high flow rates, positive pressure is applied via balloon valve port 2804 to close balloon valve 2802 to seal lumen 2816, sealing off the drainage lumen of the chest tube from the drainage lumen of the drainage tube. This is shown in FIG. 28C. The pressure is then monitored via lumen port 2814 to determine a baseline pressure value due to the applied suction only (via negative pressure applied to the drainage tube). Then, balloon valve 2802 is opened and a new pressure value is measured, once again via lumen port 2814. If the air leak rate is high, there will be a larger detectable difference between the two aforementioned pressure measurements due to the rapid influx of air. This is shown in FIG. 31. The upper graph represents a pressure differential in the presence of a relatively small air leak (though still high flow), while the lower graph represents a pressure differential in the presence of a larger air leak. The magnitude of the difference between these two measurements ($\Delta P$) may be converted to volumetric air leak rate ($\Delta V/\Delta t$). Sample benchtop data illustrating this technique is presented in FIG. 32, which uses a linear fit to convert rate of pressure change to air leak.

Figure 28:
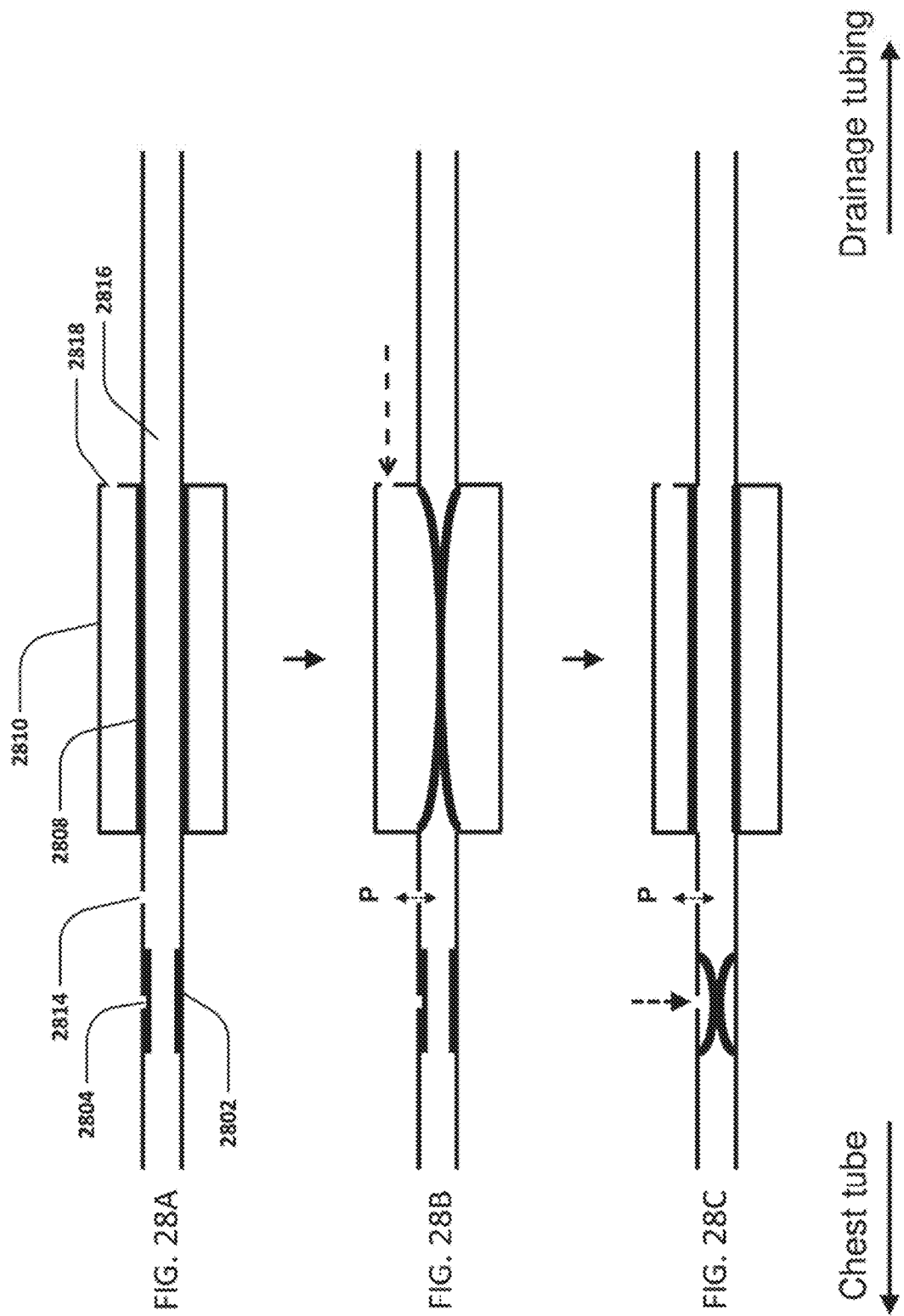
FIGS. 28A-28C show a method of measuring chest/thoracic air leak.

The same methods of determining air leaks shown for low and high flow scenarios may also be performed by swapping the positions of the balloon valves in FIG. 28, relative to lumen port 2814. In this case, the balloon valve seal is inflated/closed when measuring low flow and the larger expandable valve is inflated/closed when measuring high flow.

One embodiment of the device may include a method for detecting the presence, as well as proper placement, of the pneumatic cassette module (2402 in FIG. 24) in the monitor (2404 in FIG. 24). This detection information may be used to start or stop functionality of the device, activate or deactivate certain features of the device, sound alarms and/or display alert messages on the device, etc.

Figure 33:
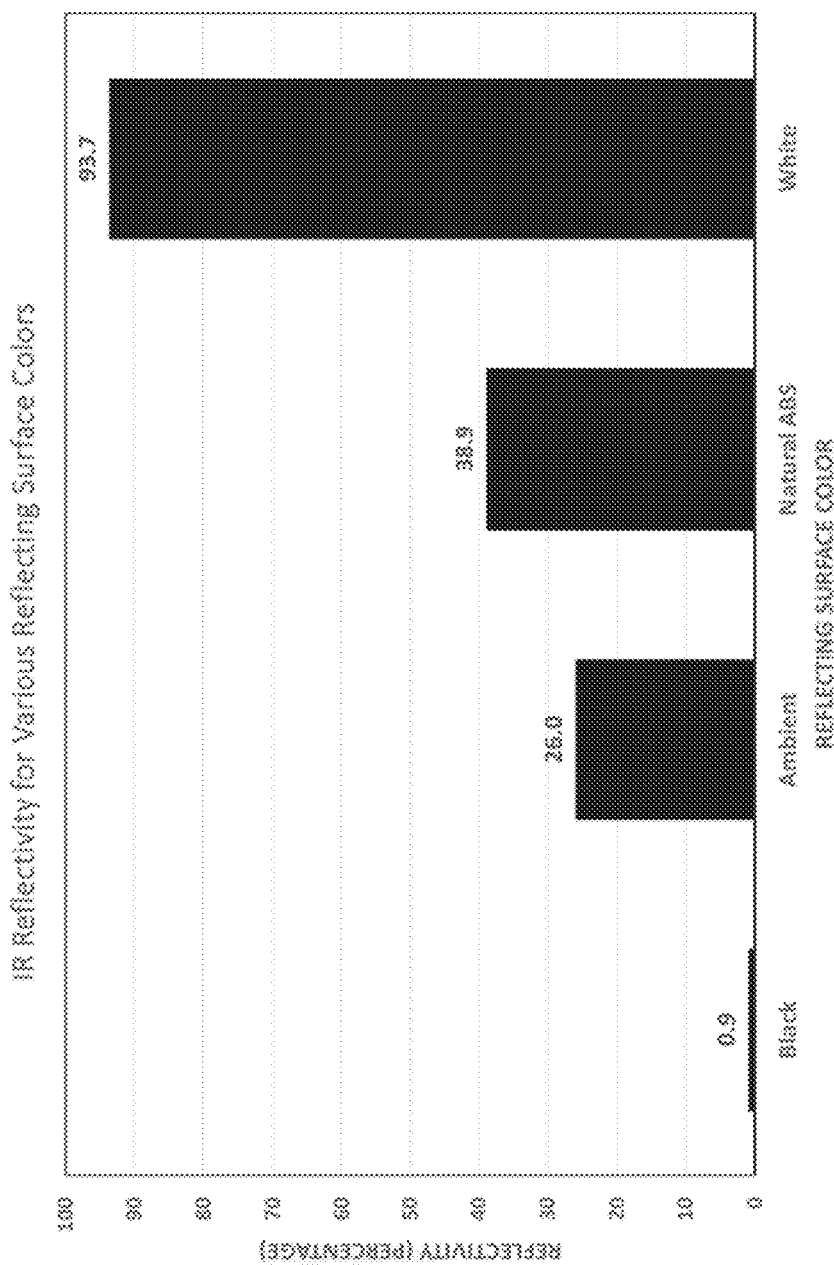
FIG. 33 shows the relationship between color and reflectance readings.
Figure 34:
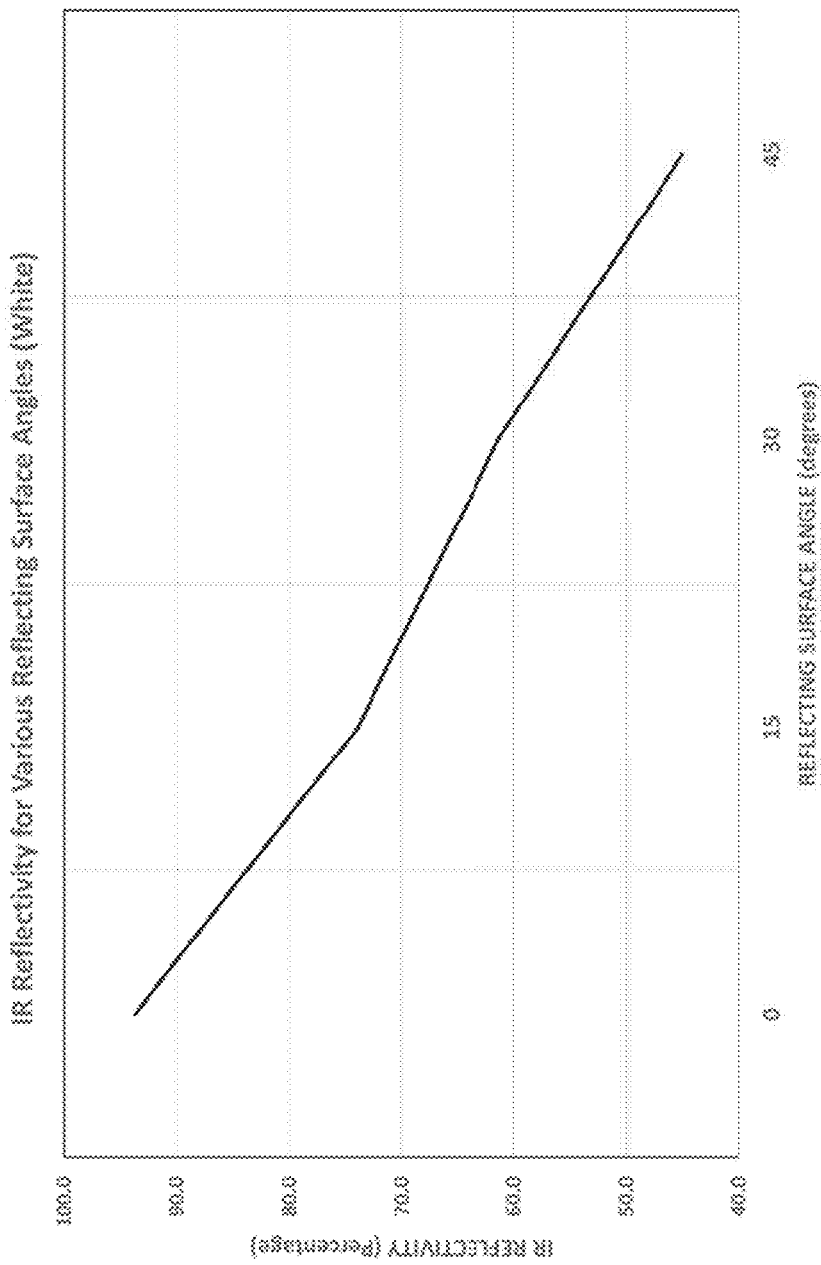
FIG. 34 shows the relation between surface angle and reflectance readings.

One method for cassette detection may use an Infrared (IR) emitter and receiver to detect the presence and proper placement of the cassette. This IR sensor may measure the reflectivity of the cassette surface; the information may be used to inform device function. The reflectivity of the cassette may be modified to allow for a wide variety of reflectance values. The reflectivity of the cassette may be controlled by changing the color, geometry, or any combination of color and geometry to adjust reflectance. In FIG. 33, the relationship between color and reflectance readings is shown, where the possible range of values may be 0-100%. In FIG. 34, the relation between surface angle and reflectance readings is shown for a white surface where again, the possible range of values may be 0-100%.

Another method for cassette detection may use a color sensor with attached LED to illuminate the surface to be measured. This color sensor may be capable of detecting various levels of a specific color, such as red and/or cyan, light intensity, light temperature, as well as any combination of these metrics. In one embodiment, the color of the cassette may be used to differentiate between two or more desired function settings of the device. In another embodiment, the cassette may have features which allow a certain amount of light to reach the sensor, thus, variable light intensity may be used to control function settings of the device. In another embodiment, the cassette may have features which modify the temperature of the light reaching the sensor, a light filter for example; thus, variable light temperature may be used to control function settings of the device.

Another method for cassette detection may use a Hall Effect sensor to detect the presence of a magnet, located in the cassette. This magnetic sensor may be used to ensure complete and proper placement of cassette to locked-position in monitor by defining placement of the magnet and Hall Effect sensor, such that detection only occurs when the cassette is fully seated and locked in place.

Another method for cassette detection may use an IR gate sensor to detect both the presence of the cassette in the monitor, as well as ensuring proper placement in the monitor. The cassette may include a feature or features which may interact with the IR gate sensor, providing information regarding the placement of the cassette in the monitor.

Another method for cassette detection may utilize a UV light sensor to detect the presence and proper placement of the cassette in the monitor. To allow for variability between cassettes, features may be added to the cassette which modify the amount of UV light permitted to reach the sensor. This may be accomplished using, for example, UV filters, passageways within the cassette, openings, mirrors, or some combination of these features.

Another method for cassette detection may involve capacitive sensing, whereby the cassette has varying levels of dielectric strength depending on, for example, the size of a strip of metal embedded in or mounted to the cassette. A capacitive sensor within the monitor may then be able to distinguish between the various cassettes depending on this varying level of capacitance.

One embodiment of the device may include a method for measuring and quantifying air leak metrics which are then displayed via a screen on the monitor or elsewhere. This information may be used to start or stop functionality of the device, activate/deactivate certain features of the device, sound alarms and/or display alert messages on the device, provide information to attending physicians, as well as other actions related to proper removal of fluids from the chest. These actions may be performed manually or automatically be the controller.

Figure 35:
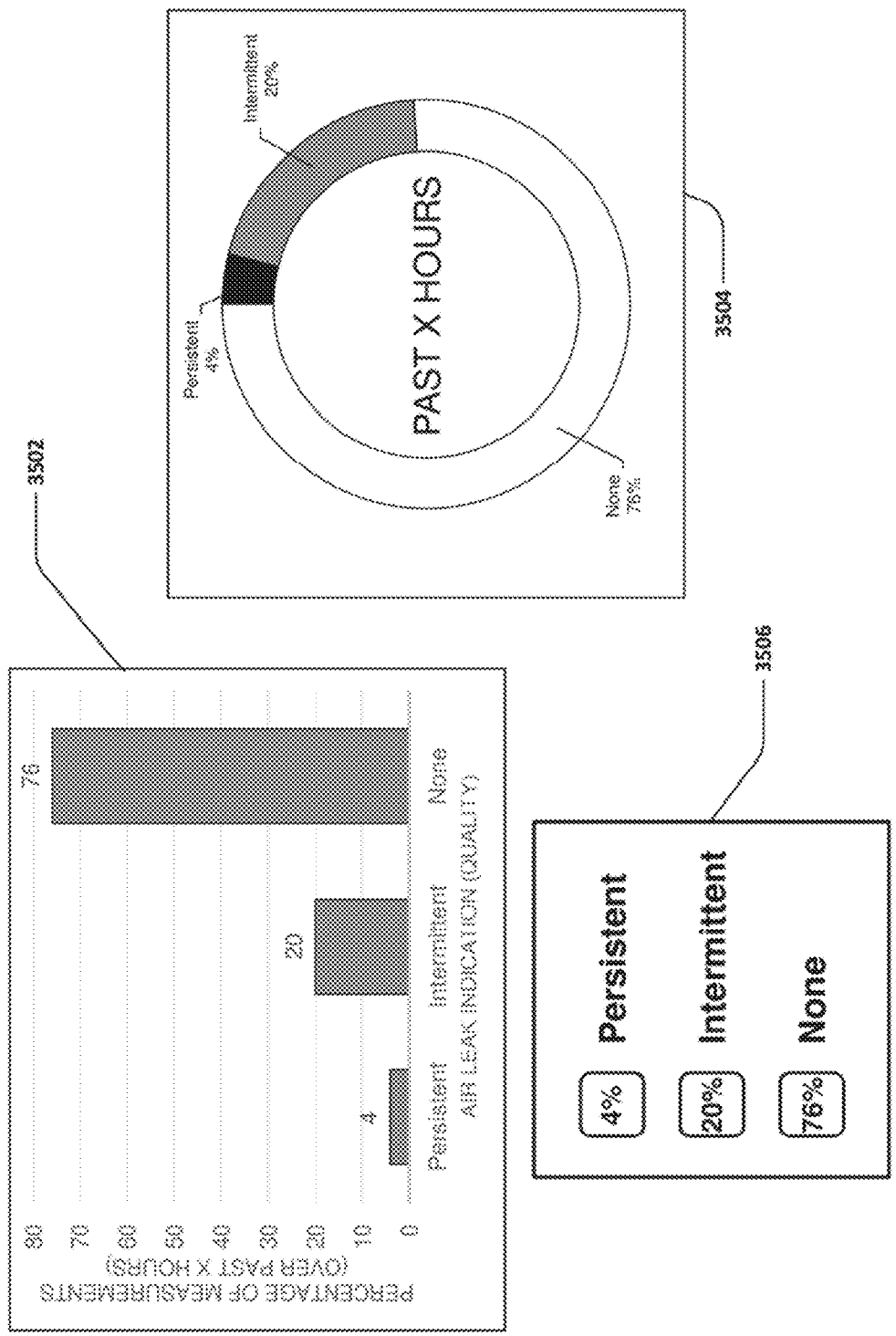
FIG. 35 shows a display of chest//thoracic air leak information.

One method for displaying air leak data may include describing the occurrence of a particular air leak qualifier by showing the percentage of measurements over the previous X hours for which that qualifier occurred. The air leak qualifiers may include/be equivalent to: "Persistent" for high flow, "Intermittent" for moderate to low flow, and "None" for no flow. As shown in FIG. 35, this information may be presented, for example, graphically as a bar graph 3502 or circular chart 3504, or in a display using text and numbers (3506).

Figure 36:
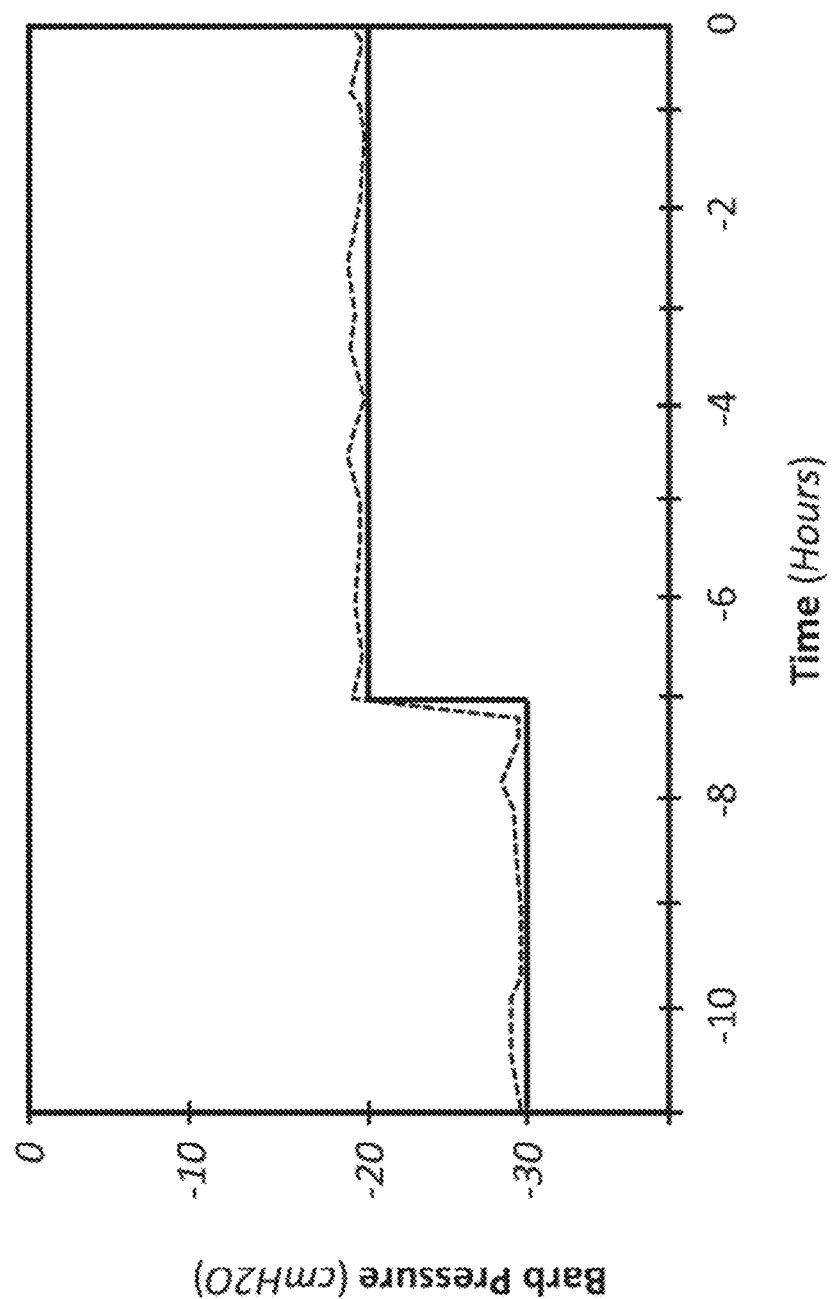
FIG. 36 shows a display of chest//thoracic air leak information.

Another method for presenting air leak data may include graphing trending flow rate data over a period of time, for example 1-48 hours. The air leak flow rate information may be collected, for example, using an in-line flow sensor, pressure sensors, or pump tachometer. As shown in FIG. 36, the air leak flow rate trending data may be expressed as (ml/min) with respect to time in hours past, for example. The pressure shown here is measured at the barb (or tube-tube interface) area.

Figure 37:
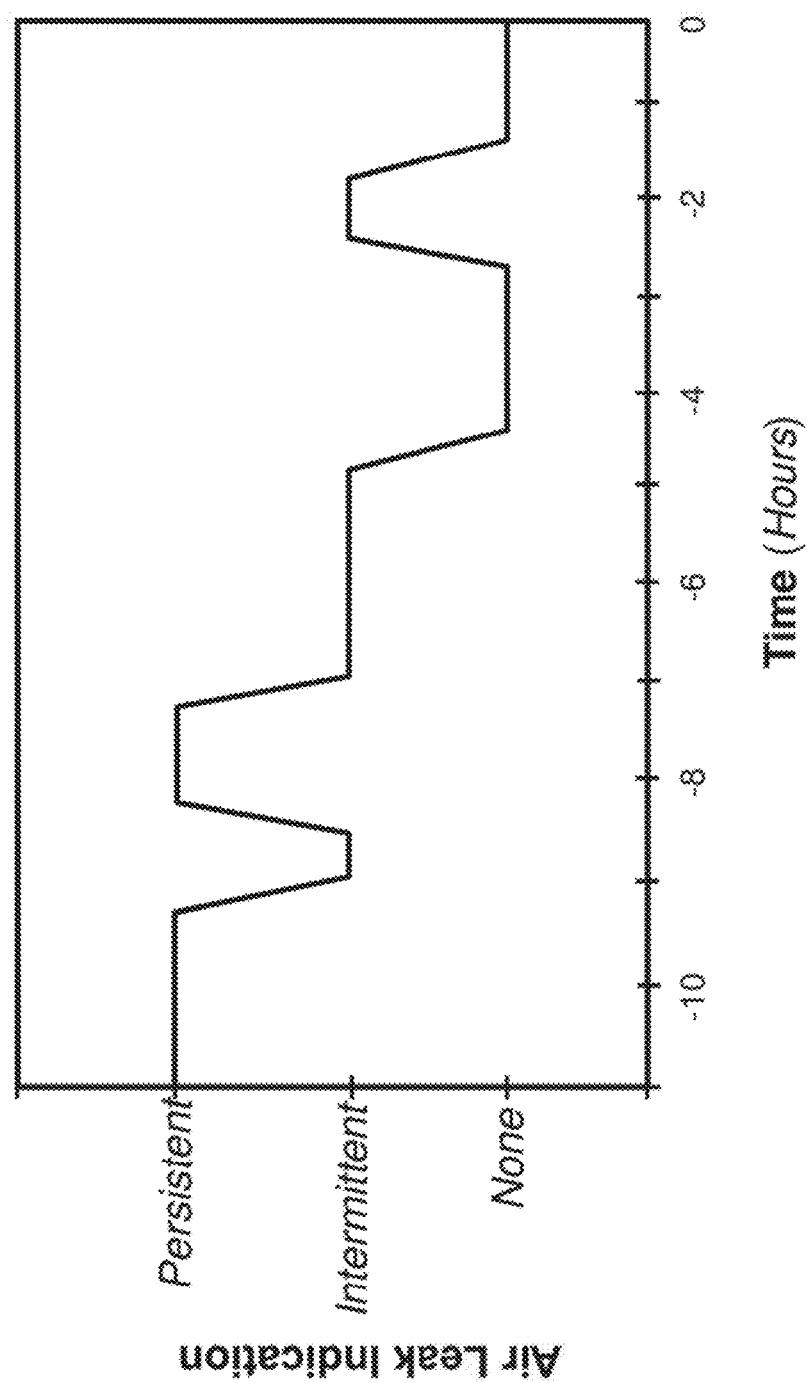
FIG. 37 shows a display of chest//thoracic air leak information.

Another method for presenting air leak data may include graphing trending air leak qualifiers over a period of time, for example 1-48 hours. The air leak qualifier information may be calculated, for example, using algorithms to relate changes in chest or chest tube pressure to volumetric flow rate, or defining a pressure threshold, for example −5 cmH2O, and relating the time to reach that value with a qualifier. As shown in FIG. 37, the air leak qualifier trending data may be expressed as, for example, "Persistent", "Intermittent", and "None" with respect to time in past, for example, for the past x hours.

Figure 38:
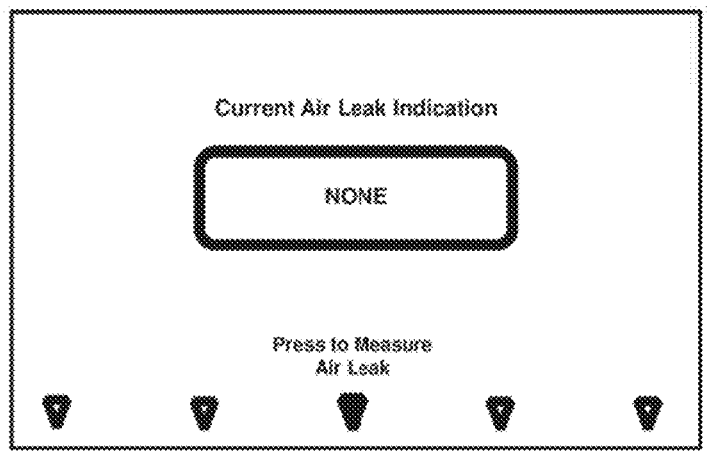
FIG. 38 shows a display of chest//thoracic air leak information.

Another method for presenting air leak data may include an instantaneous measurement initiated by, for example, pushing a button. As shown in FIG. 38, the prompt for instantaneous measurement may be a highlighted arrow, a physical button, a virtual button, graphic etc. The information provided may be in the form of, for example, flow rate (ml/min) or an air leak qualifier, such as "Persistent", "Intermittent", "None", or an equivalent term.

One embodiment of the device may include a method for measuring and quantifying clog clearance metrics to be displayed via a display or screen. This information may be used to start or stop functionality of the device, activate/deactivate certain features of the device, sound alarms and/or display alert messages on the device, provide information to attending physicians, as well as other actions related to proper removal of fluids from the chest.

Figure 39:
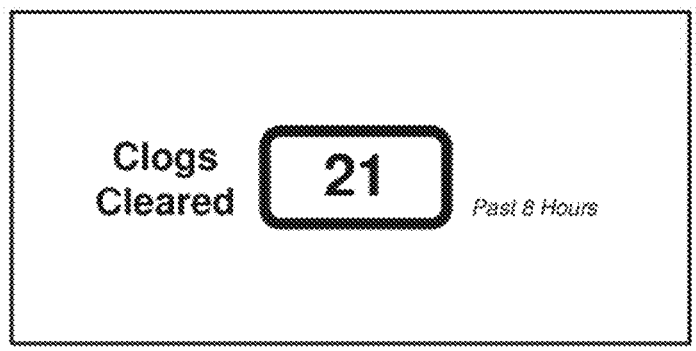
FIG. 39 shows a display of clog removal information.

One method for presenting clog clearance data may include displaying the number of clogs cleared over a certain amount of time, for example 1-48 hours—the range may be set by the user or may be pre-set. As shown in FIG. 39, the information displayed may include a description of the displayed metric, for example "Clogs Cleared", a number or quantifier associated with the metric, for example, the number of clogs cleared, and the time interval over which the metric occurred.

Figure 40:
FIG. 40 shows a display of clog removal information.

Another method for presenting clog clearance data may include, for example, displaying the time for when the last clog occurred, the date on which the last clog occurred, whether the clog was cleared, the time passed since the last clog occurred, or some combination of these or similar metrics. As shown in FIG. 40, the information displayed may indicate what metric is being shown, for example "Last Clog".

Figure 41:
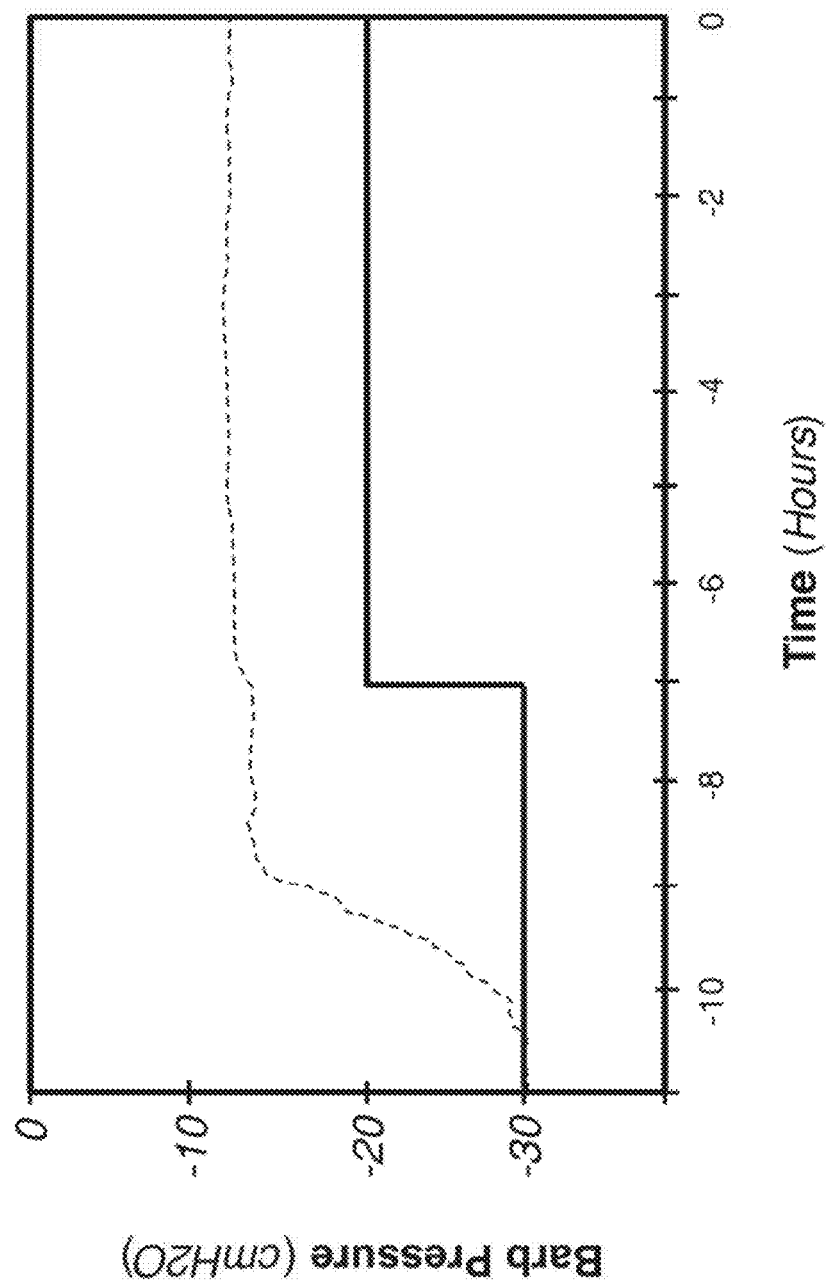
FIG. 41 shows a display of suction pressure information.

Another method for presenting clog clearance data may include a graph displaying trending pressure data from the tube-tube interface area, or elsewhere in the system, over a certain amount of time, for example 1-48 hours, for a certain range of pressures, for example −500-500 cmH2O. As shown in FIG. 41, one or more pressure values may be plotted simultaneously with respect to time, for example, pressures measured at different locations within the system. For example, the graph may display the applied suction level set by the user, shown by the solid line, and/or the graph may display the pressure measured in the tube-tube interface area, shown by the dashed line.

Figure 42:
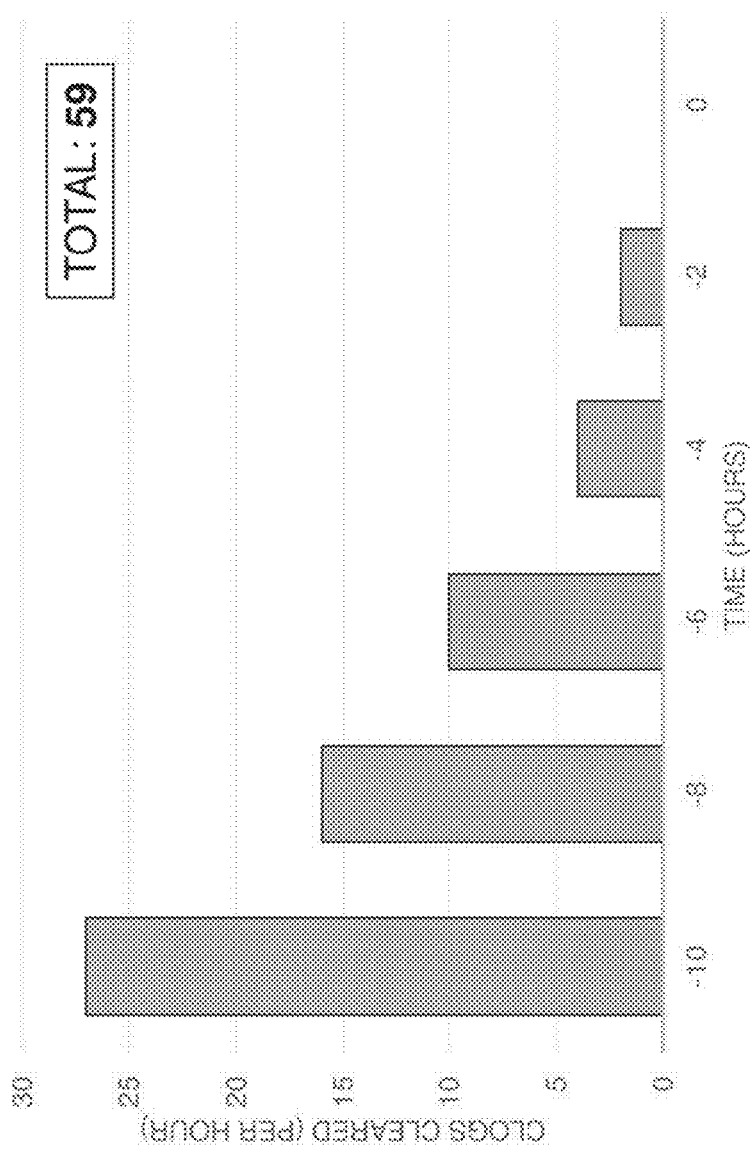
FIG. 42 shows a display of clog removal information.

Another method for presenting clog clearance data may include a graph displaying trending clog clearance data for a specific time interval (for example, 1 hour), over a certain amount of time, for example 1-48 hours. As shown in FIG. 42, a bar graph may be utilized to convey information regarding the number of clogs cleared each hour over the past 10 hours, for example. The total number of clogs cleared over the total duration of device use for a particular patient may also be shown.

Figure 43A:
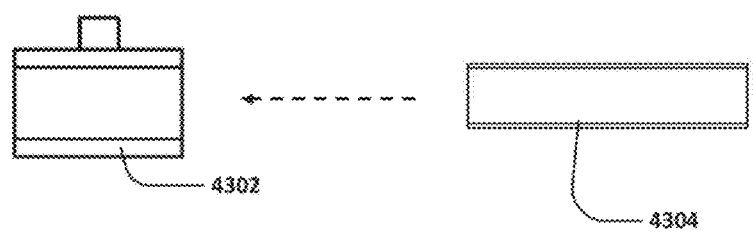
FIGS. 43A-43E show manufacturing steps and components of balloon valves.
Figure 43B:
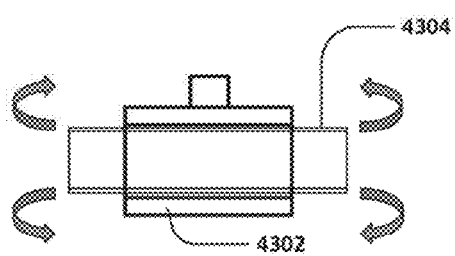
Figure 43C:
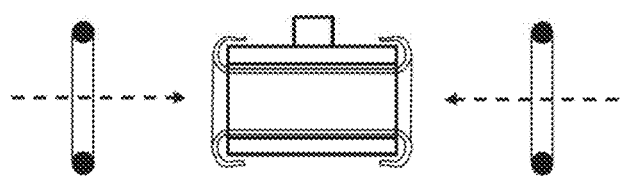
Figure 43D:
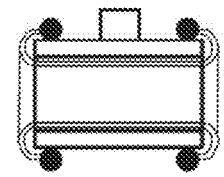
Figure 43E:
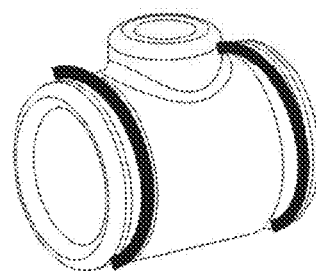

Some embodiments disclosed herein include a balloon, or pneumatic, valve, which uses pressure variance to occlude or open the passageway by inflating or deflating a flexible membrane, or balloon. FIGS. 43A-43E show an embodiment of these types of valves. The valve includes rigid housing 4302 and thin-walled silicone extrusion 4304, as shown in FIGS. 43A-E. Silicone extrusion 4304 may be either an extrusion or a mold out of any suitable material, including silicone, latex, polymer, etc. The durometer of the silicone may be, for example 20A-70A, and the wall thickness, for example 0.005"-0.050". The wall thickness may be adjusted to achieve the desired sealing pressure. The wall thickness may be consistent along the length or vary along the length. The length of the silicone extrusion may be 0.5"-1.0" and the inner diameter of the silicone extrusion may be 0.1"-0.50". In one embodiment example of the balloon valve, assembly begins by inserting the silicone extrusion through the center of the balloon housing. Next, the extrusion is folded up and over the edge of the housing on both ends as shown in FIGS. 43B and 43C. This process may be done several ways, for example, manually folding the extrusion. Another process may include inserting a balloon through the center of the extrusion; upon placement, this balloon could be inflated, effectively expanding the silicone membrane until it folds over the edge of the housing. Another process may incorporate a fixture which has two or more grasping features that expand radially in and out; the grasping features are used to grab and expand the silicone extrusion; once the extrusion is stretched, the housing may be moved forward to accomplish the folding process. As shown in FIGS. 43C and 43D, once the extrusion is folded over the housing, two O-rings are placed over the silicone extrusion to ensure that the silicone membrane remains in place and is sealed with respect to the housing. FIGS. 43 D and 43E show the finished balloon valve.

One embodiment of the chest drainage system may include vent/filter membranes in line with the pneumatic tubing for the purpose of controlling quality of the air or adding dampening to the system. These membranes may have variable thickness, for example 0.001"-0.010", have variable pore sizes, for example 0.2-100 micron, have variable cross sectional areas, for example 0.01-0.1 in2, and have different cross sectional shapes, for example circular or rectangular. The membranes may be placed within the cassette, in line with the pneumatic tubing via barb connection, within the monitor, or within the valve device. These vent membranes may be attached in many ways, for example ultrasonic welding, via a separate housing, or UV cure adhesive.

One embodiment of the chest drainage system may include a feature which allows the monitor to be mounted in a convenient and effective location during use in various hospital settings. This connection feature may be modular: the monitor may have a feature that can connect to many different attachments that offer different mounting solutions. One iteration of the modular design may include a snap-and-lock feature, where the attachment locks into place and can be released, for example, by pushing a button to disengage the lock. Another iteration may include a threaded hole in the monitor that interfaces with a threaded rod on the attachment. Yet another iteration may include a sliding mechanism where the attachment grabs onto rails or tracks to connect with the monitor. Another iteration may include a push-and-lock feature, where the attachment can be locked and unlocked by pushing it further into the connection, similar to an SD card. Another iteration may include a single or series of magnet(s) which properly orient and hold the attachment firmly to the monitor.

One method for creating a mounting feature may include the use of a rigid bracket on which a pair of hook features are connected. As shown in FIG. 44, bracket assembly 4402 may connect to the monitor via one of the modular mounting options 4404. Hooks 4406 may be attached in such a way that they are able to pivot to provide increased adaptability.

Figure 45:
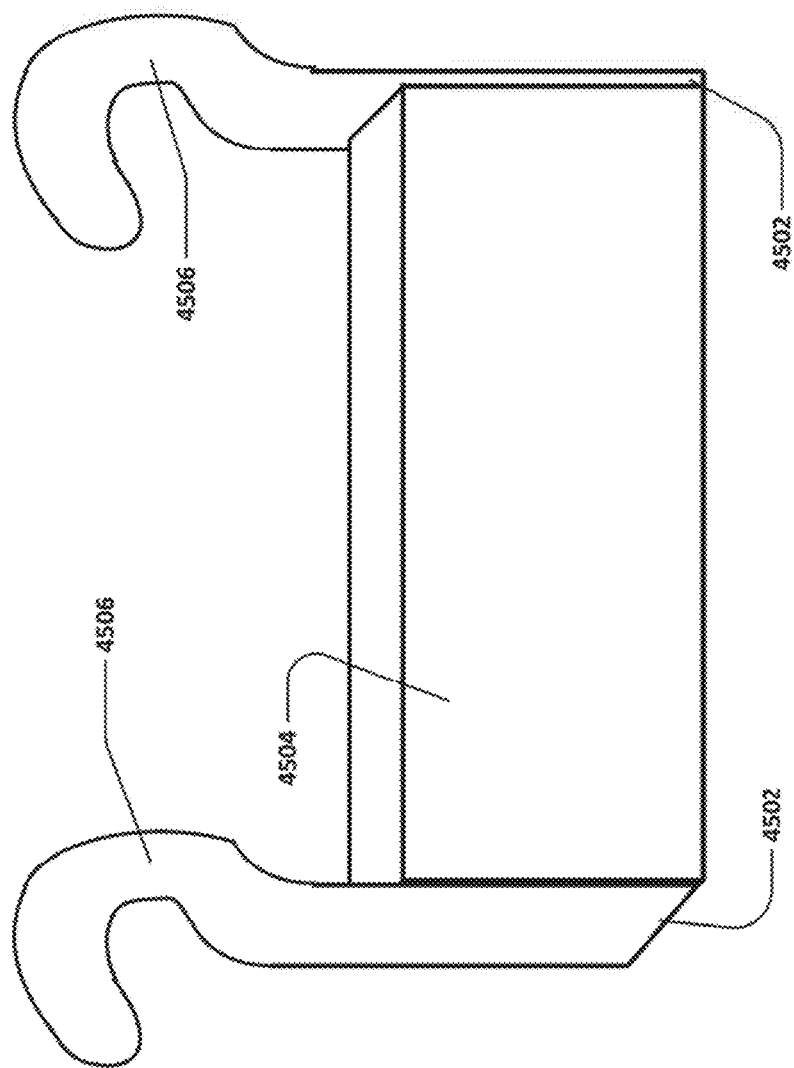
FIG. 45 shows an embodiment of a mounting device.

Another method for creating a mounting feature may include the use of flexible straps in combination with a hook feature. As shown in FIG. 45, straps 4502 may be attached to the base of monitor 4504 and cover the sides of the monitor, with hook features 4506 integrated with the strap. These straps may be fixed or moveable, for example, they may be able to retract inside of the monitor when not in use. In this case, the hook features may have a place to be stored as well, for example external wells into which the hooks click in place.

Figure 46:
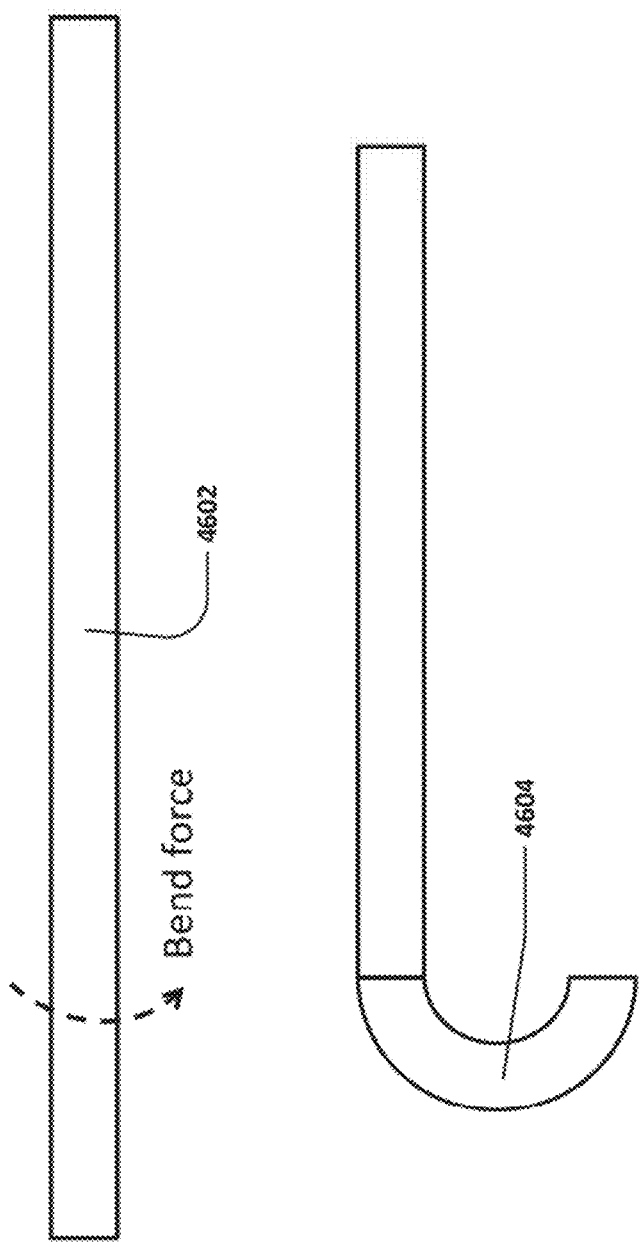
FIG. 46 shows an embodiment of a mounting device.

Another method for creating a mounting feature may include the use of flexible tubing to provide a highly adaptive solution with many potential uses. As shown in FIG. 46, tubing 4602 may be able to take many shapes by simply bending the tube to create a desired shape or feature, such as hook shape 4604. These tubes may be attached to the monitor on the back or sides, using one of the modular mounting options described herein. The force required to bend the tubing is low enough to not require a special tool, while simultaneously being stiff enough to hold its shape under the loads placed on it by the monitor and additional external forces.

Figure 51:
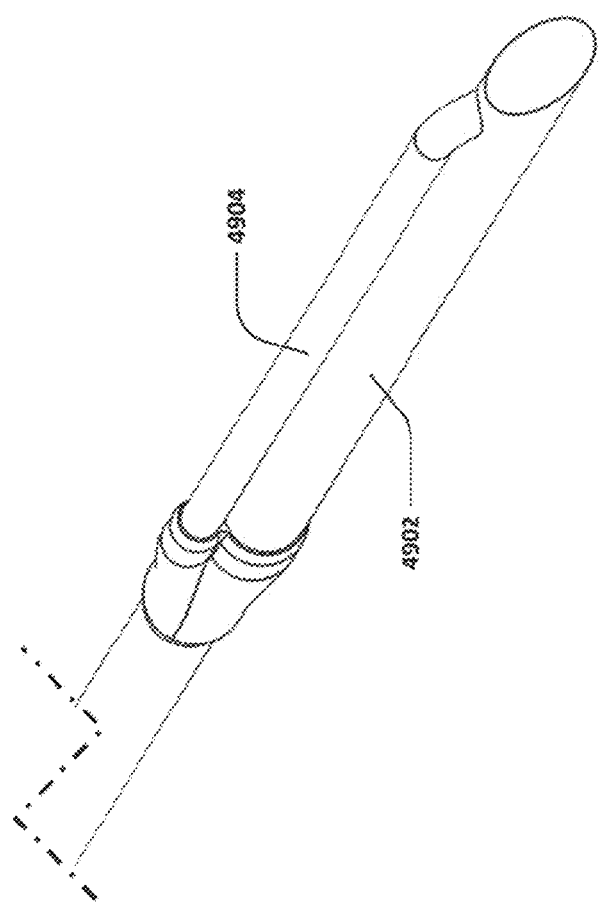
FIG. 51 shows an embodiment of a dual-lumen chest tube.

FIGS. 47, 48, 49 and 50 show an embodiment of a dual-lumen chest tube. Chest tube 4702 may be made using silicone, PVC, or other suitable material with a suitable durometer, for example 20A-80A. The effective outer diameter of the chest tube may vary between 8Fr-40Fr. The chest tube shown in FIG. 47 may include three sections: a chest tube region, as shown in FIG. 48, a transition region, as shown in FIG. 49, and a pull-through region, as shown in FIG. 50. The chest tube region comprises a dual-lumen extrusion with holes 4802 near the patient side for drainage of fluid from the body. The chest tube region is preferably capped with rounded tip 4804, but may also have an open patient end without a cap. The transition region separates the two chest tube lumens, for example chest tube drainage lumen and the chest tube relief lumen, into separate tube sections that are more easily attached to barbed connectors. FIG. 49 shows chest tube drainage lumen tube section 4902 and chest tube relief lumen tube section 4904. Specifically, at the non-patient end of the transition region, both lumen preferably become circular to allow for proper attachment to standard barbs. The pull-through region shown in FIG. 50 includes chest tube drainage lumen tube section 4902 and chest tube relief lumen tube section 4904. The two tube sections may also be joined, for example with webbing or adhesive. The ends of the two tubes may be tapered to allow for easier insertion into the chest and also easier pulling of the chest tube through, from the inside to the outside, the chest wall. Alternatively, the tubes may not be tapered or only one of the tubes may be tapered. In some embodiments, the relief lumen tube may "dive" into the larger tube so the outer profile on the non-patient end is just that of the drainage tube. This is shown in FIG. 51. The relief tube is also preferably sealed near the non-patient end, for example with a plug of silicone, in order to prevent fluid ingress into the relief lumen as the tube is pulled through the patient wall.

In some embodiments, the device is configured such that when the pneumatic connecter is disconnected from the monitor, the lumens enter a safe state. This safe state may include closing off either or both of the chest tube relief lumen and the drainage tube relief lumen to prevent air from continuously entering the system. The safe state may also include opening the balloon valves and expandable valve in the valve device so that the inner lumen remains open allowing fluid drainage to continue without obstruction. To ensure the balloon valves enter and remain in a safe state, their ports are fluidly tied to the chest tube relief lumen and/or the drainage tube relief lumen when disconnected from the monitor. In this way, the pressures on both sides of the balloon valves are equal and the balloon valves therefore remain in an open state. This is illustrated in FIGS. 52A and 52B, where FIG. 52A shows the connections in the connected state and FIG. 52B shows the connections in the disconnected state.

Figure 52A:
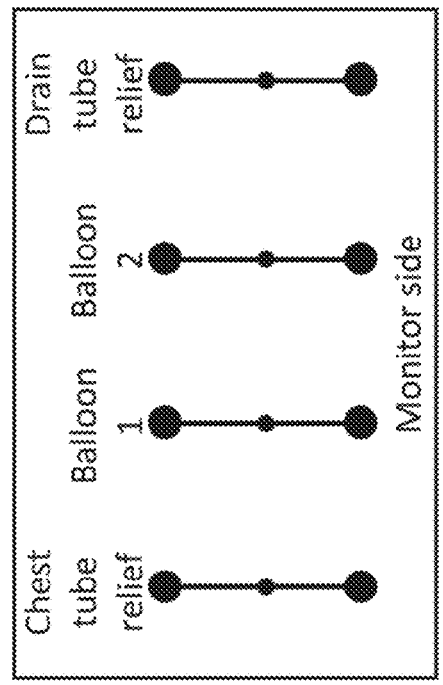
FIGS. 52A-52B show connection states between the pneumatic connecter and the monitor.
Figure 52B:
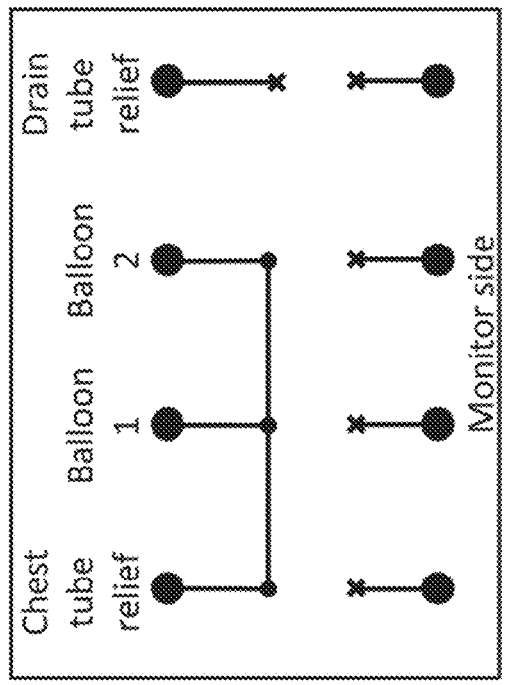
Figure 53:
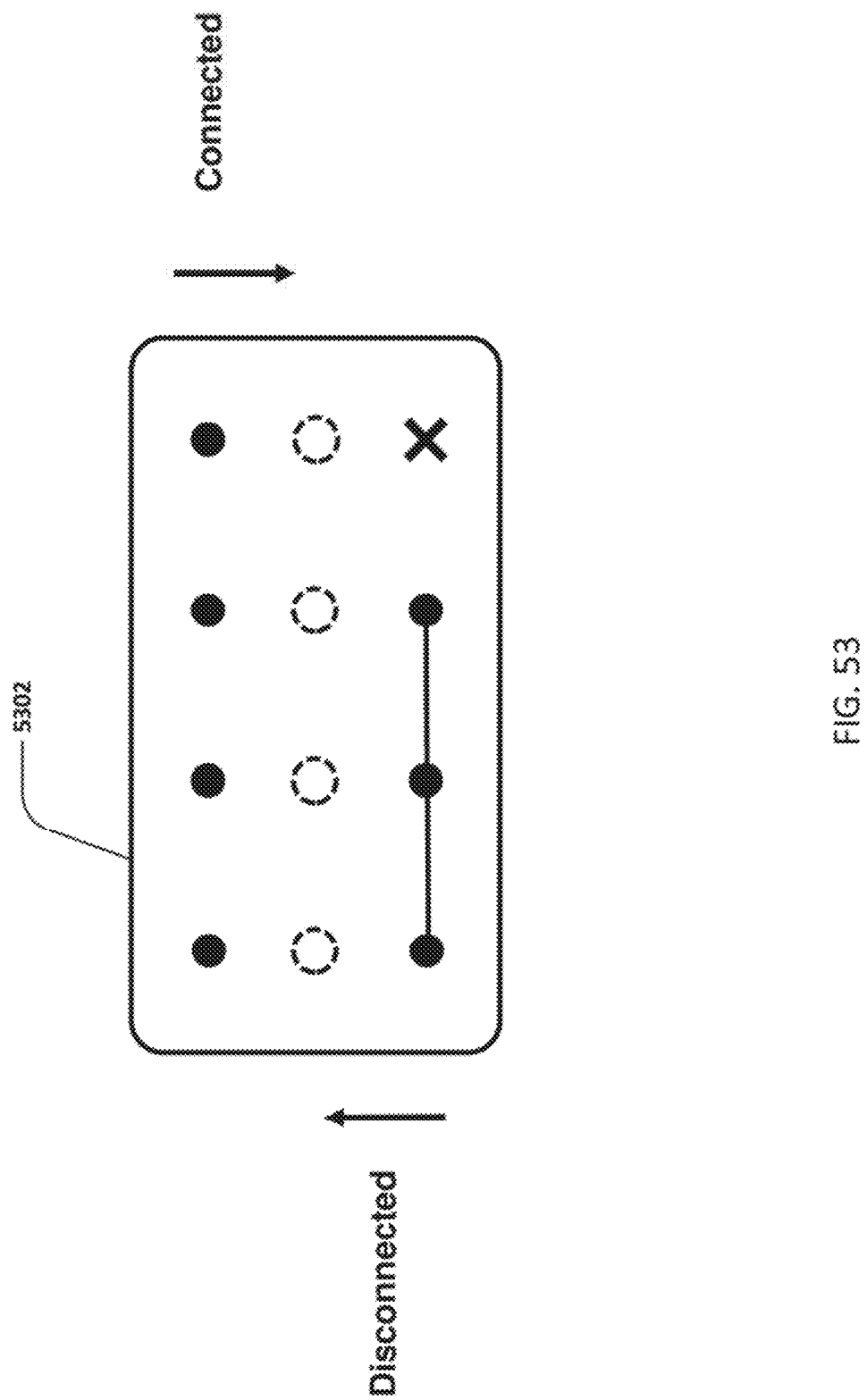
FIG. 53 shows a manifold design.
Figure 54:
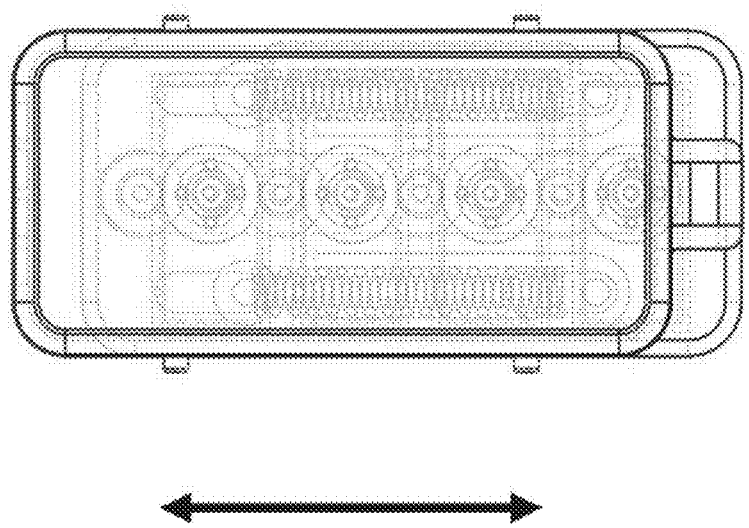
FIG. 54 shows a sliding mechanism.

In one embodiment, the mechanism illustrated in FIGS. 52A and 52B is accomplished by means of a manifold design shown in FIG. 53. In this design, manifold 5302 may be used to either: A) independently connect the lumens to their respective gasket when connected to the monitor, or B) tie the balloon seal lumens to the flush and/or relief lumens when disconnected to the monitor by means of a sliding mechanism that is activated when disconnected from the monitor. This mechanism is shown in FIG. 54 and may include springs within the connecter that keep the lumens in a safe state unless connected to the monitor. The safe connection/disconnection may also be achieved by other means.

Figure 55:
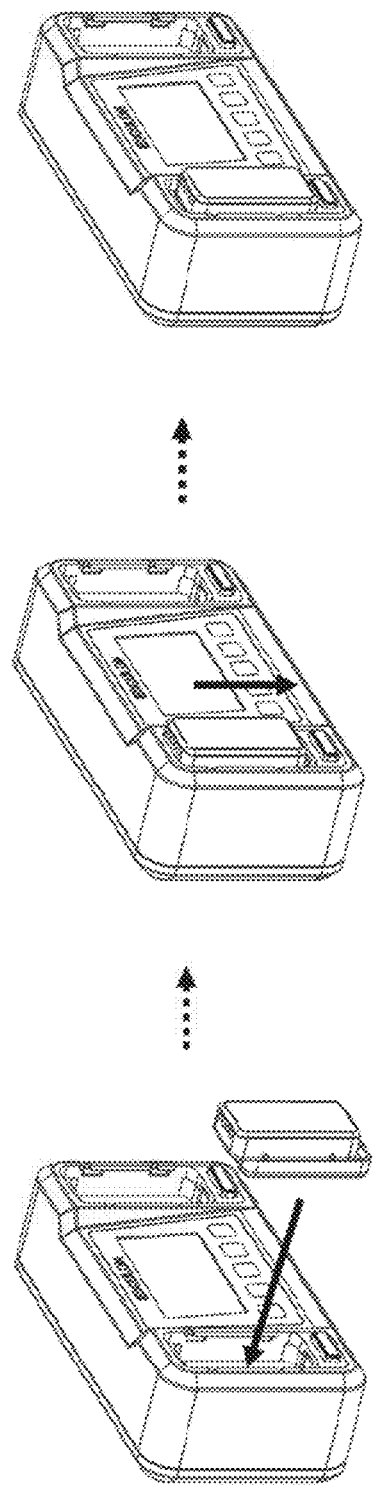
FIG. 55 shows an alternative configuration to the system depicted in FIG. 24.

FIG. 55 shows an alternative configuration to the system depicted in FIG. 24. FIG. 55 shows a pneumatic connecter which connects to the monitor by being placed into its receptacle and then slid into place, thereby making the independent lumen connections. The connecter is held in this position by means of a latch that can be disengaged by the user when removing the connecter. This allows the various lumens to enter the safe state when disconnected.

Figure 56:
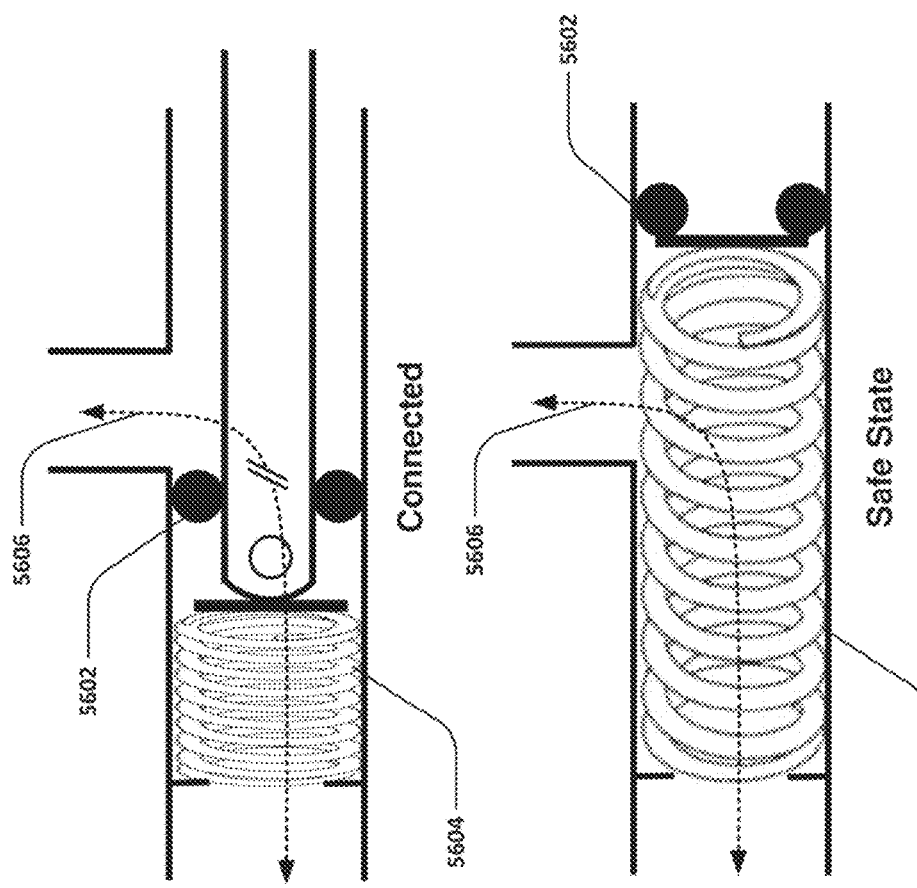
FIG. 56 shows a spring activated valve.

In another embodiment, the same effect of providing a safe state for the lumens is achieved by spring-activated valves that either provide independent paths for the lumens to connect to their respective gaskets, or seal or tie the lumens together. An example of an individual such valve is shown in FIG. 56, and includes O-ring 5602 and spring 5604 in both the connected and disconnected (safe) state. Fluid path 5606 is closed in the connected state and open in the disconnected (safe) state.

In another embodiment, the monitor is capable of keeping the pneumatic connecter connected until the device is in a safe state (i.e. balloon valves are open). Another way of saying this is that the pneumatic connecter cannot be disconnected until the monitor has determined that the system is in safe mode. This may be achieved by mechanical means, such as a latch that the monitor itself engages with the pneumatic connecter when sealing the balloon valves. This may be accomplished using a solenoid valve, motor, or any other suitable means.

Figure 57:
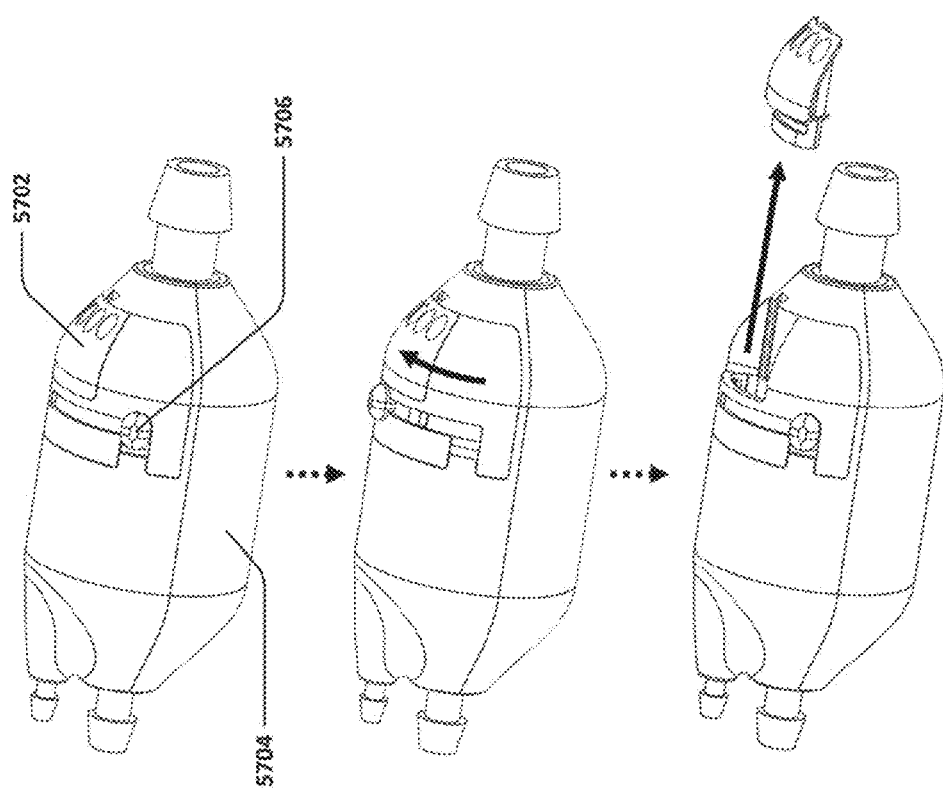
FIG. 57 shows an embodiment of a valve device.

In another embodiment, the pneumatic connecters may be disconnected from the valve device shown in FIG. 21 to achieve a safe disconnected state as described above. This is preferably achieved by the mechanism shown in FIG. 57. To remove pneumatic connecters 5702 from valve device 5704, for example when transferring the patient from the ICU to the step-down unit when active clog clearance and line purging is no longer required, pneumatic connecters 5702 may be disconnected from the valve device 5704. In this embodiment, slider 5706 is moved to tie the lumens to their respective safe states as shown in FIG. 52. The same slider also disengages a latch that keeps the pneumatic connecters in place, thereby allowing the connecter to be removed from the valve device while allowing the lumens in the valve device to remain in a safe sate. In some embodiments, once the pneumatic connecters have been removed, the valve device and/or the pneumatic connecters are locked to prevent re-attachment of the pneumatic connecter after it has been disconnected. This may be accomplished, for example, by a latching mechanism that only engages when the slider is in its fully open position.

Figure 58:
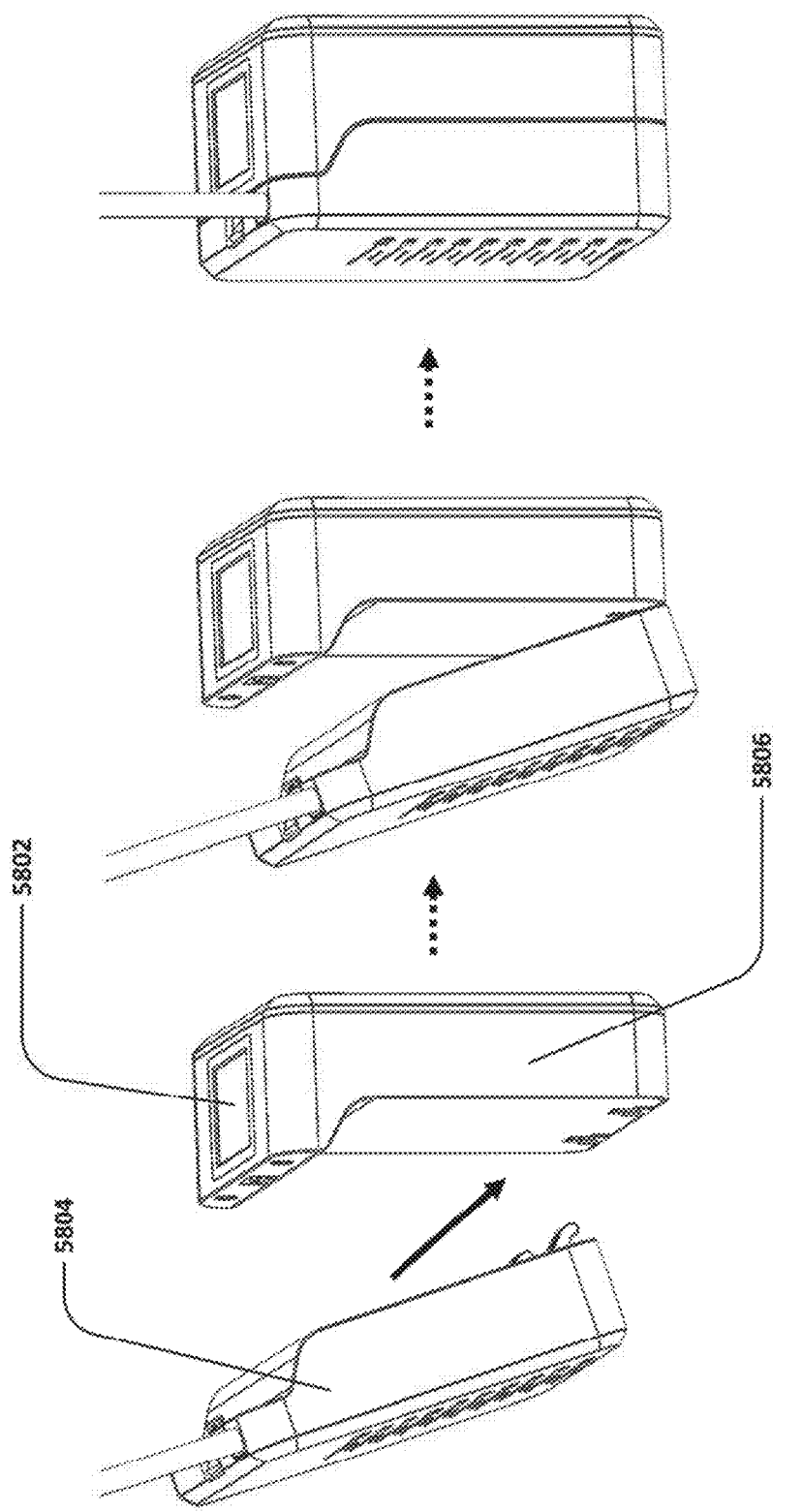
FIG. 58 shows a monitor/controller.

In some embodiments, the chest drainage system includes the monitor/controller shown in FIG. 58. In one embodiment, the monitor includes screen 5802, integrated pump (not shown) and mating ports between suction canister/reservoir 5804 and monitor 5806, including ports to provide suction to the reservoir, open the drainage tube relief lumen valve via integrated solenoid or other means, and capture/secure the drainage tubing and suction canister. In some embodiments, the pneumatic lines are protected by filters integrated into the canister itself to prevent egress of liquid from the canister.

Figure 59:
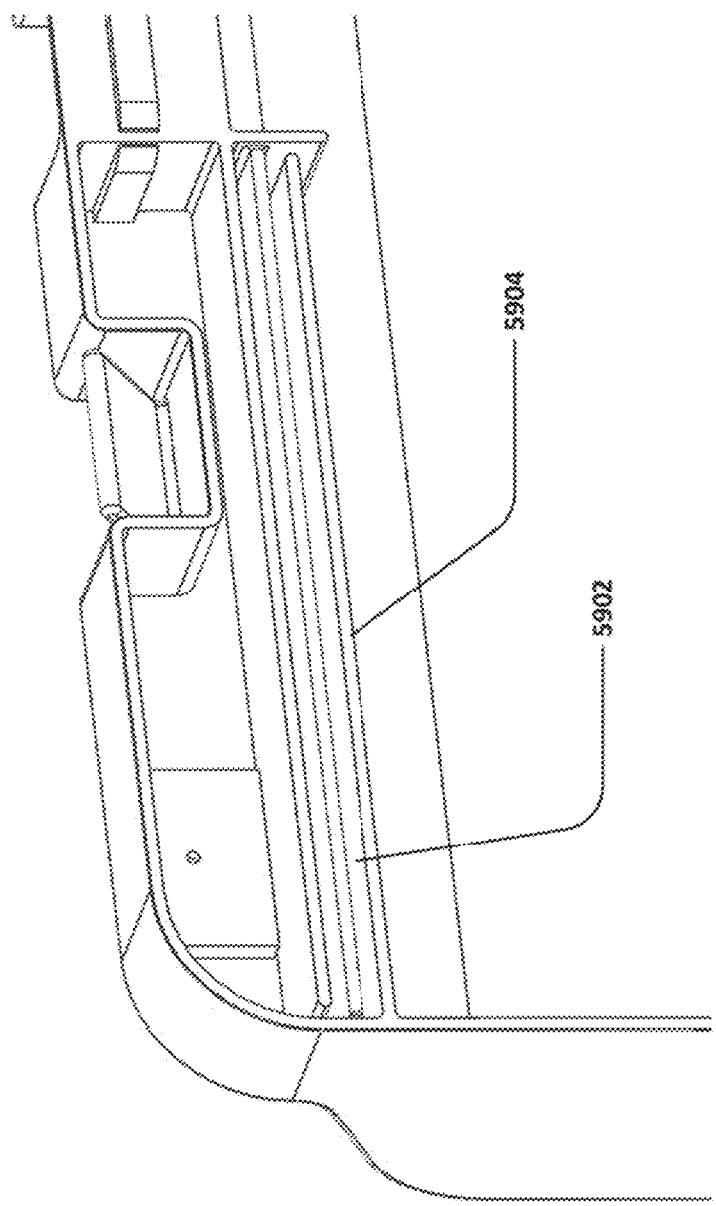
FIG. 59 shows an embodiment of a collection reservoir/canister.

In some embodiments, the suction canister/reservoir is protected from liquid egress by means of a tortuous path created by the internal geometry of the suction canister/reservoir as shown in FIG. 59. The tortuous path may include a series of ribs 5904 and channels 5902 to separate the fluid collection chamber of the reservoir from the vacuum/suction port which connects to the monitor. The tortuous path geometry makes it more difficult for liquid to reach the suction port regardless of monitor orientation.

Figure 60:
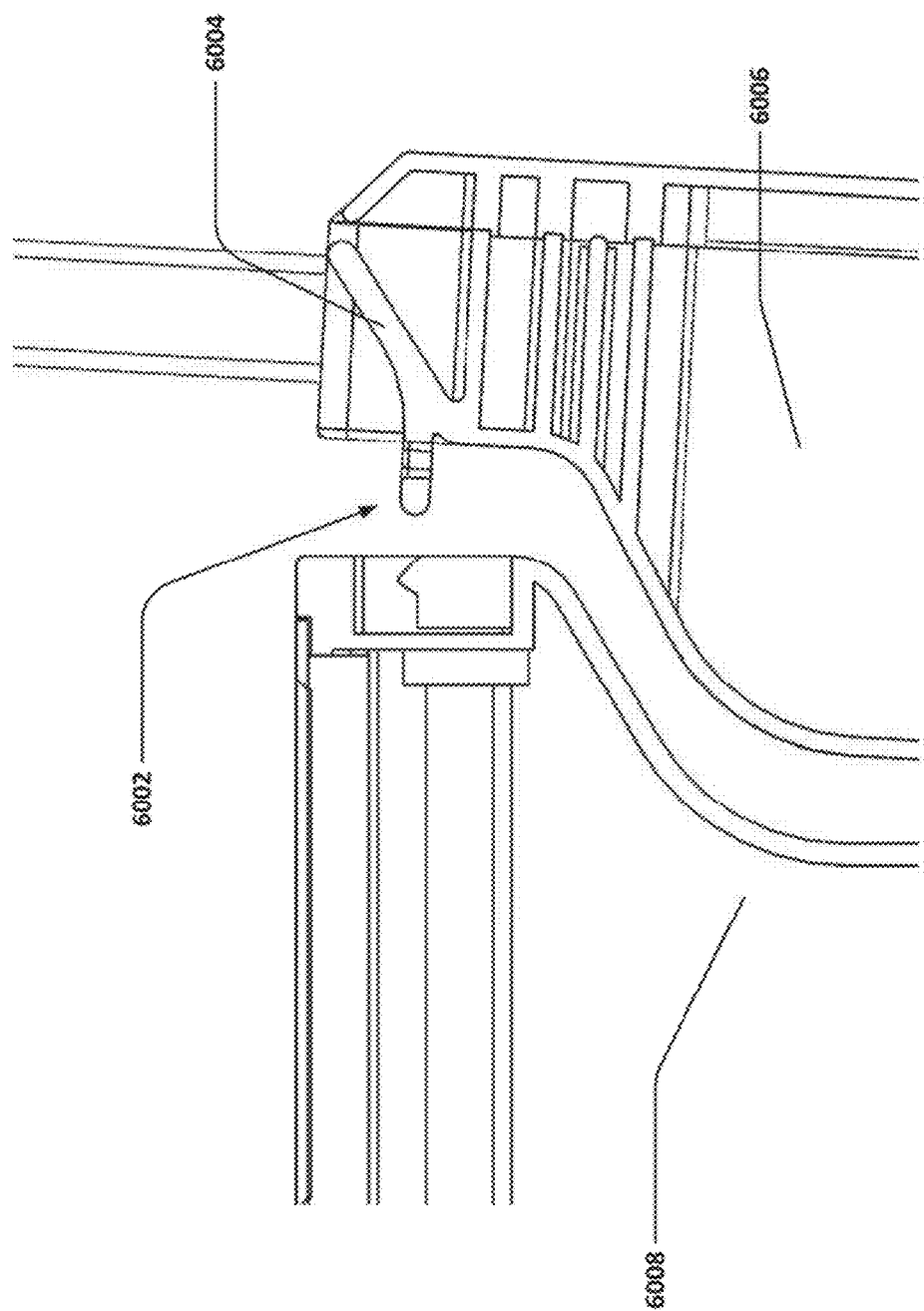
FIG. 60 shows a latching mechanism between the canister/reservoir and the monitor.

In some embodiments, an accelerometer is used to monitor orientation of the monitor and the controller provides an alert when the monitor is in a position that may compromise the suction port. In this example embodiment, the drainage tubing is first connected to the drainage canister and the drainage canister is then connected to the monitor. Alternatively, the drainage tubing drainage lumen and/or drainage tube relief lumen may be connected to the monitor itself, and/or the two tubes (drainage tube drainage lumen and drainage tube relief lumen) may be connected separately. In the exemplary embodiment shown, the canister/reservoir is connected to the front of the monitor, but in other embodiments may be connected to the back or either side of the monitor, or be separate. In one embodiment, the suction canister/reservoir has a latching hinge that mates with a latch on the suction monitor as shown in FIG. 60, such that once the canister is connected to monitor 6008, hinge 6004 must be manually depressed in order to disengage latch 6002 and remove canister 6006 from monitor 6008.

In another embodiment of the device shown in FIG. 61, the monitor has modular attachment receptacle 6102 for accepting any number of accessories for mounting or handling the device, including but not limited to bed mounts, IV pole mounts, carrying straps, or handle 6104, as shown in FIG. 61. In another embodiment, the device may have multiple such attachment receptacles to allow for multiple accessories to be connected at once, for example but not limited to a bed mount and a handle or a handle and carrying straps.

Figure 62:
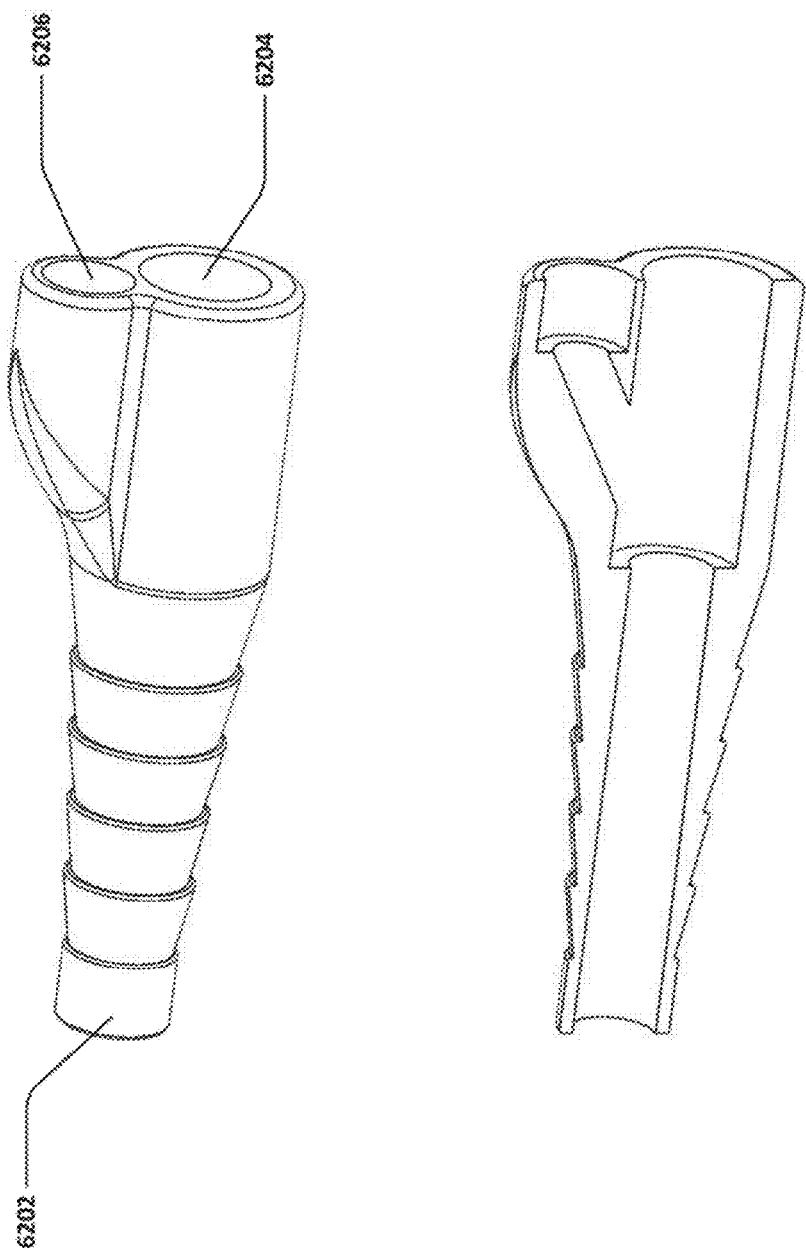
FIG. 62 shows an embodiment of a connection barb.

In some embodiments, the chest drainage system may be used with a standard chest tube without a chest tube relief lumen. In this case, the drainage tube relief lumen and drainage tube lumen join together at a connection barb between the drainage tube and the chest tube. An example of this type of connection barb is shown in FIG. 62. The connecter includes chest tube connecter 6202, drainage lumen connecter 6204 and drainage lumen relief lumen connecter 6206. This connecter arrangement may be particularly appropriate in thoracic surgery where there is less concern of clogging within the chest tube, and clearance of the drainage line to maintain suction pressure is the primary concern. In another embodiment, the same type of connection barb may be used with a chest tube with a chest tube relief lumen that includes any of the passive valves described above and in FIGS. 4 and 5. In this configuration, the passive valves are normally closed, but the pump in the monitor may generate additional suction at temporal intervals (or when a blockage is sensed) in order to surpass the crack pressure of the valve such that it opens and air can sweep the chest tube drainage lumen clear via air from the chest tube relief lumen. This activation may alternatively or additionally occur when the monitor detects that the magnitude of tidal oscillations has diminished, indicating that a blockage is forming within the chest tube. The suction monitor may also temporarily reduce the suction magnitude after such an activation is performed in order to ensure that the passive valve closes again.

Figure 63:
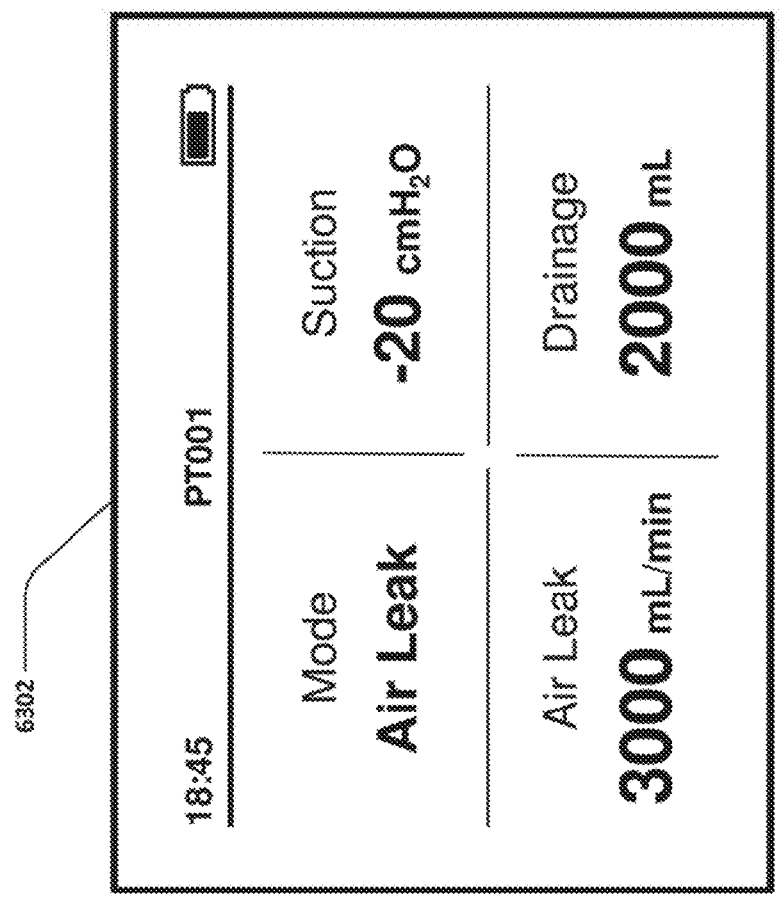
FIG. 63 shows a display.
Figure 64:
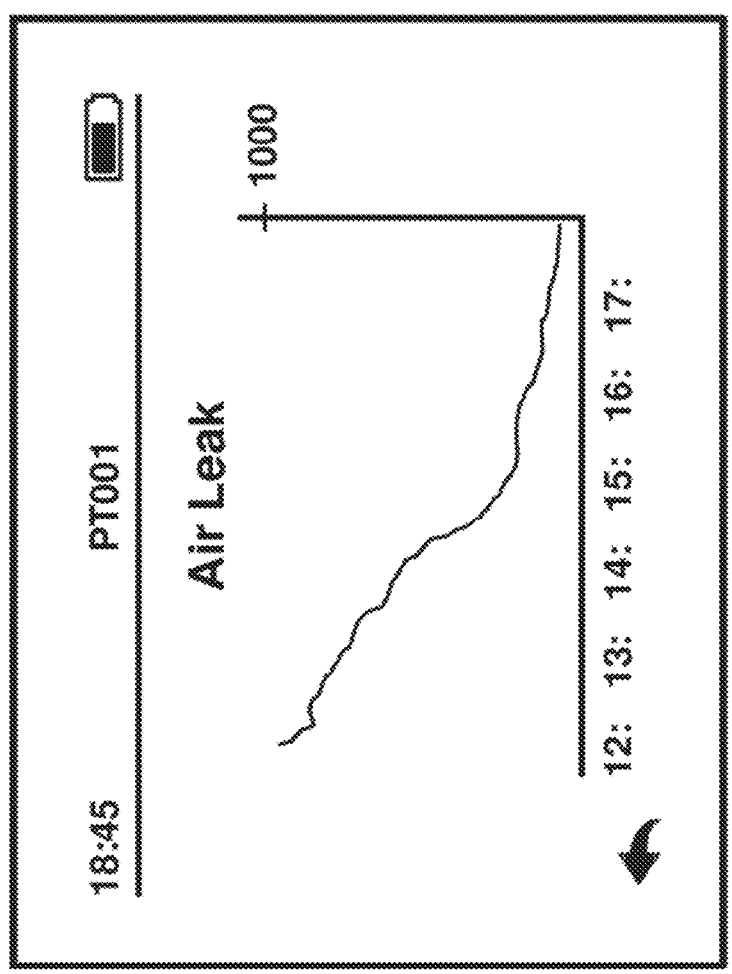
FIG. 64 shows a display.

In one embodiment of the chest drainage system, controller/monitor screen 6302 has touch capability for user input. Alternatively the monitor may employ an array of buttons. An example touchscreen image is shown in FIG. 63. Touching this screen will result in an appropriate response by the monitor, for example touching "suction" takes the user to a screen to adjust the suction value, touching "mode" allows the user to switch between drainage and air leak modes, and touching "drainage" or "air leak" takes the user to a plot of that metric over time, as shown in FIG. 64. When the monitor is showing a graph, touching the x-axis may change the time scale and touching the y-axis may change the flow rate or volume scale (depending on which plot is shown).

In another embodiment of the pneumatic connecter/monitor interface, the device may check for proper seating of the pneumatic connecter with the monitor by performing a self-pressurization check and monitoring for a pressure response that is indicative of a properly-seated connecter. This technique may also be used to detect various sizes of canisters.

In some embodiments of the chest drainage system, the monitor provides pulsatile suction (whether via the valve device or via the pump in the monitor to maintain chest tube patency. This suction may be in the form of a sine wave, square wave, or any other suitable oscillatory waveform, and may oscillate between, for example but not limited to 0 to −40 cmH2O, 0 to −60 cmH2O, 0 to −80 cmH2O, 0 to −100 cmH2O, −10 to −40 cmH2O, −20 to −60 cmH2O, and so on. These embodiments may or may not include a chest tube relief lumen.

Any of the embodiments disclosed herein may be adapted to function with more than one chest tube, for example, by connecting more than one chest tube to the valve device or the connection barb.

What is claimed is:

1. A drainage system, comprising:
   a tube configured for insertion into a body of a subject, wherein the tube defines a tube relief lumen and tube drainage lumen in fluid communication with one another;
   a tube relief lumen valve in fluid communication with the tube relief lumen;
   a suction pump in fluid communication with the tube drainage lumen; and
   a controller in communication with the tube, wherein the controller is programmed to actuate the suction pump at a first level of suction which maintains the tube relief lumen valve in a closed configuration and at a second level of suction which reconfigures the tube relief lumen valve to an open configuration, wherein the second level of suction is communicated to the tube relief lumen valve via the tube drainage lumen to open the tube relief lumen valve.

2. The system of claim 1 wherein the tube relief lumen valve is configured such that a pressure differential is formed between an ambient pressure and the tube relief lumen, wherein the tube relief lumen valve is configured to close at a first pressure differential and to open at a second pressure differential which is different from the first pressure differential.

3. The system of claim 1 wherein the second level of suction is more negative than the first level of suction.

4. The system of claim 1 wherein the controller is configured to actuate the suction pump at the second level when tidal oscillations detected by the controller are diminished.

5. The system of claim 1 wherein the controller is configured to actuate the suction pump at the second level automatically on a periodic basis.

6. The system of claim 1 wherein the tube comprises a chest tube defining one or more drainage openings in fluid communication with the tube drainage lumen.

7. The system of claim 1 further comprising a drainage tube in fluid communication with the tube drainage lumen.

8. The system of claim 7 further comprising a fluid reservoir in fluid communication with the drainage tube.

9. The system of claim 7 further comprising a drainage tube relief lumen in fluid communication with the tube drainage lumen or the drainage tube.

10. The system of claim 9 further comprising a drainage tube relief lumen valve in fluid communication with the drainage tube relief lumen.

11. The system of claim 10 wherein the drainage tube relief lumen valve comprises a passively operated valve.

12. The system of claim 10 wherein the drainage tube relief lumen valve comprises an actively operated valve.

13. The system of claim 2 wherein the second pressure differential to open the tube relief lumen valve is greater than the first pressure differential to close the tube relief lumen valve.

14. The system of claim 1 wherein the tube relief lumen valve comprises a passively operated valve.

15. The system of claim 1 wherein the tube relief lumen valve comprises an actively operated valve.

16. The system of claim 1 wherein the tube relief lumen valve comprises a magnetic valve.

17. The system of claim 16 wherein the magnetic valve comprises a housing having a first element secured with the housing and a second element attached to a seal, wherein the seal has a first position in which a magnetic force between the first and second elements is greater than the first pressure differential and maintains the magnetic valve in a closed configuration, and wherein the seal has a second position in which the magnetic force is less than the second pressure differential and maintains the magnetic valve in an open configuration.

18. The system of claim 17 wherein one or both of the first and second elements comprises a magnet.

19. The system of claim 1 wherein the controller is configured to monitor a rate of air flow from the tube drainage lumen as an indicator of a thoracic air leak.

20. The system of claim 19 wherein the controller is configured to determine at least one parameter of the air leak.

21. The system of claim 19 further comprising a flow meter in communication with the controller.

22. The system of claim 19 wherein the controller is configured to monitor a number of revolutions of a vacuum pump in fluid communication with the tube drainage lumen.

* * * * *